(12) United States Patent
Proia

(10) Patent No.: US 10,500,193 B2
(45) Date of Patent: Dec. 10, 2019

(54) COMBINATION THERAPY OF HSP90 INHIBITORS WITH PLATINUM-CONTAINING AGENTS

(71) Applicant: SYNTA PHARMACEUTICALS CORP., Lexington, MA (US)

(72) Inventor: David Proia, Newton, MA (US)

(73) Assignee: Synta Pharmaceuticals Corporation, Lexington, MA (US)

( * ) Notice: Subject to any disclaimer, the term of this patent is extended or adjusted under 35 U.S.C. 154(b) by 0 days.

(21) Appl. No.: 15/940,055

(22) Filed: Mar. 29, 2018

(65) Prior Publication Data

US 2018/0221345 A1   Aug. 9, 2018

Related U.S. Application Data

(63) Continuation of application No. 14/355,689, filed as application No. PCT/US2012/063039 on Nov. 1, 2012, now abandoned.

(60) Provisional application No. 61/554,706, filed on Nov. 2, 2011.

(51) Int. Cl.

| A61K 31/4196 | (2006.01) |
|---|---|
| A61K 33/24 | (2019.01) |
| A61K 45/06 | (2006.01) |
| A61K 31/555 | (2006.01) |
| A61K 31/661 | (2006.01) |
| A61K 31/675 | (2006.01) |
| A61P 35/04 | (2006.01) |
| A61K 31/282 | (2006.01) |
| A61P 35/00 | (2006.01) |
| A61K 31/4184 | (2006.01) |

(52) U.S. Cl.
CPC ........ *A61K 31/4196* (2013.01); *A61K 31/555* (2013.01); *A61K 31/661* (2013.01); *A61K 31/675* (2013.01); *A61K 33/24* (2013.01); *A61K 45/06* (2013.01); *A61K 31/282* (2013.01); *A61K 31/4184* (2013.01); *A61P 35/00* (2018.01); *A61P 35/04* (2018.01)

(58) Field of Classification Search
CPC .............. A61K 31/282; A61K 31/4184; A61K 31/4196; A61P 35/00; A61P 35/04
USPC ........................................................ 514/383
See application file for complete search history.

(56) References Cited

U.S. PATENT DOCUMENTS

| 2,898,343 A | 8/1959 | Klingsberg |
|---|---|---|
| 3,189,614 A | 6/1965 | Pesson |
| 3,714,231 A | 1/1973 | Kolling et al. |
| 3,898,272 A | 8/1975 | Kurz et al. |
| 4,178,253 A | 12/1979 | Lee et al. |
| 4,269,846 A | 5/1981 | Huang et al. |
| 4,624,995 A | 11/1986 | Katritzky et al. |
| 4,740,568 A | 4/1988 | Katritzky et al. |
| 4,931,084 A | 6/1990 | Findeisen et al. |
| 5,006,650 A | 4/1991 | Barbachyn |
| 5,219,722 A | 6/1993 | Tanaka et al. |
| 5,298,520 A | 3/1994 | Baker et al. |
| 5,371,101 A | 12/1994 | Itoh et al. |
| 5,395,818 A | 3/1995 | Haas et al. |
| 5,436,252 A | 7/1995 | Sorensen et al. |
| 5,464,810 A | 11/1995 | Haas et al. |
| 5,466,820 A | 11/1995 | Itoh et al. |
| 5,476,946 A | 12/1995 | Linker et al. |
| 5,478,827 A | 12/1995 | Oku et al. |
| 5,489,598 A | 2/1996 | Connor et al. |
| 5,510,362 A | 4/1996 | Matassa et al. |
| 5,532,378 A | 7/1996 | Daum et al. |
| 5,538,988 A | 7/1996 | Martinez et al. |
| 5,552,369 A | 9/1996 | Findeisen et al. |
| 5,624,931 A | 4/1997 | Oku et al. |
| 5,625,074 A | 4/1997 | Daum et al. |
| 5,654,438 A | 8/1997 | Findeisen et al. |
| 5,663,362 A | 9/1997 | Haas et al. |

(Continued)

FOREIGN PATENT DOCUMENTS

| AU | 2012200157 A1 | 2/2012 |
|---|---|---|
| DE | 10 01 992 B | 2/1957 |

(Continued)

OTHER PUBLICATIONS

Gridelli et al., The Oncologist, Alpha Med Press, 12: 191-200 (2007).

(Continued)

*Primary Examiner* — Kevin E Weddington
(74) *Attorney, Agent, or Firm* — Andrea L. C. Reid; Dechert LLP

(57) ABSTRACT

A pharmaceutical combination comprising a platinum-containing anticancer agent, and an Hsp90 inhibitor according to the following formulae (I) & (Ia), a tautomer, or a pharmaceutically acceptable salt thereof, wherein the variables structural formulae are defined herein. Also provided is a method of treating a proliferative disorder such as cancer in a subject in need thereof, using the pharmaceutical combination described herein.

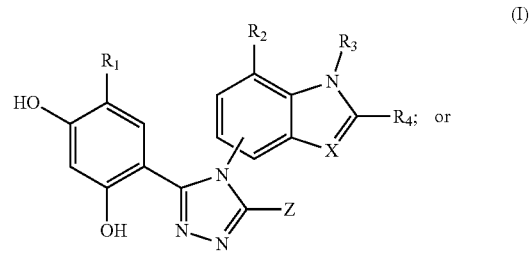

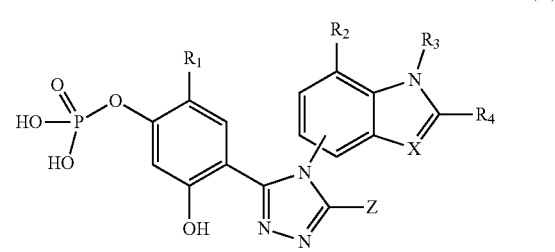

7 Claims, 3 Drawing Sheets

(56) References Cited

U.S. PATENT DOCUMENTS

| | | |
|---|---|---|
| 5,861,358 A | 1/1999 | Findeisen et al. |
| 5,869,509 A | 2/1999 | Romine et al. |
| 5,888,694 A | 3/1999 | Yamada et al. |
| 5,952,502 A | 9/1999 | McCullough et al. |
| 5,968,921 A | 10/1999 | Gold |
| 5,972,844 A | 10/1999 | Muller et al. |
| 6,077,861 A | 6/2000 | Romine et al. |
| 6,080,772 A | 6/2000 | Tang et al. |
| 6,180,567 B1 | 1/2001 | Muller et al. |
| 6,194,090 B1 | 2/2001 | Okada |
| 6,200,931 B1 | 3/2001 | Muller et al. |
| 6,200,934 B1 | 3/2001 | Muller et al. |
| 6,251,831 B1 | 6/2001 | Muller et al. |
| 6,258,957 B1 | 7/2001 | Linker et al. |
| 6,271,249 B1 | 8/2001 | Romine et al. |
| 6,337,342 B1 | 1/2002 | Karabelas et al. |
| 6,492,406 B1 | 12/2002 | Karabelas et al. |
| 6,492,409 B1 | 12/2002 | Karabelas et al. |
| 6,583,090 B1 | 6/2003 | Gewehr et al. |
| 6,660,286 B1 | 12/2003 | Lambert et al. |
| 6,677,277 B1 | 1/2004 | Schallner et al. |
| 6,747,055 B1 | 6/2004 | Ho et al. |
| 6,855,705 B1 | 2/2005 | Tian et al. |
| 6,858,598 B1 | 2/2005 | McKearn et al. |
| 6,921,763 B2 | 7/2005 | Hirst et al. |
| 6,946,456 B2 | 9/2005 | Rosen et al. |
| 7,081,466 B2 | 7/2006 | Koya et al. |
| 7,247,734 B2 | 7/2007 | Drysdale et al. |
| 7,473,784 B2 | 1/2009 | Liu et al. |
| 7,608,635 B2 | 10/2009 | Ying et al. |
| 7,662,813 B2 | 2/2010 | Ying et al. |
| 7,825,148 B2 * | 11/2010 | Ying .................... C07D 249/08 514/383 |
| 8,034,834 B2 | 10/2011 | Du et al. |
| 8,053,456 B2 | 11/2011 | Sun et al. |
| 8,063,083 B2 | 11/2011 | Foley |
| 8,106,083 B2 | 1/2012 | Burlison et al. |
| 8,183,384 B2 | 5/2012 | Chimmanamada et al. |
| 8,188,075 B2 | 5/2012 | Ying et al. |
| 8,299,107 B2 | 10/2012 | Chimmanamada et al. |
| 8,318,790 B2 | 11/2012 | Ying et al. |
| 8,329,736 B2 | 12/2012 | Chimmanamada et al. |
| 8,329,899 B2 | 12/2012 | Ying et al. |
| 8,362,055 B2 | 1/2013 | Ying et al. |
| 8,415,377 B2 | 4/2013 | Sun et al. |
| 8,450,500 B2 | 5/2013 | Chimmanamada et al. |
| 8,486,932 B2 | 7/2013 | Burlison et al. |
| 8,524,712 B2 | 9/2013 | Lee et al. |
| 8,628,752 B2 | 1/2014 | Zhou et al. |
| 8,629,285 B2 | 1/2014 | Ying et al. |
| 8,648,071 B2 | 2/2014 | Burlison et al. |
| 8,648,104 B2 | 2/2014 | Du et al. |
| 8,742,133 B2 | 6/2014 | Ying et al. |
| 8,748,424 B2 | 6/2014 | Chimmanamada et al. |
| 8,785,658 B2 | 7/2014 | Chimmanamada et al. |
| 8,835,464 B2 | 9/2014 | Sun et al. |
| 8,901,308 B2 | 12/2014 | Ying et al. |
| 8,906,885 B2 | 12/2014 | El-Hariry et al. |
| 8,921,407 B2 | 12/2014 | Ying et al. |
| 8,927,548 B2 | 1/2015 | Ying et al. |
| 8,937,094 B2 | 1/2015 | Burlison et al. |
| 8,969,396 B2 | 3/2015 | Du et al. |
| 8,993,608 B2 | 3/2015 | Du et al. |
| 9,006,277 B2 | 4/2015 | Sun et al. |
| 9,067,884 B2 | 6/2015 | Chimmanamada et al. |
| 9,090,569 B2 * | 7/2015 | Ying .................... C07D 249/08 |
| 9,101,614 B2 | 8/2015 | Foley |
| 9,108,933 B2 | 8/2015 | Du et al. |
| 9,120,745 B2 * | 9/2015 | Ying .................... C07F 9/65583 |
| 9,126,953 B2 | 9/2015 | Ying et al. |
| 9,156,794 B2 | 10/2015 | Ying et al. |
| 9,156,836 B2 | 10/2015 | Burlison et al. |
| 9,205,086 B2 | 12/2015 | Blackman et al. |
| 9,206,162 B2 | 12/2015 | Sun et al. |
| 2003/0054996 A1 | 3/2003 | Nicchitta et al. |
| 2003/0092749 A1 | 5/2003 | Dombroski et al. |
| 2003/0134886 A1 | 7/2003 | Karabelas et al. |
| 2003/0216369 A1 | 11/2003 | Rosen et al. |
| 2003/0216385 A1 | 11/2003 | Tobe et al. |
| 2004/0082498 A1 | 4/2004 | Strehlow |
| 2004/0106604 A1 | 6/2004 | Beight et al. |
| 2004/0110662 A1 | 6/2004 | Rosen et al. |
| 2004/0110684 A1 | 6/2004 | Balligand et al. |
| 2004/0204426 A1 | 10/2004 | Kubo et al. |
| 2004/0214818 A1 | 10/2004 | Tobe et al. |
| 2004/0235813 A1 | 11/2004 | Wanker et al. |
| 2004/0266746 A1 | 12/2004 | Rosen et al. |
| 2005/0019918 A1 | 1/2005 | Sumimoto et al. |
| 2005/0020534 A1 | 1/2005 | Johnson et al. |
| 2005/0020556 A1 | 1/2005 | Johnson et al. |
| 2005/0020557 A1 | 1/2005 | Johnson et al. |
| 2005/0020558 A1 | 1/2005 | Johnson et al. |
| 2005/0026893 A1 | 2/2005 | Johnson et al. |
| 2005/0048533 A1 | 3/2005 | Sidransky et al. |
| 2005/0054589 A1 | 3/2005 | Johnson et al. |
| 2005/0054625 A1 | 3/2005 | Johnson et al. |
| 2005/0058956 A1 | 3/2005 | Watanabe et al. |
| 2005/0154039 A1 | 7/2005 | Glacera Contour et al. |
| 2005/0267087 A1 | 12/2005 | Poulaki et al. |
| 2005/0267185 A1 | 12/2005 | Marino et al. |
| 2005/0272083 A1 | 12/2005 | Seshagiri |
| 2005/0288347 A1 | 12/2005 | Hodge et al. |
| 2006/0078494 A1 | 4/2006 | Polvino |
| 2006/0135594 A1 | 6/2006 | Fraley et al. |
| 2006/0167070 A1 | 7/2006 | Q |
| 2006/0211737 A1 | 9/2006 | Huang et al. |
| 2006/0235058 A1 | 10/2006 | Cheung et al. |
| 2007/0066831 A1 | 3/2007 | MacDonald et al. |
| 2007/0203194 A1 | 8/2007 | Zelle et al. |
| 2007/0238699 A1 | 10/2007 | Demko et al. |
| 2008/0004266 A1 | 1/2008 | Du et al. |
| 2008/0027047 A1 | 1/2008 | Ying |
| 2008/0125587 A1 | 5/2008 | Chimmanamada et al. |
| 2008/0182857 A1 | 7/2008 | Eggenweiler et al. |
| 2008/0269218 A1 | 10/2008 | Kuramochi et al. |
| 2008/0318241 A1 | 12/2008 | Dang et al. |
| 2009/0131529 A1 | 5/2009 | Sherman et al. |
| 2009/0232906 A1 | 9/2009 | Hausheer |
| 2010/0069442 A1 | 3/2010 | Ying et al. |
| 2010/0093717 A1 | 4/2010 | Q |
| 2010/0203043 A1 | 8/2010 | Ree et al. |
| 2010/0209929 A1 | 8/2010 | Fantl et al. |
| 2010/0249185 A1 | 9/2010 | Q |
| 2010/0280032 A1 | 11/2010 | Zhou et al. |
| 2011/0009397 A1 | 1/2011 | Ying et al. |
| 2011/0046125 A1 | 2/2011 | Ying |
| 2011/0118298 A1 | 5/2011 | Fritz et al. |
| 2011/0152310 A1 | 6/2011 | Burlison et al. |
| 2011/0224206 A1 | 9/2011 | Ying et al. |
| 2011/0301212 A1 | 12/2011 | Du et al. |
| 2011/0319404 A1 | 12/2011 | Foley |
| 2012/0064175 A1 | 3/2012 | Vukovic et al. |
| 2012/0122869 A1 | 5/2012 | Ying et al. |
| 2012/0219522 A1 | 8/2012 | Xi |
| 2012/0245186 A1 | 9/2012 | Blackman et al. |
| 2012/0330009 A1 | 12/2012 | Ying et al. |
| 2013/0072461 A1 | 3/2013 | Chimmanamada et al. |
| 2013/0072536 A1 | 3/2013 | Ying et al. |
| 2013/0150385 A1 | 6/2013 | Blackman et al. |
| 2013/0156755 A1 | 6/2013 | Blackman et al. |
| 2013/0171105 A1 | 7/2013 | Blackman et al. |
| 2013/0172333 A1 | 7/2013 | Jain et al. |
| 2013/0225870 A1 | 8/2013 | Lee et al. |
| 2013/0303493 A1 | 11/2013 | Burlison et al. |
| 2013/0331357 A1 | 12/2013 | Proia et al. |
| 2013/0338155 A1 | 12/2013 | Ying |
| 2013/0345219 A1 | 12/2013 | Lee et al. |
| 2014/0004516 A1 | 1/2014 | Sattler et al. |
| 2014/0005145 A1 | 1/2014 | Proia |
| 2014/0024030 A1 | 1/2014 | Blackman et al. |
| 2014/0045908 A1 | 2/2014 | Blackman et al. |
| 2014/0051664 A1 | 2/2014 | Foley et al. |
| 2014/0051665 A1 | 2/2014 | Proia et al. |
| 2014/0094436 A1 | 4/2014 | Ying et al. |

(56) References Cited

U.S. PATENT DOCUMENTS

| | | |
|---|---|---|
| 2014/0127740 A1 | 5/2014 | Zhou et al. |
| 2014/0135370 A1 | 5/2014 | Vukovic |
| 2014/0141511 A1 | 5/2014 | Zhou et al. |
| 2014/0178366 A1 | 6/2014 | Blackman et al. |
| 2014/0194388 A1 | 7/2014 | Proia et al. |
| 2014/0221375 A1 | 8/2014 | Du et al. |
| 2014/0228418 A1 | 8/2014 | Proia et al. |
| 2014/0255348 A1 | 9/2014 | Proia |
| 2014/0256680 A1 | 9/2014 | Proia et al. |
| 2014/0288301 A1 | 9/2014 | Chimmanamada et al. |
| 2014/0294808 A1 | 10/2014 | El-Hariry et al. |
| 2014/0296176 A1 | 10/2014 | Proia et al. |
| 2014/0296186 A1 | 10/2014 | Ying et al. |
| 2014/0315943 A1 | 10/2014 | Proia et al. |
| 2014/0363830 A1 | 12/2014 | Ying |
| 2015/0051203 A1 | 2/2015 | Chimmanamada et al. |
| 2015/0094349 A1 | 4/2015 | Du et al. |
| 2015/0099721 A1 | 4/2015 | Acquaviva et al. |
| 2015/0119395 A1 | 4/2015 | Chimmanamada et al. |
| 2015/0126499 A1 | 5/2015 | Burlison et al. |
| 2015/0150850 A1 | 6/2015 | El-Hariry et al. |
| 2015/0150851 A1 | 6/2015 | Jain et al. |
| 2015/0174134 A1 | 6/2015 | Du et al. |
| 2015/0183771 A1 | 7/2015 | Ying et al. |
| 2015/0283147 A1 | 10/2015 | Proia et al. |
| 2015/0366885 A1 | 12/2015 | Ying et al. |
| 2016/0000756 A1 | 1/2016 | Ying et al. |
| 2016/0009724 A1 | 1/2016 | Burlison et al. |

FOREIGN PATENT DOCUMENTS

| | | | |
|---|---|---|---|
| DE | 10 2005 007304 A1 | 8/2006 | |
| EP | 1 857 446 A1 | 11/2007 | |
| EP | 2025347 A1 | 2/2009 | |
| EP | 2133094 A1 | 12/2009 | |
| EP | 2333103 A1 | 6/2011 | |
| FR | 2546887 A1 | 12/1984 | |
| JP | 57070820 A | 5/1982 | |
| JP | 59010574 A | 1/1984 | |
| JP | 2000284412 A | 10/2000 | |
| JP | 2003114488 A | 4/2003 | |
| WO | WO-1996/022985 A1 | 8/1996 | |
| WO | WO-1997/03067 A1 | 1/1997 | |
| WO | WO-1998/04135 A1 | 2/1998 | |
| WO | WO-1998/27092 A1 | 6/1998 | |
| WO | WO-2000/071537 A1 | 11/2000 | |
| WO | WO-2000/78750 A1 | 12/2000 | |
| WO | WO-2002/006213 A2 | 1/2002 | |
| WO | WO-2002/36171 A1 | 5/2002 | |
| WO | WO-2002/066447 A1 | 8/2002 | |
| WO | WO-2002/069900 A2 | 9/2002 | |
| WO | WO-2002/072576 A1 | 9/2002 | |
| WO | WO-2002/094833 A1 | 11/2002 | |
| WO | WO-2003/013430 A2 | 2/2003 | |
| WO | WO-2003/045926 A1 | 6/2003 | |
| WO | WO-2003/047523 A2 | 6/2003 | |
| WO | WO-2003/050295 A2 | 6/2003 | |
| WO | WO-2003/055860 A1 | 7/2003 | |
| WO | WO-2003/077914 A1 | 9/2003 | |
| WO | WO-2003/082266 A1 | 10/2003 | |
| WO | WO-2003/089006 A1 | 10/2003 | |
| WO | WO-2004/045617 A1 | 6/2004 | |
| WO | WO-2004/050087 A1 | 6/2004 | |
| WO | WO-2004/056782 A1 | 7/2004 | |
| WO | WO-2004/072051 A1 | 8/2004 | |
| WO | WO-2004/081037 A1 | 9/2004 | |
| WO | WO-2004/082676 A1 | 9/2004 | |
| WO | WO-2004/089367 A1 | 10/2004 | |
| WO | WO-2004/089415 A2 | 10/2004 | |
| WO | WO-2004/089416 A2 | 10/2004 | |
| WO | WO-2004/094819 A1 | 11/2004 | |
| WO | WO-2004/096212 A1 | 11/2004 | |
| WO | WO-2004/096781 A1 | 11/2004 | |
| WO | WO-2005/000300 A1 | 1/2005 | |
| WO | WO-2005/016920 A1 | 2/2005 | |
| WO | WO-2005/027972 A2 | 3/2005 | |
| WO | WO-2005/033102 A2 | 4/2005 | |
| WO | WO-2005/039569 A1 | 5/2005 | |
| WO | WO-2005/040345 A2 | 5/2005 | |
| WO | WO-2005/041879 A2 | 5/2005 | |
| WO | WO-2005/044194 A2 | 5/2005 | |
| WO | WO-2005/087750 A1 | 9/2005 | |
| WO | WO-2005/097758 A1 | 10/2005 | |
| WO | 2006/008503 A1 | 1/2006 | |
| WO | WO-2006/018082 A1 | 2/2006 | |
| WO | WO-2006/039977 A1 | 4/2006 | |
| WO | WO-2006/047631 A2 | 5/2006 | |
| WO | WO-2006/061712 A2 | 6/2006 | |
| WO | WO-2006/087077 A2 | 8/2006 | |
| WO | WO-2006/091246 A1 | 8/2006 | |
| WO | WO-2006/095783 A1 | 9/2006 | |
| WO | WO-2006/101052 A1 | 9/2006 | |
| WO | WO-2007/111904 A2 | 10/2007 | |
| WO | WO-2007/134678 A2 | 11/2007 | |
| WO | WO-2008/086857 A1 | 7/2008 | |
| WO | WO-2008/108386 A1 | 9/2008 | |
| WO | 2008/153730 A2 | 12/2008 | |
| WO | 2008153730 A2 | 12/2008 | |
| WO | WO-2008/156573 A1 | 12/2008 | |
| WO | 2009023211 A1 | 2/2009 | |
| WO | WO-2009/099649 A1 | 8/2009 | |
| WO | WO-2009/102446 A2 | 8/2009 | |
| WO | WO-2010/020618 A1 | 2/2010 | |
| WO | WO-2010/060937 A2 | 6/2010 | |
| WO | WO-2010/138377 A1 | 12/2010 | |
| WO | WO-2011049946 A1 | 4/2011 | |
| WO | WO-2011/060328 A1 | 5/2011 | |
| WO | WO-2011146803 A1 | 11/2011 | |
| WO | 2011149824 A1 | 12/2011 | |
| WO | WO-2011149824 A1 | 12/2011 | |
| WO | 2012037072 A1 | 3/2012 | |
| WO | WO-2012037072 A1 | 3/2012 | |
| WO | 2014/189937 A1 | 11/2014 | |
| WO | 2015/109218 A1 | 7/2015 | |

OTHER PUBLICATIONS

Thaterjee, et al., Ganetespib resistance in KRAS mutant NSCLC is mediated through bypassing the G2/M checkpoint and reactivating the PI3KIMTOR pathway at the 106th Annual Meeting of the American Association for Cancer Research, Apr. 18, 2015.

Ganji, Ganetespib sensitizes colorectal cancer in vitro and in vivo to a clinically relevant regimen of radiation and chemotherapy at the 106th Annual Meeting of the American Association for Cancer Research, Apr. 18, 2015.

Ray-Coquard, et al., Part I of GANNET53: A multicenter phase I/II trial of the Hsp90 inhibitor ganetespib with weekly paclitaxel in women with high-grade serous, high-grade endometrioid, or undifferentiated, platinum-resistant epithelial ovarian, fallopian tube or primary peritoneal cancer at The 2015 American Society of Clinical Oncology (ASCO) Annual Meeting, May 29, 2015.

El-Rayes et al., Phase I study of ganetespib, capecitabine and radiation in rectal cancer at The 2015 American Society of Clinical Oncology (ASCO) Annual Meeting, May 29, 2015.

Lazenby et al, "The HSP90 inhibitor ganetespib: A potential effective agent for Acute Myeloid Leukemia in combination with cytarabine", Leukemia Research 39(6): 617-627 (2015).

Alexandrova et al, "Improving survival by exploiting tumour dependence on stabilized mutant p53 for treatment", 523: n352-356 (2015).

Gomez-Casal et al, "The HSP90 Inhibitor Ganetespib Radiosensitizes Human Lung Adenocarcinoma Cells" Cancers (Basel), 7(2):876-907 (2015).

Ramalingam et al, "A Randomized Phase 2 Study of Ganetespib, A Heat Shock Protein 90 Inhibitor, In Combination With Docetaxel in Second-Line Therapy of Advanced Non-Small-Cell Lung Cancer (GALAXY-1)" Annal of Oncology, 26(8): 1741-1748 (2015).

Proia and Kaufmann, "Targeting Heat-Shock Protein 90 (HSP90) as a Complementary Strategy to Immune Checkpoint Blockade for Cancer Therapy", Cancer Immunol Res, 3(6): 583-589 (2015).

(56) References Cited

OTHER PUBLICATIONS

Definition "prevention" from the Institue for International Medical Education [online], [Retrieved on Mar. 24, 2011]. Retrieved from the internet<http://www.lime.org/glossary.htm>. Published Feb. 2002, p. 1, 2, 26, 27 and 39.

"Lung Cancer (Non-Small Cell) In-Depth Report" by the New York Times. [online] Retrieved on Jul. 9, 2015. Retrieved from the internet at<http://www.nytimes.com/health/guides/disease/lung-cancer-non-small-cell/print.html>.

Hanna, N. et al. Randomized Phase III Trial of Pemetrexed Versus Docetaxel in Patients With Non-Small Cell Lung Cancer Previously Treated With Chemotherapy. Journal of Clinical Oncology, 22(9): 1589-1597 (2004).

"Combination Chemotherapy" by RnCeus® (2007) Retrieved [online] Feb. 26, 2015. Retrieved from <http://mceus.com/chem/combo.html>.

Bischof, et al.. Interaction of Pemetrexed Disodium (ALIMTA,Multitargeted Antifolate) and Irradiation In Vitro. International Journal of Radiation Oncology Biology Physics and, 52(5): 1381-1388 (2002).

Anderson, Chem and Biol 10:787-797 (2003).

Thiel, Nature Biotechnol 2:513-519 (2004).

Solit et al., "Inhibition of Heat Shock Protein 90 function Down-Regulates Akt Kinase and Sensitizes Tumors to Taxol," Cancer Res 63: 2139 (2003).

Ewesuedo et al. the Oncologist 2: 359-364 (1997).

Shah et al. (Molecular and Cellular Endocrinology, 219: 127-139 (2004).

Wang, "A Hierarchial Network of Transcription Factors Govern Androgen Receptor-Dependent Prostate Cancer Growth" Molecular Cell, 27:380-392 (2007).

West et al., "A novel classification of lung cancer into molecular subtypes" PLos ONE; vol. 7 (2): 2012.

Sasaki et al., "New strategies for treatment of ALK-rearraned non-small cell lung cancers" Clin. Cancer Res. 17(23): 7213-8, 2011.

Moser C, et al., Blocking heat shock protein-90 inhibits the invasive properties and hepatic growth of human colon cancer cells and improves the efficacy of oxaliplatin in p53-deficient colon cancer tumors in vivo. Molecular Cancer Therapeutics, vol. 6(11) pp. 2868-2878, (2007).

Banerji U, et al., An in vitro and in vivo study of the combination of the heat shock protein inhibitor 17-allylamino-17-demethoxygeldanamycin and carboplatin in human ovarian cancer models, Cancer Chemotherapy and Pharmacology, vol. 62(5) pp. 769-778 (2008).

Dote, et al., 374 Poster. Synergic antiproliferative effect of Hsp90 inhibitor in combination with cisplatin in gastric carcinoma cell lines, European Journal of Cancer Supplement, vol. 5(4) p. 77 (2007).

Hwang M, et. al., HSP90 Inhibitors: MUlti-Targeted Antitumor Effects and Novel Combinational Therapeutic Approaches in Cancer Therapy. Current Medicinal Chemistry, vol. 16(24) pp. 3081-3092 (2009).

International Search Report and Written Opinion issued in PCT/US2012/063039.

Abdel-Fattah, et al., "1-Azido-4-phenyl-1,4-butanedione as a Convenient Precursor for the Synthesis of Various Nitrogen Heterocycles," *Egyptian J. of Chemistry*, 46(1), 153-162 (2003).

Abdel-Hamid, Hoda A., et al., "Synthesis of some biologically active heterocycles. Reactions of the hydrazide of 2'-thienoylanthranilic acid and its 3,5-dibromo derivative," Phosphorus, Sulfur and Silicon and the Related Elements (1992), 72(1-4):237-247.

Abramson et al., "The heat shock protein 90 inhibitor IPI-504 induces apoptosis of AKT-dependent diffuse large B-cell lymphomas", British Journal of Haematology, vol. 144, No. 3, pp. 358-366 (2009).

Acquaviva et al, "FGFR3 Translocations in Bladder Cancer: Differential Sensitivity to HSP90 Inhibition Based on Drug Metabolism", Mol Cancer Res, 12:1042-1054 (2014).

Acquaviva et al, "mTOR Inhibition Potentiates HSP90 Inhibitor Activity via Cessation of HSP Synthesis", Mol Cancer Res, 12:703-713 (2014).

Acquaviva et al, "Overcoming acquired resistance to BRAF inhibitors in melanoma with the HSP90 inhibitor ganetespib", Poster, 103rd Annual Meeting American Association for Cancer Research (AACR), Mar. 31-Apr. 4, 2012—Chicago, IL.

Acquaviva et al, "Potent Anticancer Actions of the Hsp90 Inhibitor Ganetespib (STA-9090) in Wild-Type EGFR Models of Lung Cancer", Poster, Apr. 4, 2011—Orlando, FL.

Acquaviva et al, "Targeting KRAS mutant NSCLC with the Hsp90 inhibitor ganetespib", Poster, AACR-IASLC Joint Conference on Molecular Origins of Lung Cancer: Biology, Therapy, and Personalized Medicine, Jan. 10, 2012—San Diego, CA.

Acquaviva et al, "The Hsp90 inhibitor ganetespib promotes the degradation of FGFR3 in bladder cancer models and induces regression in tumors harboring oncogenic FGFR3 fusions", Poster, AACR/NCI/EORTC Molecular Targets and Cancer Therapeutics, Oct. 19-23, 2013—Boston, MA.

Acquaviva et al,"Overcoming Acquired BRAF Inhibitor Resistance in Melanoma via Targeted Inhibition of Hsp90 with Ganetespib", Mol Cancer Ther, 13:353-363 (2014).

Acquaviva et al,"Targeting KRAS-Mutant Non-Small Cell Lung Cancer with the Hsp90 Inhibitor Ganetespib", Mol Cancer Ther, 11:2633-2643 (2012).

Al-Saadi, et al., "In Vitro Antitumor Screening of Some Polysubstituted Pyrazole Analogs", Saudi Pharmaceutical Journal, Saudi Pharmaceutical Society, Riyad, SA, 2005, vol. 13, pp. 89-96.

Anderson et al., "CCT241533 Is a Potent and Selective Inhibitor of CHK2 that Potentiates the Cytoxicity of PARP Inhibitors" Cancer Research, vol. 71(2): 463-472, Jan. 15, 2011.

Andotra, C.S., et al., "Synthesis and Biocidal Activity of N-Phenyl-2,6-Substituted Aryl-5-Thione-1, 2, 4-Triazolo[1, 5-a]-s-Triazine-7-Ones," Indian Journal of Heterocyclic Chemistry, 5:237-238 (1996).

Anonymous: "Sample name: NCI-H1975 (Cosmic ID: 924244)", Catalogue of Somatic Mutations in Cancer (COSMIC), Sep. 18, 2006 (Sep. 18 2006), XP002658470, Retrieved from the Internet: URL:http://www.sangerac.uk/perl/genetics/CGP/core_line_viewer?action=sample&name=NCI-H1975; decor=printable [retrieved on Sep. 7, 2011].

Arkenau H-T, et al., Targeting BRAF for Patients with Melanoma, British Journal of Cancer, 104(3):392-398, Feb. 2011.

Awada et al, "Enchant-1 Trial (NCT01677455): an Open-Label Multicenter Phase 2 Window-of-Opportunity Study Evaluating Ganetespib in Women With First-Line Metastatic Breast Cancer", Poster, The 2013 American Society of Clinical Oncology (ASCO) Annual Meeting, May 31-Jun. 4, 2013—Chicago, IL.

Awada et al, "The ENCHANT-1 Trial (NCT01677455): An Open-Label Multicenter Phase 2 Proof of Concept Study Evaluating First-Line Ganetespib Monotherapy in Women With Metastatic HER2-Positive or Triple-Negative Breast Cancer (TNBC)", Poster, San Antonio Breast Cancer Symposium, Dec. 10-14, 2013—San Antonio, TX.

Ayca, E. et al., "Mass Spectra of Some 3,4-Disubstituted-2-1,2,4-Triazolin-5-Ones," Chimica Acta Turcica, 11: 285-289 (1983).

Ayca, E. et al., "Preparation of 3-Alkyl(aryl)-4-Aryl-A2-1,2,4-Triazolin-5-Ones," Chimica Acta Turcica, 9: 99-108(1981).

Bahceci, S., et al., "Reactions of 4-Amino-4,5-Dihydro-1H-1,2,4-Triazol-5-ones and 4-Amino-4H-1,2,4-Triazoles with Some Carboxylic Acid Anhydrides," *Turkish Journal of Chemistry*, 22(3): 237-241 (1998).

Balmanno et al, "Intrinsic resistance to the MEK ½ inhibitor AZD6244 (ARRY-142886) is asociated with weak ERK½ signaling and/or strong PI3K signaling in colorectal cancer cell lines." Int J of Cancer 125: 2332-2341 (2009).

Bansal et al, "Heat shock protein 90 regulates the expression ofWilms tumor 1 protein in myeloid leukemias", Blood, 25:4591-4599 (2010).

Bao, R., et al: "CUDE-305, a Novel Syntehic HSP90. Inhibitor with Unique Pharmacologic Properties for Cancer Therapy" Clin Cancer Res. 15: 4046-4057, 2009.

(56) References Cited

OTHER PUBLICATIONS

Barker, et al., "Inhibition of Hsp90 acts synergistically with topoisomerase II poisons to increase the apoptotic killing of cells due to an increase in topoisomerase II mediated DNA damage," Nucleic Acids Res. 2006; 34(4):1148-57.
Barril, X., et al., "Structure-Based Discovery of a New Class of Hsp90 Inhibitors," *Biorganic & Medicinal Chemistry Letters*, 2005, 15, pp. 5187-5191.
Beger et. al., World Journal of Surgery, 2003, Societe Internationale de Chirurgie, vol. 27, pp. 1075-1084.
Beilstein Registry No. 4329746; 4 pp (2010).
Beilstein Registry No. 4562121; 2 pp (2010).
Beilstein Registry No. 546443; 2 pp (2012).
Beilstein Registry No. 551485; 2 pp (2010).
Beilstein Registry No. 567249; 1 pg (2010).
Beilstein Registry No. 574001, 5-26-09-00436, XP-002372386 (2005).
Beilstein Registry No. 6162150; 2 pp (2010).
Beilstein Registry No. 625992, 5-26-03-00436, XP-002372385 (2005).
Beilstein Registry No. 6742740; 2 pp (2010).
Berenbaum ("Synergy, additivism and antagonism in immunosuppression", Clin. Exp Immunol. vol. 28, pp. 1-18, Published; 1977).
Bergethon K. et al., "ROS1 rearrangements define a unique molecular class of lung cancers", Journal of Clinical Oncology, American Society of Clinical Oncology, US, vol. 30, No. 8, pp. 863-870, 2012.
Bhat, A. K., et al., "Chemotherapy of Fungus Infections: Part I—I-Acyl-4-substituted Thiosemicarbazides, 3-Aryl-4-substituted-5-mercapto-1,2,4-4H-triazoles & Related Compounds," *Indian Journal of Chemistry* 5(9):397-401 (Sep. 1967).
Bischt et al., "Geldanamycin and 17-Allylamino-17-demethoxygeldanamycin Potentiate the in Vitro and in Vivo Radiation Response of Cervical Tumor Cells via the Heat Shock Protein 90-Mediated Intracellular Signaling and Cytotoxicity", Cancer Res, 63:8984-8995 (2003).
Blackman et al, "Hsp90 Inhibitor STA-9090 Enhances the Activity of Standard of Care Therapies in Erlotinib-Sensitive and -Resistant NSCLC Models", 101st AACR Annual Meeting, Apr. 19, 2010—Washington, DC.
Blackman Ronald K et al: "Hsp90 inhibitor STA-9090 enhances the activity of standard of care therapies in erlotinib-sensitive and -resistant NSCLC models". Proceedings of the Annual Meeting of The American Association for Cancer Research. vol. 51. Apr. 19, 2010 (Apr. 19, 2010). p. 640.
Blasina et al., "Breaching the DNA damage checkpoint via PF-00477736, a novel small-molecular inhibitor of checkpoint kinase 1" Molecular Cancer Therapeutics, vol. 7(8): 2394-2404, Aug. 1, 2008.
Bognar, Rezso, et al. Magyar Kemiai Folyoirat (1974), 80(3), 114-16.
Bonvini et al., "Nucleophosmin-anaplastic lymphoma kinase (NPM-ALK), a novel Hsp90-cleint tyrosine kinase: down-regulation of NPM-ALK expression and tyrosine phosphorylation in ALK(+) CD30(+) lymphoma cells by the Hsp90 antagonist 17-allylamino, 17-demethoxygeldanamycin", Cancer Res, 62:1559-1566 (2002).
Brahmer et al, "A Phase 2 Study of the Hsp90 Inhibitor Ganetespib (STA-9090) asMonotherapy in Patients with Advanced NSCLC", Presentation, IASLC 14th World Conference on Lung Cancer, Jul. 7, 2011—Amsterdam, The Netherlands.
Brough, et al., "3-(5-chloro-2,4-dihydroxyphenyl)-pyrazole-4-carboxamides as inhibitors of the Hsp90 molecular chaperone," *Bioorganic and Medicinal Chemistry Letters* (2005), 15:5197-5201.
Bucci et al. "Geldanamycin, an inhibitor of heat shock protein 90 (Hsp90) mediated signal transduction has anti-inflammatory effects and interacts with glucocorticoid receptor in vivo", Br.J.Pharmacol., 2000, vol. 131, pp. 13-16.
Burger's Medicinal Chemistry 336-337 (Manfred Wolff, ed., John C Wiley & Sons, 1980).

Busacca, "Novel mechanisms of sensitivity and acquired resistance to Hsp90 inhibition by Ganetespib", Presentation, 15th World Conference on Lung Cancer, Oct. 27-30, 2013 Sydney, Australia.
Byrn et al. Solid-State Chemistry of Drugs, 2d, Chapter 11 Hydrates and Solvates, 233-247 (1999).
Calabresi and Chabner (Goodman & Gilman's The Pharmacological Basis of Therapeutics, 10th ed, 2001).
Caldwell et al., "Structure-Based Design of Potent and Selective 2-(Quinazolin-2-yl)phenol Inhibitors of Checkpoint Kinase 2" J. of Medicinal Chemistry, vol. 54(2): 580-590, Jan. 27, 2011.
Cameron et al, "Targeting HSP90 in breast cancer: Enchant-1 (NCT01677455) phase 2 proof of concept study of ganetespib in first-line treatment of women with metastatic HER2 positive or triple negative breast cancer (TNBC)", Presentation, 9th European Breast Cancer Conference, Mar. 19-21, 2014—Glasgow, Scotland.
Cameron et al, "The ENCHANT™ Trial: An open label multicenter phase 2 window of opportunity study evaluating ganetespib (STA-9090) monotherapy in women with previously untreated metastatic HER2 positive or triple negative breast cancer (TNBC)", ESMO 2012 Congress, Sep. 28-Oct. 2, 2012—Vienna, Austria.
Cansiz, A. et al., "Synthesis of Some New 4, 5-Substituted-4H-1, 2, 4-triazole-3-thiol Derivatives," Molecules, 9:204-212 (2004).
Cao, X, et al: "Non-invasive MRI tumor imaging and synergistic anticancer effect of HSP90 inhibitor and glycolysis inhibitor in RIP1-Tag2 transgenic pancreatic tumor model", Cancer Chemotherapy and Pharmacology, Springer, Berlin, DE, vol. 62, No. 6, Feb. 6, 2008 (Feb. 6, 2008), pp. 985-994, XP019625579.
Cava, M.P. And Levinson, Mj., "Thionation Reactions of Lawesson's Reagents," *Tetrahedron Report No.* 19241(22):5061-5087 (1985).
Cesur N., and Cesur, Z., "Synthesis of Some 4-Thiazoline and 4H-1,2,4-Triazole Derivatives of Imidazo(1,2-a) Pyridine as Possible Anticonvulsants" *II Farmaco*, 49(10): 679-681 (1984).
Chabner et. al., Nature Reviews Cancer, 2005, Nature Publishing Group, vol. 5, pp. 65-72.
Chaloupka, Stanislav, et al., "Reactions of 3-dirnethylamino-2, 2-dirnethyl-2H-azirine with Benzoic Acid Hydrazides," Chimia, Chemical Abstracts Service, Database CA [oneline], 32(9):332-333 (1978).
Chapman, Paul B., et al., Improved Survival with Vemurafenib in Melanoma with BRAF V600E Mutation, New England Journal of Medicine, 364(26):2507-2516, Jun. 30, 2011.
Cherkasov, R.A., et al., "Organothiophosphorus Reagents in Organic Synthesis," *Tetrahedron Report No.* 18641(13):2567-2624 (1985).
Cheung, K.M.J., et al. "The identification, synthesis, protein crystal structure and in vitro biochemical evaluation of a new 3,4-diarylpyrazole class of Hsp90 inhibitors," *Bioorganic & Medicinal Chemistry Letter*, 15: 3338-3343 (2005).
Cho et al, "A phase I dose-escalation study of the Hsp90 inhibitor ganetespib administered twice weekly in patients with solid tumors: updated report", Poster, The 2011 American Society of Clinical Oncology (ASCO) Annual Meeting Jun. 3-7, 2011.
Ciugureanu et al., "Study of the biological acitivity of some new thiosemicarbazides and their derivatives with triazole and thiadiazole nucleus. II. Testing of antifungal acitivity", Farmacia, 1982, vol. 30, pp. 49-56.
Ciugureanu, C., and Ungureanu, M., "Synthesis of Novel 1,2,4-Triazoles and 1,3,4-Thiadiazoles Derivatives of 1,3-Benzoxazole," *Analele Stiintifice Ale Universitatii*, 5:151-158 (1997).
Ciugureanu, C., et al., "Studial activiatii biologice a unor noi tiosemicarbazide si a derivatilor acestora cu nucleu triazolic si tiadiazolic. IV. Testarea Activitatii citostatice," Farmacia, XXX(2): 101-110 (1982).
Ciugureanu, C., et al., "Studial Activitatii biologice a unor noi tiosemicarbazide si a derivatilor acestora cu nucleu triazolic si tiadiazolic III. Testarea activitatii antimicrobiene," *Farmacia, XXX*(1): 57-64 (1982).
Cleary et al, A phase I dose-escalation study of the Hsp90 inhibitor STA-9090 administered twice weekly in patients with solid tumors, Poster, The 2010 American Society of Clinical Oncology (ASCO) Annual Meeting, Jun. 4-8, 2010—Chicago, IL.

(56) References Cited

OTHER PUBLICATIONS

Coburn, M.D., etal., "Picrylamino-Substituted Heterocycles III. 1,2,4,-Triazoles (1,2)," *Journal of Heterocyclic Chemistry* 5(2): 199-203 (Apr. 1968).

Colanceska-Pagenovic, et al., "Synthesis, Antibacterial and Antifungal Activity of 4-Substituted-5-Aryl-1,2,4-Triazoles", Molecules, 2001, vol. 6, pp. 815-824.

Colgan, Stephen M. et al., "Hypoxia-induced lactate dehydrogenase expression and tumor angiogenesis", Clinical Colorectal Cancer, 6 (6), p. 442-446, 2007.

Corso et al, "Evaluating the HSP90 Inhibitor Ganetespib as a Radiosensitizing Agent in Breast Cancer Models In Vitro", Poster, The American Society for Radiation Oncology (ASTRO) 54th Annual Meeting, Oct. 28-31, 2012—Boston, MA.

Cowen, et al., "HSP90 Potentiates the Rapid Evolution of New Traits: Drug Resistance in Diverse Fungi", Science, 2005, vol. 309, p. 2185-2189.

Csermely P. et al, "The 90-kDa molecular chaperone family; structure, function, and clinical applications. A comprehensive review.", Pharmacology & Therapeutics, vol. 79, No. 2, pp. 129-168, 1998.

Cuzick et. al., The Lancet, 2003, vol. 361, pp. 296-300.

Davidson, J.S., "A Preparation of 3-Amino-4,5-diaryl-I ,2,4-triazoles," *Communications*:359-361 (1979).

Davies et al. Bortezomib-Based Combinations in the Treatment of Non-Small Cell Lung CancerClinical Lung Cancer (2005) vol. 7, pp. S59-S63.

Demetri et al, "Phase 2 study of ganetespib (STA-9090) single agent in patients with metastatic and/or unresectable GIST", Poster, The 2011 American Society of Clinical Oncology (ASCO) Annual Meeting, Jun. 3-7, 2011.

Demetri, et al., "Overcoming Resistance to Tyrosine Kinase Inhibitors (TKIs) through Inhibition of Heat Shock Protein 90 (Hsp90) Chaperon Function in Patienets with Metastatic GIST: Results of a Phase I Trial of IPI-504, a Water-Soluble Hsp90Inhibitor", European Journal of Cancer. Supplement, Pergamon, Oxford, GB, 2006, vol. 4, p. 173, 570 Poster Abstract.

Demetri, et al., Final results from a phase III study of IPI-504 (retaspimycin hydrochloride) versus placebo in patients (pts) with gastrointestinal stromal tumors (GIST) following failure of kinase inhibitor therapies. ASCO Annual Meeting, Abstract, Jun. 4-8, 2010.

Dent et al, "Synergistic combinations of signaling pathway inhibitors: mechansims for improved cancer therapy." Drug Resistance Updates 12: 65-73 (2009).

Dias, S. et al., "VEGF.sub.165 Promotes Survival of Leukemic Cells by Hsp9O-Mediated Induction of Bcl-2 Expression and Apoptosis Inhibition," Blood, 99(7):2532-2540 (2002).

Dias, S.da R., et al., "Activated B-RAF Is an Hsp90 Client Protein That Is Targeted by the Anticancer Drug 17-Allylamino-17-Demethoxygeldanamycin," Cancer Research 65(23):10686-10691 (Dec. 1, 2005).

Diaz et al, "Ganetespib, an HSP90 Inhibitor, Sensitizes Colorectal Cancers to the Effects of Ionizing Radiation", Poster, The American Society for Radiation Oncology (ASTRO) 54th Annual Meeting, Oct. 28-31, 2012—Boston, MA.

Dogan, et al., "Synthesis and Preliminary Anticancer Activity of New 1H-4,5-Dihydro-3-(3-Hydroxy-2-Naphthyl)-4-Substituted-1,2,4-Triazoli Ne-5-Thiones. Part II", Indian Journal of Chemistry, 2005, vol. 44B, pp. 2301-2307.

Dogan, et al., "Synthesis, structure elucidation and antimicrobial activity of some 3-hydroxy-2-naphthoic acid hydrazide derivative", Farmaco, 1998, vol. 53, pp. 462-467.

Doleschall et al, "A novel aldehyde synthesis based on the reduction of s-triazolo[2,3-c]quinazolin4-ium derivatives," Acta Chima Acad. Sci. Hung., 90(4):419-424 (1976).

Dowlati, et ai, Mol Cancer Ther 2004;3:459-463.

Duran, A., et al., "Synthesis and preliminary anticancer activity of new 1,4-dihydro-3-(3-hydroxy-2-naphthyl)-4-substituted-5*H*-1,2,4-triazoline-5-thiones," *Farmaco* (2002), 57(7):559-564.

Dymock, B.W., et al., "Inhibitors of HSP90 and Other Chaperones for the Treatment of Cancer," *Expert Opin. Ther. Patents*, 14(6): 837-847 (2004).

Dymock, Brian W., et al., "Novel, Potent Small-Molecule Inhibitors of the Molecular Chaperone Hsp90 Discovered Through Structure-Based Design," *J. Med. Chem.*, 2005, 48 pp. 4212-4215.

Eckstein, M., et al., "The Aminoxides of Physiologically Active Compounds," Department of Pharmaceutical Chemistry, Academy of Medicine, Cracow: 197-204, Diss. Pharm., 9 (1957).

Edwards A. et al, "Effect of the histone deacetylase inhibitor LBH589 against epidermal growth factor receptor-dependent human lung cancer cells", Molecular Cancer Therapeutics 20070901 US Lnkd-DOI: 10.1158/1535-7163.MCT-006-0761, vol. 6, No. 9, Sep. 1, 2007 (Sep. 1, 2007), pp. 2515-2524.

El-Sharief, A.M. et al., "1, 4-Phenylenediisothiocyanate in the Synthesis of Bis-(Thiourea, Benzothiazole, Quinazoline, 1, 3-Benzoxazine and Imidazolidineiminothiones) Derivatives," Phosphorus, Sulfur, and Silicon, 179:267-275 (2004).

El-Sharief, A.M., et al., "Utility of Cyanothioformamides in Synthesis of Some Bis(Imidazole, Oxazole, Thiazole, Oxadiazole, Triazole, Benzoxazinethione and Quinazoline) Derivatives," *J. Chem. Research (S)*: 162-167 (2003).

El-Zahar, M.I., et al., "Synthesis of Some Novel 3-(N-Alkyl Carbamoyl) and 3-(1,2,4-Triazol-3-yl)-1,8-Naphthyridines of Anticipated Biological Activity," *Egypt. J. Chem.*, 45(2): 323-344 (2002).

Engel Jorg B et al: "Effects of lobaplatin as a single agent and in combination with TRAIL on the growth of triple-negative p53-mutated breast cancers in vitro.", Anti-Cancer Drugs 2012, vol. 23, No. 4, pp. 426-436.

Fennell et al, "Ultra-deep sequencing of free DNA to identify predictive, mutated HSP90 clients in the GALAXY-1 TrialTM (NCT01348126): A randomized phase IIB/III study of ganetespib (STA-9090) in combination with docetaxel versus docetaxel alone in subjects with stage IIIb/IV NSCLC", Poster, The 2013 Annual Meeting of the American Association of Cancer Research (AACR), Apr. 6-10, 2013—Washington D.C.

Fletcher et al, "HSP90 inhibitor STA □9090 potently suppresses secondary KIT kinase □domain mutations responsible for gastrointestinal stromal tumor (GIST) progression during imatinib therapy", Poster, AACR-NCI-EORTC Molecular Targets and Cancer Therapeutics, Nov. 17, 2009—Boston, MA.

Foley et al, "Hsp90 Inhibitor STA-9090 Induces HIF1A Degradation in the Hypoxic Regions of Solid Tumors", Poster, 101st AACR Annual Meeting, Apr. 19, 2010—Washington, DC.

Foley et al, "Synergy Between the Novel Hsp90 Inhibitor STA-9090 and Taxanes in Preclinical Models of NSCLC", Poster, AACR-IASLC Joint Conference on Molecular Origins of Lung Cancer, Jan. 12, 2010—Coronado, CA.

Foley et al: "Pharmacodynamic Analysis of the Hsp90 Inhibitor STA-9090 in a Lung Cancer Xenograft Model Supports an Infrequent Dosing Schedule in the Clinic", Poster, AACR-NCI-EORTC Molecular Targets and Cancer Therapeutics, Nov. 18, 2009—Boston, MA.

Freireich, Equivalent Surface Area Dosage Conversion Factors, https://ncifrederick.cancer.gov/Lasp/ Acuc/Frederick/MedialDocuments/ ACUC42. pdf, Aug. 2007.

Friedland et al, "Beyond HER2 and Hormonal Agents: The Heat Shock Protein 90 Inhibitor Ganetespib as a Potential New Breast Cancer Therapy" Poster, 34th Annual CTRC-AACR San Antonio Breast Cancer Symposium, Dec. 8, 2011—San Antonio, TX.

Friedland et al, "Targeted inhibition of Hsp90 by ganetespib is effective across a broad spectrum of breast cancer subtypes", Invest New Drugs, 32:14-24 (2014).

Friedlander., "Treatment od Melanoma Patients with 17 AAG Results in Downregulation of the MAPK Pathway in the Melanoma Tumors" Proc. Amer. Assoc. Cancer Research, 46:(2005).AACR Meeting Abstracts Online.

G. Roue et al., "The Hsp90 inhibitor IPI-504 overcomes bortezomib resistance in mantle cell lymphoma in vitro and in vivo by downregulation of the prosurvival ER chaperone BiP/GRP78", Blood, vol. 177, No. 4, pp. 1270-1279 (2010).

(56) References Cited

OTHER PUBLICATIONS

Galegos Ruiz, M.I., et al; "Integration of Gene Doseage and Gene Expression in Non-Small Cell Lung Cancer Identification of HSP90 as Potential Target" PLOS ONE, 3: 2008.
Gallo, "Targeting Hsp90 to Halt Neurodegeneration", Chem.Bio., Feb. 2006, vol. 13, iss. 2, pp. 115-116.
Ganji et al, "Antiangiogenic effects of ganetespib in colorectal cancer mediated through inhibition of HIF-1a and STAT-3", Angiogenesis, 16:903-917 (2013).
Ganji et al, "Functional Inhibition of HSP90 Potentiates the Effects of Ionizing Radiation in Colorectal Cancer", Poster, 103rd Annual Meeting American Association for Cancer Research (AACR), Mar. 31-Apr. 4, 2012—Chicago, IL.
Gawande, N.G., et al., "Synthesis of Some Thiosemicarbazides and Related Compounds," *Chemistry*, 13(2): 109-111 (1987) XP-002372384.
George, P., et al., "Combination of the Histone Deacetylase Inhibitor LBH589 and the Hsp90 Inhibitor 17-AAG is Highly Active Against Human CML-BC Cells and AML Cells With Activating Mutation of FLT-3," Blood 105(4):1768-1776.
Gerritsen et al, "Current and Emerging Treatment Options; for Castration-Resistant Prostate Cancer: A Focus; on Immunotherapy", J Clin Immul, 32:25-35 (2012).
Girt S, et al.; Asian Journal of Chemistry (1992), 4(4), 812-17.
Giubellino et al, "Targeting Heat Shock Protein 90 for the Treatment of Malignant Pheochromocytoma", PLoS One, 8:1-9 (2013).
Goennert, R., et al., "Constitution and Cestocidal effect in the Yornesan Series," Med. Chern., Abhandl. Med. Chern., Chemical Abstracts Service, Database CA [online] 7:540-567 (1963).
Gogoi, P. C., et al., "Synthesis of 3-(2,4-dichlorophenyI)-4-substituted-5-mercapto-1,2,4-triazoles and their derivatives," *Indian Journal of Chemistry* 298:1143-1145 (Dec. 1990).
Goldman et al, "A first in human, safety, pharmacokinetics, and clinical activity phase I study of once weekly; administration of the Hsp90 inhibitor ganetespib; (STA-9090) in patients with solid malignancies", BMC Cancer, 13:152 (2013).
Goldman et al, "A phase I dose-escalation study of the Hsp90 inhibitor STA-9090 administered once weekly in patients with solid tumors", Poster, The 2010 American Society of Clinical Oncology (ASCO) Annual Meeting, Jun. 4-8, 2010—Chicago, IL.
Goldman, "Phase 2 Study of Ganetespib (STA-9090) in Subjects with Stage IIIB or IV Non-Small Cell Lung Cancer—A Preliminary Report", Presentation, International Association for the Study of Lung Cancer (IASLC) 11th Annual Targeted Therapies for the Treatment of Lung Cancer, Feb. 26, 2011—Santa Monica, CA.
Goldman, L. et al., Cecil's Textbook of Medicine 21 st edition. Published (2000).
Goswami, B. N., "Synthesis and Biological Activity of some O,O-Diethyldithiophosphates/thiophosphates of 3-Substituted-5-mercapto-1,2,4-s-triazoles," *J. Indian Chem. Soc.*, vol. LXIV:422-424 (Jul. 1987).
Goswami, B. N., et al., "Alkylation of thiols using KOH in dimethyl sulphoxide," *Indian Journal of Chemistry* 31B:703-704 (Oct. 1992).
Goswami, B.N., et al., "Synthesis and Antibacterial Activity of 1-(2,4-Dichlorobenzoyl)-4-Substituted Thiosemicarbazides, 1,2,4-Triazoles and Their Methyl Derivatives," Journal of Heterocyclic Chemistry 21(4): 1225-1229 (Jul.-Aug. 1984).
Goswami, B.N., et al., "Synthesis and Antifungal Activities of Some New Substituted 1,2,4-Triazoles and Related Compounds," *Journal of the Indian Chemical Society LXI*(6): 530-533 (1984).
Goyal et al, "A phase I and pharmacokinetic study of ganetespib (STA-9090) in advanced hepatocellular carcinoma." Invest New Drugs pp. 1-10 (2014).
Grashey, R., et al., "Zur Synthese Mesoionischer 1,2,4-Triazol-3-Thione," Tetrahedron Letters 29: 2939-2942 (1972).
Grbovic et al, "V600E B-Raf requires the Hsp90 chaperone for stability and is degraded in response to Hsp90 inhibitors", PNAS, 103:57-62, published online Dec. 21, 2005.
Guzi et al., "Targeting the Replication Checkpoint Using SCH 900776, a Potent and Functionally Selective CHK1 Inhibitor Identified via High Content Screening" Molecular Cancer Therapeutics, vol. 10(4): 591-602, Apr. 1, 2011.
Günay, N.S. et al., "5-Nitroimidazole derivatives as possible antibacterial and antifunal agents," II Farmaco, 54:826-831 (1999).
Hainsworth, et al., J Thor Onc, 2010, 5(10),1630-1636.
Hande, et al., "Topoisomerase II inhibitors," Update on Cancer Therapeutics, 2008; 3(1), 13-26.
Harris, S.F., et al., "The Crystal Structure of the Carboxy-Terminal Dimerization Domain of htpG, the *Escherichia coli* Hsp90, Reveals a Potential Substrate Binding Site," *Structure*, 2004, 12, pp. 1087-1097.
Harvey et al, "A phase 1 and pharmacokinetic study of ganetespib (STA-9090), a heat shock protein 90 inhibitor, in combination with docetaxel in patients with advanced solid tumor malignancies", Poster, The European Multidisciplinary Cancer Congress, Sep. 26, 2011—Stockholm, Sweden.
He et al, "Inhibition of mTOR enhances the activity of HSP90 inhibitors in part through cessation of heat shock protein synthesis", Poster, The 2013 Annual Meeting of the American Association of Cancer Research (AACR), Apr. 6-10, 2013—Washington D.C.
He et al, Multi-Targeted Activity of the Hsp90 Inhibitor Ganetespib (STA-9090) in Prostate Cancer Cells, Poster, The Endocrine Society's 93rd Annual Meeting & Expo 2011, Jun. 5, 2011—Boston, MA.
He et al, "Potent activity of the Hsp90 inhibitor ganetespib in prostate cancer cells irrespective of androgen receptor status or variant receptor expression", Int J Oncology, 42:35-43 (2013).
He et al, "The HSP90 inhibitor ganetespib has chemosensitizer and radiosensitizer activity in colorectal cancer models", Poster, 105th Annual Meeting of the American Association for Cancer Research, Apr. 5-9, 2014—San Diego, CA.
He et al, "The HSP90 inhibitor ganetespib has chemosensitizer and radiosensitizer activity in colorectal cancer", Invest New Drugs, 32:577-586 (2014).
Health et al, "Phase II Trial of Ganetespib (STA-9090), a Heat Shock Protein (Hsp90) Inhibitor in Patients with Metastatic Castration-Resistant Prostate Cancer (CRPC) Pretreated with Docetaxel-Based Chemotherapy; a Prostate Cancer Clinical Trials Consortium (PCCTC) Study", The 2013 American Society of Clinical Oncology (ASCO) Annual Meeting, May 31-Jun. 4, 2013—Chicago, IL.
http://info.cancerresearchuk.org/healthyliving/introducingcancerprevention/.
http://www.cancer.gov/cancertopics/types/alphalist/y.
http://www.merriam-webster.com/dictionary/prevent.
Huanjie Yang et al., "Clinical development of novel proteasome inhibitors for cancer treatment", Expert Opinion on Investigational Drugs, Informa Healthcare, United Kingdon, vol. 18, No. 7, pp. 957-971 (2009).
Husain, S., et al., "3,4-Distributed 5-Hydroxy-1,2,4-triazoles Derived from 4-Substituted Semicarbazones," Indian Journal of Chemistry, 9: 642-646 (1971).
Ikizler, A., and Un, R., "Reactions of Ester Ethoxycarbonylhydrazones With Some Amine Type Compounds," *Chimica Acta Turcica*, 7: 269-290 (1979).
Ikizler, A., et al., "Biological Activities of Some 1,2,4-triazoles and 1,2,4-triazolin-5-ones," Die Pharmazie, 44(7): 506-507 (1989).
Ikizler, A., et al., "Synthesis of some New N,N'-Linked Biheteroaryls," *Polish Journal of Chemistry*, 69:1497-1502 (1995).
Ikizler, A.A and Yuksek, H., "A Study on 4,5-Dihydro-1H-1,2,4-Triazol-5-Ones," Revue Roumaine de Chimie, 41(7-8): 585-590 (1996).
Ikizler, A.A. and Yuksek, H., "Synthesis of 3-Alkyl-4-(2-Hydroxyethyl)- and 3-Alkyl-4-(2-Chloroethyl)-4,5-Dihydro-1H-1,2,4-Triazol-5-Ones," Turkish Journal of Chemistry, 16(4): 284-288 (1992).
Ikizler, A.A. and Yuksek, H., "Acetylation of 4-Amino-4,5-Dihydro-1H-1,2,4-Triazol-5-Ones," Organic Preparations and Procedures Int., 25(1): 99-105 (1993).
Ikizler, A.A. et al., "Susuz Ortamda Bazi 1, 2, 4-Triazol Ve 1, 2, 4-Triazolin-5-on Türevlerinin pKa Degerlerinin Hesaplanmasi," Turkish Journal of Chemistry, 12(1):57-66 (1988).

(56) References Cited

OTHER PUBLICATIONS

Ikizler, A.A. et al., "Synthesis and Biological Activities of Some 4,5-Dihydro-1H-1,2,4-Triazol-5-One Derivatives," *Acta Poloniae Pharmaceuticals—Drug Research*, 55(2) 117-123 (1998).

Ikizler, A.A. et al., "Ultraviolet Spectra of Some 1, 2, 4-Triazole Derivatives," J. of Chemistry, 16:164-170 (1992).

Infante et al. A Phase I Dose-Escalation Study of The Oral Heat Shock Protein 90 Inhibitor PF-04929113 (SNX5422) and Its Associated Ocular Toxicity; Presented at the 22nd EORTC-NCI-AACR Symposium on Molecular Targets and Cancer Therapeutics, Berlin, Germany, Nov. 16-19, 2010. downloaded from http://www.hsp90central.com.

Iorga, T. et al., "Studial Activit ii Biologice a unor Noi Tiosemicarbazide i a Deriva ilor Acestora cu Nucleu Triazolic i Tiadiazolic I. Testarea Toxicit ii," Farmacia, XXVIII(2): 103-114 (1980).

Jez, J., et ai., "Crystal Structure and Molecular Modeling of 17-DMAG in Complex with Human Hsp90," *Chemistry & Biology*, 2003, 10, pp. 361-368.

Jhaveri et al, "A Phase I Clinical Trial of Ganetespib (Heat shock protein 90 inhibitor) in Combination with Paclitaxel and Trastuzumab in Human Epidermal Growth Factor Receptor-2 Positive (HER2+) Metastatic Breast Cancer", Poster, San Antonio Breast Cancer Symposium, Dec. 9-13, 2014—San Antonio, TX.

Jhaveri et al, A Phase II Open-Label Study of Ganetespib, a; Novel Heat Shock Protein 90 Inhibitor for Patients With Metastatic Breast Cancer, Clin Breast Cancer, 14:154-160 (2014).

Jhaveri et al, A Phase II trial of Ganetespib: Efficacy and safety in patients (pts) with metastatic breast cancer (MBC), Poster, 34th Annual CTRC-AACR San Antonio Breast Cancer Symposium, Dec. 7, 2011—San Antonio, TX.

Ji. H., et al: "Mutations in BRAF and KRAS Converge on Activation of the Mitogen-Activated Protein Kinase Pathway in Lung Cancer Mouse Model" Cancer Research 67: 4933-4939, 2007.

Johnson J. R. et al.: "Approval summary for erlotinib for treatment of patients with locally advanced or metastatic non-small cell lung cancer after failure of at least one prior chemotherapy regimen", Clinical Cancer Research 20050915 US LNKD-DOI: 10.1158/1078-0432.CCR-05-0790, vol. 11, No. 18, Sep. 15, 2005 (Sep. 15, 2005), pp. 6414-6421.

Kabakov et al., Hsp90 inhibitors as promising agents for radiotherapy, Journal of Molecular Medicine, vol. 8, No. 33, pp. 241-247 (2009).

Katayama et al: "Therapeutic strategies to overcome crizotinib resistance in non-small cell lung cancers harboring the fusion oncogene EML4-ALK", Proceedings of the National Academy of Sciences, National Academy of Sciences, US, vol. 1 08, No. 18,May 3, 2011, pp. 7535-7540.

Kauh et al, "A phase 1 dose escalation study of ganetespib (STA-9090), a heat shock protein 90 inhibitor, in combination with docetaxel in patients with advanced solid tumors", Poster, The 2012 American Society of Clinical Oncology (ASCO) Annual Meeting, Jun. 1-5, 2012—Chicago, IL.

Khan, et al., Indian Journal of Chemistry, Section B: Organic Chemistry including Medicinal Chemistry (1998) 37B, 1075-1077.

Kihana, et al.,: "High incidence of p53 gene mutation in human ovarian cancer and its association with nuclear accumulation of p53 protein and tumor DNA aneuploidy", Japanese Journal of Cancer Research, vol. 83, No. 9, (1992), pp. 978-984.

Kreusch et al, "Crystal Structures of Human HSP90α-Complexed With Dihydroxyphenylpyrazoles," *Bioorganic & Medicinal Chemistry Letters*, 15:1475-1478 (2005).

Kwak et al, A Phase II Clinical Trial of Ganetespib (STA-9090) in Previously Treated Patients with Advanced Esophagogastric Cancer, Poster, The 2013 American Society of Clinical Oncology (ASCO) Annual Meeting, May 31-Jun. 4, 2013—Chicago, IL.

Labanauskas, L., et al., "Synthesis of 5-(2-,3- and 4-Methoxyphenyl)-4H-1,2,4-Triazole-3-Thiol Derivatives Exhibiting Anti-Inflammatory Activity," II Farmaco, 59: 255-259 (2004).

Lancet Jeffrey E et al. "A Phase I/II Trial of the Potent Hsp90 Inhibitor STA-9090 Administered Once Weekly in Patients with Advanced Hematologic Malignancies", Blood, vol. 116, No. 21, Nov. 2010 (Nov. 2010), pp. 1349-1350 & 52nd Annual Meeting of the American-Society-of-Hematology (ASH); Orlando, FL, USA; Dec. 4 -7, 2010.

Lancet, "A Phase ½ Study of the Potent Hsp90 Inhibitor STA-9090 Administered Once Weekly in Subjects with Hematologic Malignancies", Poster, American Society of Hematology, Dec. 6, 2010—Orlando, FL.

Lang et al., "Targeting heat-shock protein 90 improves efficacy of rapamycin in a model of hepatocellular carcinoma in mice", Hepatology, vol. 49, No. 2, pp. 523-532 (2009).

Lanie et al., "Combination mammalian target of rapamycin and HSP90 inhibitor rapamycin and HSP90 inhibitor 17-allylamino-17demethoxygeldanamycin has synergistic activity in multiple myeloma", Clinical Cancer Research, The American Association for Cancer Research, US, vol. 12, No. 22, pp. 6826-6835 (2006).

Lavictoire, S.J., et al., "Interaction of Hsp90 With the Nascent Form of the Mutant Epidermal Growth Factor Receptor EGFRvIII," J. Biological Chemistry 278(7):5292-5299 (Feb. 14, 2003).

Leaf, Fortune, 2004, Time Inc., pp. 1-13.

Lee et al, "Differential sensitivities to heat shock protein 90 (HSP90) inhibitors in anaplastic lymphoma kinase (ALK)-positive non-small cell lung cancer (NSCLC) cells", Poster, The 2013 Annual Meeting of the American Association of Cancer Research (AACR), Apr. 6-10, 2013—Washington D.C.

Lee et al,"Mechanism(s) of action and potency of Hsp90 inhibitor ganetespib in small cell lung carcinoma cells", Poster, IASLC 14th World Conference on Lung Cancer, Jul. 5, 2011 Amsterdam, The Netherlands.

Lee, A.Y., et al., "Late relapse in patients with diffuse large-cell lymphoma treated with MACOP-B," *J. Clin. Oncol.* 15(5):1745-1753 (1997).

Li et al, "Erlotinib Effectively Inhibits JAK2V617F Activity and Polycythemia Vera Cell Growth", J Biol Chem, 282(6): 3428-3432 (2007).

Li et al: "Radiation/Paclitaxel Treatment of p53-Abnormal Non-Small Cell Lung Cancer Xenograft Tumor and Associated Mechanism", Cancer Biotherapy & Radiopharmaceuticals, vol. 27, No. 4, 2012, pp. 227-233.

Li Y et al., "New developments in Hsp90 inhibitors as anti-cancer therapeutics: Mechanisms, clinical perspective and more potential", Drug Resistance Updates, Churchill Livingstone, Edinburgh, GB, vol. 12, No. 1-2, pp. 17-27 (2009).

Lin et al, "Heat shock protein 90 inhibition limits the emergence of tamoxifen resistance", Poster, San Antonio Breast Cancer Symposium, Dec. 12, 2010—San Antonio, TX.

Lin et al, "The novel HSP90 inhibitor STA-9090 exhibits activity against Kit dependent and independent malignant mast cell tumors", Abstract, 99th AACR Annual Meeting, Apr. 12-16, 2008; San Diego, CA.

Lin et al, "The novel HSP90 inhibitor STA-9090 exhibits activity against Kit-dependent and -independent malignant mast cell tumors", Exp Hematol, 36:1266-1277 (2008).

Liu et al, "Network Analysis Identifies an HSP90-Central Hub; Susceptible in Ovarian Cancer", Clin Cancer Res, 19:5053-5067 (2013).

Lixue, Z., et al., "Studies on Acylthiosemicarbazides and Related Heterocyclic Derivatives," *Chemical Journal of Chinese Universities* 11(2): 148-153 ( 990).

London et al, "Phase I evaluation of STA-1474, a pro-drug of the novel HSP90 inhibitor ganetespib (formerly STA-9090), in dogs with spontaneous cancer", Poster, 102nd AACR Annual Meeting, Apr. 4, 2011—Orlando, FL.

London et al,"The importance of dose schedule with Hsp90 inhibitors: Results from a Phase II study in dogs with mast cell tumors", Poster, The 2013 Annual Meeting of the American Association of Cancer Research (AACR), Apr. 6-10, 2013—Washington D.C.

London et al., "Phase I Evaluation of STA-1474, a Prodrug of the Novel HSP90 Inhibitor Ganetespib, in Dogs with Spontaneous Cancer", PLOS ONE, vol. 6, No. 11, p. e27018 (2011).

(56) References Cited

OTHER PUBLICATIONS

Lu Kuaike, et al., "Synthesis and anti-tumor activities of 4β-S-(5"-alkyl-4"-amino-1",2"-,4"-triazole-3"-yl)-4-deoxy-4'-o-demethyl-epipodophyllotoxin derivatives", Acta Pharmaceutia Sinica, 1999, 34(1), pp. 63-66.
Mahaseth et al, "Antiangiogenic Effects Associated with the Inhibition of HSP90 in Colorectal Cancer", Poster, 103rd Annual Meeting American Association for Cancer Research (AACR), Mar. 31-Apr. 4, 2012—Chicago, IL.
Malbec, F., et al., "Derives de la Dihydro-2,4 Triazole-1,2,4 Thione-3 et de 1-amino-2 Thiadiazole-1,3,4 a Partir de Nouvelles Thiosemicarbazones d'esters," Journal of Heterocyclic Chemistry 21(6): 1689-1698 (Nov.-Dec. 1984).
Maliszewska, A., "The Reaction of N3-Substituted Amidrazones with Urea," Annales Universitatis Mariae Curie-Sklodowska Lublin-Polonia, vol. XLI, 5, Sectio AA:63-67 (1986).
Mansfield, Ten-Year Results in 1070 Patients with Stages I and II Breast Cancer Treated by Conservative Surgery and Radiation Therapy, Cancer, 1995, 75(9), pp. 2328-2336.
Marubayashi et el., "Hsp90 is a therapeutic target in JAK2-dependent myeloproliferative neoplasms in mice and humans", The Journal of Clinical Investigation, vol. 120, No. 10, pp. 3578-3593 (2010).
Mazzone, et al., "Cyclic Derivatives from Alkoxybenzohydrazides. Synthesis of Pyrazoles, Pyrroles and Triazol-5-Ones of Pharmaceutical Interest," Eur. J. Med. Chem.--Chim. Ther., 21(4): 277-284 (1986).
McCleese et al, "The novel HSP90 inhibitor STA-12-1474 exhibits biologic activity against canine osteosarcoma cell lines", Abstract, 99th AACR Annual Meeting—Apr. 12-16, 2008; San Diego, CA.
McNamara A, Potentiation of Topoisomerase I inhibitors by Hsp90 inhibitors: Mechanistic and Functional studies. British Library EThOS, 2007 University of Liverpool. Retrieved from the Internet: URL:http://ethos.bl.uk/OrderDetails.do?uin=uk.bl.ethos.485908 [retrieved on Dec. 5, 2012].
Mcnamara AV, et al., Identification and characterisation of proteins interacting with eukaryotic DNA topoisomerase I. Gut, vol. 54, p. A34 (2005).
Mendillo et al, "Cancer chemotherapy: An unfolding story", Abstract, The 6th International Symposium on Heat Shock Proteins in Biology and Medicine, Nov. 3-7, 2012—Washington D.C.
Milcent, R. and Redeuilh, C., "Recherche en Serie du Triazole-1,2,4. II--Reactivite des Amino-4 Aryl-3 Triazp;-1,2,4 Ones-5," Journal of Heterocyclic Chemistry, 17(8): 1691-1696 (1980).
Milcent, R., and Vicart, P., "Synthèse Et Activité*Antibacterienne D'amino-4 Triazol-1,2,4 Ones-5 Substituèes*," Eur. J. Med. Chem. - Chim. Ther., 18(3): 215-220 (1983).
Mitchell et al., "In vitro and In vivo Radiation Sensitization of Human Tumor Cells by a Novel Checkpoint Kinase Inhibitor, AZD7762", Clinical Cancer Research, vol. 16, No. 7, pp. 2076-2084 (2010).
Mitsiades et al., "HSP90 Molecular Chaperone: a Novel therapeutic Target for B-Cell Lymphomas and Multiple Myeloma," 13 (Suppl. 2):168, abstract #612 (2002).
Modzelewska, B., "Cyclization Reaction of Thiosemicarbazone-4-Picolinamide Derivatives," Acta Poloniac Pharmaceutica-Drug Research, 52(5):425-427 (1995).
Modzelewska, B., "On the Reaction of Cyclization of p-Phenyleno-bis-(-N3-2- pikolinamidrazonu)," Annales Universitatis Mariae Curie-Sklodowska Lublin-Polonia, vol. XLVI/XLVII, 10, Sectio AA:61-66 (1991/1992).
Modzelewska, B., "Studies on the Reaction of N3-Substituted Amidrazones with Metoxycarbonylethyl Isothiocyanate Part I," *Annales Universitatis Mariae Curie-Sklodowska Lublin-Polonia*, vol. XLI (3): 45-52 (1986).
Modzelewska, B., "Studies on the Reaction of N3-Substituted Amidrazones with Metoxycarbonylethyl Isothiocyanate Part II," *Annales Universitatis Mariae Curie-Sklodowska Lublin-Polonia*, vol. XLI (4): 53-61 (1986).

Modzelewska, B., "Studies on the Reaction of N3-Substituted Amidrazones with Metoxycarbonylethyl Isothatcyanate Part II," Annales Universitatis Mariae Curie-Sklodowska Lublin-Polonia, vol. XLI 5: 63-67 (1986).
Modzelewska, B., and Maliszewska, A., "The Reaction of N3-substituted Amidrazones with the Aromatic Izothiocyanates, Part III," vol. XXXIXIXL, 13: 163-170 (1985).
Modzelewska-Banachiewicz, B., et al., "Synthesis and Biological Activity of BIS-1, 2, 4-Triazole and BIS-1, 3, 4-Thiadiazole Derivatives," *Acta Poloniac Pharmaceutica Drug Research*, 57(3): 199-204 (2000).
Morissette et al. Adv. Drug Delivery Rev. 56:275 (2004).
Nagaraju et al, "Antiangiogenic activity of the HSP90 inhibitor ganetespib in pancreatic cancer models", Poster, Experimental Biology 2013, Apr. 20-24, 2013—Boston, MA.
Nagaraju et al, "Heat Shock Protein 90 Functional Inhibition Regulates Epithelial to Mesenchymal Transformation, Invasion and Migration via NF-κB and HIF-1α Signaling in Colorectal Cancer,", Poster, The 2013 Annual Meeting of the American Association of Cancer Research (AACR), Apr. 6-10, 2013—Washington D.C.
Nagaraju et al, "Heat Shock Protein 90 Promotes Epithelial; to Mesenchymal Transition, Invasion, and Migration in Colorectal Cancer", Mol Carcinog (2014).
Nagourney Robert A et al: "Geldenamycin and 17-allylamino-17—demethoxygeldenamycin alone and in combination with cytotoxic drugs in human tumor primary cultures.", Proceedings of The American Association for Cancer Research Annual Meeting, 2005, 46, p. 404, & 96th Annual Meeting of The American-Association-For-Cancer-Research; Anaheim, CA, USA; April 16 -20, 2005.
Nakatani, H., et al., "STI571 (Glivec) Inhibits the Interaction Between c-KIT and Heat Shock Protein 90 of the Gastrointestinal Stromal Tumor Cell Line, GIST-T1," Cancer Sci 96(2):116-119 (Feb. 2005).
National Cancer Institute. Understanding Cancer Series: What is Tumor Angiogenesis. Jan. 28, 2005.http://www.cancer.gov/cancertopics/understandingcancer/angiogenesis/Slide-3.
Neckers., "Heat Shock Protein 90: the Cancer Chaperone," J of Biosci, 32(3) Apr. 2007, pp. 517-530.
Nehs, M.A., et al., PLX4720 Induces Tumor Regression, Reverses Cachexia, and Extends Survival in a Mouse Model of Late-Stage Anaplastic Thyroid Cancer, Journal of the American College of Surgeons, College, Chicago, IL, 211(3):S124: Sep. 1, 2010.
Neidle, Cancer Drug Design and Discovery, Elsevier/Academic Press, 2008, pp. 427-431.
Nguyen, D M et al: "Modulation of Metastasis Phenotypes of Non-Small Cell Lung Cancer Cells by 17-Allylamino 17-Demethosy Geldanamycin" The Annals of Thoracic Surgery, 70: 1853-1860, 2000.
Noguchi et al., "Inhibition of homologous recombination repair in irradiated tumor cells pretreated with Hsp90 inhibitor 17-allylamino-17-demethoxygelda namycin", BioChemical and Biophysical Research Communications, vol. 352, No. 3, pp. 658-663 (2006).
Nwizu T et al: "Crizotinib ALK/Met inhibitor Oncolytic", Drugs of the Future, Prous Science, ES, vol. 36, No. 2, Feb. 1, 2011, pp. 91-99.
Ogura, et al., "Studies on Nucleoside Analogs. XXI. A Convenient Synthesis of 1,2,4-triazole-5-thione glycosides", Chemical and Pharmaceutical Bulletin 29(8), 2188-92 (1981).
Padmanabhan et al, "A Phase I Study of the Potent Hsp90 Inhibitor STA-9090 Administered Twice Weekly in Subjects with Hematologic Malignancies", Poster, American Society of Hematology, Dec. 5, 2010—Orlando, FL.
Padmanabhan et al, "Hsp90 Inhibitor STA-9090 Downregulates Expression of Hsp90 Client Protein WT1 in Myeloid Leukemia Cells", Poster, Hematologic Malignancies: Bridging the Gap 2010, Feb. 5-7, 2010—Singapore City, Singapore.
Paraiso, Kim H.T., et al., The HSP90 Inhibitor XL888 Overcomes BRAF Inhibitor Resistance Mediated through Diverse Mechanisms, Clinical Cancer Research, 18(9):2502-2514, May 2012.
Parasramka et al, "Preclinical activity of the heat shock protein 90 (hsp90) inhibitor ganetespib in clear cell renal cell (ccRCC)", Poster, 2014 Genitourinary Cancers Symposium, Jan. 30-Feb. 1, 2014—San Francisco, CA.

(56) References Cited

OTHER PUBLICATIONS

Pashtan I. et al.: "Targeting Hsp90 prevents escape of breast cancer cells from tyrosine kinase inhibition", Cell Cycle 20080915 US, vol. 7, No. 18, Sep. 15, 2008 (Sep. 15, 2008), pp. 2936-2941.
Patani, et al., Chem. Rev., 1996, 96, pp. 3147-3176.
Patel et al, "Heat shock protein 90 (HSP90) inhibition in squamous cell carcinoma of the head and neck (SCCHN): an in vitro analysis with a focus on p16 status", Poster, The 2013 American Society of Clinical Oncology (ASCO) Annual Meeting, May 31-Jun. 4, 2013—Chicago, IL.
Petricoin et al, "Gene Expression and Proteomic Analysis to Identify Predictive Biomarkers of Response in the ENCHANT-1 Trial (NCT01677455), a Phase 2 Proof of Concept Study Evaluating First-Line Ganetespib Monotherapy in Women with Metastatic HER2 Positive or Triple Negative Breast Cancer (TNBC)", Poster, 105th Annual Meeting of the American Association for Cancer Research, Apr. 5-9, 2014—San Diego, CA.
Pommier Y, et al., DNA Topoisomerases and Their Poisoning by Anticancer and Antibacterial Drugs. Chemistry & Biology, vol. 17(5), pp. 421-433 (2010).
Pommier Y, Topoisomerase I inhibitors: Camptothecins and beyond. Nature Reviews Cancer. vol. 6(10) pp. 789-802, (2006).
Potts, K.T., "meso Ionic Compounds. II. Derivatives of the s-Triazole Series," *The Journal of Organic Chemistry*, 32(7): 2245-2252 (1967).
Powers et al, "Targeting of mutiple signalling pathways by heat shock protein 90 molecular chaperone inhibitors", Endocr Relat Cancer, 13:S125-S135 (2006).
Premkumar Daniel R. et al.: "Cooperative inhibitory effect of ZD1839 (Iressa) in combination with 17-AAG on glioma cell growth", Molecular Carcinogenesis, vol. 45, No. 5, May 2006 (May 2006), pp. 288-301.
Premkumar et al., "Synergistic interaction between 17-AAG and phosphatidylinositol 3-kinase inhibition in human malignant glioma cells", Molecular Carcinogenesis, vol. 45, No. 1, pp. 47-59 (2006).
Prodromou, C., et al., "Identification and Structural Characterization of the ATP/ADP-Binding Site in the Hsp90 Molecular Chaperone," *Cell*, 1997, 90, pp. 65-75.
Proia D. et al., "Preclinical activity of the Hsp90 inhibitor, ganetespib, in ALK- and ROS1-driven cancers.", American Society of Cancer Oncology Annual Meeting, Jun. 1-5, 2012 (abstract).
Proia et al, "Anti-metastatic activity, chemotherapeutic enhancement and therapeutic potential of targeting Hsp90 with ganetespib in triple negative breast cancer", Poster, San Antonio Breast Cancer Symposium, Dec. 10-14, 2013—San Antonio, TX.
Proia et al, "Antimetastatic activity of ganetespib: preclinical studies and assessment of new lesion growth in the GALAXY-1 NSCLC trial", Poster, 15th World Conference on Lung Cancer, Oct. 27-30, 2013—Sydney, Australia.
Proia et al, "Antimetastatic activity of ganetespib: preclinical studies and assessment of progressions due to new lesions in the GALAXY-1 NSCLC trial", Poster, European Cancer Congress 2013 (ECCO-ESMO-ESTRO), Sep. 27-Oct. 1, 2013—Amsterdam, The Netherlands.
Proia et al, "Combination of the Hsp90 Inhibitor Ganetespib (STA-9090) With Docetaxel Displays Synergistic Anticancer Activity in Solid Tumor Cells", Poster, 9th International Symposium on Targeted Anticancer Therapies, Mar. 7-9, 2011—Paris, France.
Proia et al, "Ganetespib and HSP90: Translating Preclinical Hypotheses into Clinical Promise", Cancer Res, 74:1294-1300 (2014).
Proia et al, "Multifaceted Intervention by the Hsp90 Inhibitor Ganetespib (STA-9090) in Cancer Cells with Activated JAK/STAT Signaling", PLoS ONE, 14:e18552 (2011).
Proia et al, "Multimodal Action of the Hsp90 Inhibitor STA-9090 in Treating Cancer Cells With Activated JAK/STAT Signaling", Poster, 101st AACR Annual Meeting, Apr. 19, 2010 Washington, DC.
Proia et al, "Preclinical activity of the Hsp90 inhibitor, ganetespib, in ALK- and ROS1-driven cancers", Poster, The 2012 American Society of Clinical Oncology (ASCO) Annual Meeting, Jun. 1-5, 2012—Chicago, IL.
Proia et al, "Preclinical Activity Profile and Therapeutic Efficacy of the HSP90 Inhibitor Ganetespib in Triple-Negative; Breast Cancer", Clin Cancer Res, 20:413-424 (2013).
Proia et al, "Synergistic activity of the Hsp90 inhibitor ganetespib with taxanes in non-small cell lung cancer models", Invest New Drugs, 30:2201-2209 (2012).
Ramazani, A. et al., "Crystal structure of 4-[4-(dimethylamino)phenyl]-5-(2, 4-dimethyl-1, 3- thiazol-yl)-2, 4-dihydro-3H-1, 2, 4-triazol-3-thione, C15H17N552," K. Kristallogr, NCS, 217:149-150 (2002).
Ravi, T.K. & Rajkannan, R., "Synthesis and antimicrobial Activity of Some New 1,2,4-Triazoles," *Indian J. of Pharmaceutical Sciences*, 66(3), 347-350 (2004).
Reichert et al, "Ganetespib: An effective strategy to overcome crizotinib resistance in ALK- driven cancers", Poster, 3rd European Lung Cancer Conference (IASLC/ESMO), Apr. 18-21, 2012—Geneva, Switzerland.
Rice J.W. et al.: "Targeting of multiple signaling pathways by the Hsp90 inhibitor SNX-2112 in EGFR resistance models as a single agent or in combination with erlotinib", Oncology Research 2009 Cognizant Communication Corporation USA Lnkd-DOI: 10.3727/096504009X12596189659240, vol. 18, No. 5-6, 2009, pp. 229-242, XP009148484.
Rich et. al., Nature Reviews, 2004, Nature Publishing Group, vol. 3, pp. 430-446.
Robertus, et al., Toxicon, 1996, 34:1325-1334.
Romine, et al., "4,5-Diphenyltriazol-3-ones: Openers of large-conductance Ca2+-activated potassium (Maxi-K) channels," *J. Med. Chem*. (2002), 45:2942-2952.
Rostom, S.A.F., et al., "Polysubstituted Pyrazoles, Part 5. Synthesis of new 1-(4-Chlorophenyl)-4-Hydroxy-1H-Pyrazole-3-Carboxylic Acid Hydrazide Analogs and Some Derived Ring Systems. A Novel Class of Potential Antitumor and Anti-HCV Agents,"European J Med Chem, 38:959-974 (2003).
Rouhi, Chem. & Eng. News, Feb. 24, 2003, 81(8), 32-35.
Russo, et al., "Derivati Benzotiazolici del 1,2,4-triazolo," *Annali di Chimica*, 62: 351-372 (1972).
Samanta et al., Destabilization of Bcr-Abl/Jak2 Network by a Jak2/Abl Kinase Inhibitor 0N044580 Overcomes Drug Resistance in Blast Crisis Chronic Myelogenous Leukemia, Genes and Cancer, vol. 1, No. 4, pp. 346-359 (2010).
Sang et al, "Novel Hsp90 Inhibitor, Ganetespib (STA-9090), for Combination With Radiotherapy", Poster, 102nd AACR Annual Meeting, Apr. 4, 2011—Orlando, FL.
Sang et al, "Targeted Inhibition of the Molecular Chaperone Hsp90 Overcomes ALK Inhibitor Resistance in Non-Small Cell Lung Cancer," Cancer Discov, 3:430-443 (2013).
Sawai Ayana et al: "Inhibition of Hsp90 down-regulates mutant epidermal growth factor receptor (EGFR) expression and sensitizes EGFR mutant tumors to paclitaxel", Cancer Research, . 2008, 68(2), pp. 589-596.
Sawhney, et al., "Synthesis and Anti-inflammatory Activity of Some 3-Heterocyclyl-1,2-Benzisothiazoles," Indian J. of Chem., 32B, 1190-1195 (1993).
Sawhney, et al., "Synthesis of Some 2-(5-Substituted 1,3,4-Oxadiazol-2-Yl)-, 2-(5-Substituted 1,3,4-Thiadiazol-2-Yl)- and 2-(3-Mercapto-4-Substituted-4H-1,2,4-Triazol-5-Yl)-Benzimidazoles as Potential Anti-Inflammatory Agents," Indian J. of Chem.,30B:407-412 (1991).
Schag, et al., "Identification of C-Met Oncogene as a Broadly Expressed Tumor-Associated Antigen Recognized by Cytotoxic T-Lymphocytes", Clinical Cancer Research, 2004, vol. 10, pp. 3658-3666.
Schoof et al., "Hsp90 is essential for Jak-STAT signaling in classical Hodgkin lymphoma cells', Cell Communication and Signaling", vol. 7, No. 1, p. 17 (2009).
Seeger-Nukpezah et al, "Inhibiting the HSP90 chaperone slows cyst growth in a mouse model of autosomal dominant polycystic kidney disease", PNAS, 110:12786-12791 (2013).
Seike et. al., Cancer Letters, 2003, Elsevier, vol. 192, pp. 25-36.
Sen, et al., Indian Journal of Heterocyclic Chemistry (2005) 14(3), 269-270.
Senthilvelan, A. et al., "Photodesulfurization of 2, 4-Diaryl-1, 2, 4-Triazole-3-Thiones," *Heteroatom Chemistry*, 14(3):269-272 (2003).

(56) References Cited

OTHER PUBLICATIONS

Sequist et al., "Association between Anaplastic Lymphoma reearrangements (rALK) and the clininal activity of IPI-504 (retaspimycin hydrochloride), a novel Hso90 inhibitor, inpatients with non-small cell lung cancer (NSCLC)", ASCO Annual Meeting, Abstract, Jun. 4-8, 2010.
Serra et al., "NVP-BEZ235, a Dual Pl3K/mTOR Inhibitor, Prevents PI3K Signaling and Inhibits the Growth of Cancer Cells with Activating PI3K Mutations", Cancer Research, vol. 68, No. 19, pp. 8022-8030 (2008).
Shafi et al, "Differential Responsiveness of Androgen Receptor Splice Variants to Regulators of Androgen Receptor Action", Poster, The Endocrine Society's 94th Annual Meeting & Expo, Jun. 24, 2012—Houston, TX.
Shah, et al., "3,4-Disubstituted-5-carboxymethylthio-4H-1,2,4-triazoles as possible antiviral agents," Indian J. Chem 5:391-393 (1967).
Shapiro, "HSP90 Inhibitors in Clinical Development: STA-9090 (ganetespib)", Presentation, 9th International Symposium on Targeted Anticancer Therapies, Mar. 7-9, 2011—Paris, France.
Shapiro, "STA-9090 A Potent 2nd Generation Hsp90 Inhibitor", 10th Annual Targeted Therapies of Lung Cancer Meeting, Presentation, Feb. 25, 2010—Santa Monica, CA.
Shapiro: "Phase II study of the Hsp90 inhibitor ganetespib as monotherapy in patients with advanced NSCLC", Internet-U-Tube, Jun. 2011, Retrievedfrom the Internet: URL:http//www.youtube.com/watch?v=UX8fEZbF1bk.
Shaw et al, Clin Cancer Res; 17(8) Apr. 15, 2011.
Shepherd, FA et al., New England Journal of Medicine vol. 353, pp. 123-132. Published 2005.
Shimamura et al, "The novel Hsp90 inhibitor STA-9090 has potent anticancer activity in in vitro and in vivo models of lung cancer", Poster, 100th AACR Annual Meeting, Apr. 21, 2009—Denver, CO.
Shimamura et al,"Ganetespib (STA-9090), a Non-Geldanamycin HSP90 Inhibitor,has Potent Antitumor Activity in In Vitro and In Vivo Models of Non-Small Cell Lung Cancer", Clin Cancer Res, 18:4973-4985 (2012).
Shimamura, T., et al.: "Hsp90 Inhibition Suppresses Mutant EGFR-T790M Signaling and Overcomes Kinase Inhibitor Resistance" Cancer Research, 68: 5827-5838, 2008.
Shinmamura, T. et al., "The novel Hsp90 inhibitor STA-9090 has potent anticancer activity in in vitro and in vivo models of lung cancer", 100th AACR Annual Meeting, Apr. 18-21, p. 4679, 2009 (abstract). XP055067116.
Siavash, H. et al., Critical Reviews in Oral Biology & Medicine, 15(5):298-307(2004).
Silverman, R.B., The Org. Chem. of Drug Design and Drug Action, Academic Press, Inc.: San Diego, 1992, pp. 4-51.
Smith et al, "The HSP90 inhibitor ganetespib potentiates the antitumor activity of EGFR tyrosine kinase inhibition in mutant and wild-type non-small cell lung cancer", Targ Oncol (2014).
Smith, et al., "Preclinical pharmacokinetics and metabolism of a novel diaryl pyrazole resorcinol series of heat shock protein 90 inhibitors," *Mol. Cancer Ther.* (2006), 6(6):1628-1637.
Socinski et al, "A Multicenter Phase II Study of Ganetespib Monotherapy in Patients with Genotypically Defined Advanced Non-Small Cell Lung Cancer", Clin Cancer Res, 19 (2013).
Solit D, Egorin MJ, Valentin G, et al. Phase 1 pharmacokinetic and pharmacodynamic trial of docetaxel and 17-AAG (17-allylamino-17-demethoxygeldanamcyin) [abstract 3032]. Proceedings of the American Society of Clinical Oncology 2004, 23: 203.
Sonar, et al., "Synthesis and Antimicrobial Activity of Triazolylindoles and Indolylthiazolidinones," *Indian J. of Heterocyclic Chem.*, 5: 269-271 (1996).
Soni, N., et al., "Analgesic Activity and Monoamine Oxidase Inhibitory Property of Substituted Mercapto 1,2,4-Triazoles," *Eur. J. Med. Chem.*, 20(2): 190-192 (1985).
Sos M.L., et al.: "Predicting Drug susceptability of non-small cell lung cancers based on genetic lesions" The Journal of Clinical Investigation, 119: 1727-1740, 2009.

Stebbins, C.E., et al., "Crystal Structure of an Hsp90-Geldanamycin Complex: Targeting of a Protein Chaperone by an Antitumor Agent," *Cell, 1997* 89, pp. 239-250.
Stinchcombe et. al., Oncogene, 2007, Nature Publishing Group, vol. 26, pp. 3691-3698.
STN registry data for STA-9090 (2006).
Stoeltzing et al., "59 Dual targeting of mTOR and HSP90 for therapy of pancreato-biliary carcinomas", European Journal of Cancer, vol. 8, No. 7, p. 27 (2010).
Surh, Nature Reviews Cancer, 2003, Nature Publishing Group, vol. 3, pp. 768-780.
Swigris et. al., Chest, 2005, American College of Chest Physicians, vol. 127, pp. 275-283.
Synta Press Release: Synta Presents Results at AACR-IASLC Demonstrating Potent and Synergistic Activity of STA-9090 in NSCLC Cell Lines Including Mutated EGFR, HER2, and KRAS, Jan. 12, 2010.
Tandon, M., et al., "Synthesis & Antiinflammatory Activity of Some New 3-( o -Substituted phenyl)-4-Substituted-Phenyl-5-Atkyl/Alkenyl-Mercapto-1H-1,2,4-Triazoles," *Indian J. Chem.*, 20B(II):1017-1018 (1981).
Tehranchian, S. et al., "Synthesis and antibacterial activity of 1-[1, 2, 4-triazol-3-yl] and 1-[1, 3, 4-thiadiazol-2-yl]-3-methylthio-6, 7-dihydrobenzo[c]thiophen-4(5H)ones," Bioorganic & Medicinal Chemistry Letters, 15:1023-1025 (2005).
Valbuena, J.R. et al., "Expression of Heat-Shock Protein-90 in Non-Hodgkin's Lymphomas," Modern Pathology, 18:1343-1349 (2005).
Van Cutsem, Eric et al, "Phase III Trial of Bevacizumab in Combination with Gemcitabine and Erlotinib in Patients with Metastatic Pancreatic Cancer", Journal of Clinical Oncology, 27 (13), p. 2231-2237, 2009.
Walton et al., "The Preclinical Pharmacology and Therapeutic Activity of the Novel CHK1 Inhibitor SAR-020106" Molecular Cancer Therapeutics, vol. 9(1): 89-100, Jan. 1, 2010.
Wang et. al., The Journal of Nutrition, 2003, American Society for Nutritional Science, vol. 133, pp. 2367-2376.
Wang Yisong et al: "STA-9090, a small-molecule Hsp90 inhibitor for the potential treatment of cancer", Current Opinion in Investigational Drugs, Thomson Reuters (Scientific) Ltd, London, UK, vol. 11, No. 12, Dec. 1, 2010 (Dec. 1, 2010), pp. 1466-1476, XP009159004, ISSN: 2040-3429.
Wax et al. "Geldanamycin Inhibits the Production of Inflammatory Cytokines in Activated Macrophages by Reducing the Stability and Translation of Cytokine Transcripts", Arthr. Rheum., 2003, vol. 48, No. 2, pp. 541-550.
Webb et al. The geldanamycins are potent inhibitors of the hepatocyte growth factor/scatter factor-met-urokinase plasminogen activator-plasmin proteolytic network. Cancer Research, 60, 342-349, Jan. 15, 2000.
Who Drug Information: "International Nonproprietary Names for Pharmaceutical Substances (INN)" Jun. 30, 2011 (Jun. 30, 2011), Retrieved from the Internet: URL:http://www.whoint/medicines/; publications/druginformation/innlists/PL105.pdf?ua=1.
Wong et al, An Open-Label Phase 2 Study of the; Hsp90 Inhibitor Ganetespib (STA-9090) as Monotherapy in Patients with Advanced NSCLC, Presentation, The 2011 American Society of Clinical Oncology (ASCO) Annual Meeting, Jun. 3-7, 2011.
Workman, "Overview: Translating HSP90 Biology into HSP90 Drugs", Current Cancer Drug Targets, 2003, vol. 3, pp. 297-300.
Wright, L., et ai., "Structure,..Activity Relationships in Purine-Based Inhibitor Binding to HSP90 Isoforms," *Chemistry & Biology*, 2004, 11, pp. 775-785.
Wu et al, "Activity of the Heat Shock Protein 90 Inhibitor; Ganetespib in Melanoma", PLoS One, 8:e56134 (2013).
Wu et al., Natl Cancer Inst, 95, 2003, 766-767.
Xiang et al, "Ganetespib blocks HIF-1 activity and inhibits tumor growth, vascularization, stem cell maintenance, invasion, and metastasis in orthotopic mouse models of triple-negative breast cancer", Author Manuscript, J Mol Med 92(2), 151-164 (2014).

(56) References Cited

OTHER PUBLICATIONS

Xie, L., et al., "Anti-AIDS Agents. 37. Synthesis and Structure-Activity Relationships of (3'R,4'R)-(+)-cis-Khellactone Derivatives as Novel Potent Anti-HIV Agents," *J. Med. Chem.* 42:2662-2672 (1999).

Xu et al., "Checkpoint kinase inhibitor synergizes with DNA-damaging agents in G1 checkpoint-defective neuroblastoma" Int'l J. of Cancer, 129, pp. 1953-1962, Jan. 1, 2011.

Yamada et ai, Mol Cancer Ther 2012;11 :1112-1121. Published OnlineFirst Mar. 8, 2012.

Yang, Zhen Fan et al, "High doses of tyrosine kinase inhibitor PTK787 enhance the efficacy of ischemic hypoxia for the treatment of hepatocellular carcinoma: dual effects on cancer cell and angiogenesis", Mol. Cancer Therapeutics, 5 (9), p. 2261-2270, 2006.

Yao et al. Cancer Therapy: Preclinical; "Synergism between Etoposide and 17-AAG in Leukemia Cells: Critical Roles for Hsp90, FLT3, Topoisomerase II, Chk1, and Rad51" 2007 (13) 1591-1600.

Yao Qing et al., "The Hsp90 inhibitor 17-AAG sensitizes human leukemia cells to proteasome inhibitor PS-341", Blood, American Society of Hematology, US, vol. 102, No. 11, pp. 622A-623A (2009).

Yao, Q., et al., "FLT3 Expressing Leukemias Are Selectively Sensitive to Inhibitors of the Molecular Chaperone Heat Shock Protein 90 Through Destabilization of Signal Transduction-Associated Kinases," Clinical Cancer Research 9:4483-4493 (Oct. 1, 2003).

Yap et al., "Targeting the PI3K-AKT-mTOR pathway: progress, pitfalls and promises", Current Opinion in Pharmacology, vol. 8, No. 4, pp. 393-412 (2008).

Ying et al, "Ganetespib, A Unique Resorcinolic Hsp90 Inhibitor, Exhibits Potent Antitumor Activity and A Superior Safety Profile in Preclinical Models", Poster, AACR-EORTC-NCI Molecular Targets and Cancer Therapeutics, Nov. 14, 2011—San Francisco, CA.

Ying et al, "Ganetespib, a Unique Triazolone-Containing Hsp90 Inhibitor,Exhibits Potent Antitumor Activity and a Superior Safety Profile for Cancer Therapy", Mol Cancer Res, 11:475484 (2011).

Ying et al, "Preclinical Evaluation of the Potent 2nd Generation Small-Molecule Hsp90 Inhibitor STA-9090 in Hematological Cell Lines", Poster, American Society of Hematology, Dec. 5, 2010—Orlando, FL.

Ying et al: "In Vitro and in Vivo Efficacy of the Novel Hsp90 Inhibitor STA-9090 and its Synergy with Paclitaxel", Poster, AACR-NCI-EORTC Molecular Targets and Cancer Therapeutics, Nov. 17, 2009—Boston, MA.

Yousif, N.M., et al., "Reactions of n, (3-spiroepoxyalkanones, Part IV—New and Facile Synthesis of Tetrahydronaphthalen-2-o1 derivatives for Biological Evaluation," Bulletin of the Faculty of Pharmacy (Cairo University), Chemical Abstracts Service, Database CA [online], 36(1):37-41 (1998).

Yu, Xiao Ming, et al, "Synthesis of (-)-Noviose from 2,3-O-Isopropylidene-D-erythronolactol" J. Org. Chem., 2004, 69 (21), pp. 7375-7378.

Yuksek, Haydar and Ikizler A. A., "Synthesis of 4-Succinimido-4,5-Dihydro-1H-1,2,4-Triazol-5-ones," Turkish Journal of Chemistry, 18: 57-61(1994).

Zhang et al. Pharmacokinetic and Toxicity Study of Intravitreal Erythropoietin in Rabbits; Acta Pharmacologica Sinica, vol. 29, No. 11 (2008) pp. 1383-1390.

Zhang et al. Targeting multiple signal transduction pathways through inhibition of Hsp90. J. Mol. Med. 2004, 82: 488-499.

Zhang, et al., Chemical Research in Chinese Universities (1997), 13(1), 27-33.

Zhang, L. et al., "Studies on Acylthiosemicarbazides and Related Heterocyclic Derivatives (XII)," Chemical Journal of Chinese Universities, 11(2):148-153 (1990).

Zhou et al, "Associating Retinal Drug Exposure and Retention with the Ocular Toxicity Profiles of Hsp90 Inhibitors", Poster, The 2012 American Society of Clinical Oncology (ASCO) Annual Meeting, Jun. 1-5, 2012—Chicago, IL.

Zhou et al, "A rat retinal damage model predicts for potential clinical visual disturbances induced by Hsp90 inhibitors", toxicol Appl Pharmacol, 273:401-409 (2013).

Zhou et al, "Heat Shock Protein (Hsp) 90 Inhibitor-Induced Ocular Toxicity: Critical Role of Tissue Distribution", Poster, AACR-EORTC-NCI Molecular Targets and Cancer Therapeutics, Nov. 15, 2011—San Francisco, CA.

Synta Press Release: Synta Pharmaceuticals Announces Ganetespib (STA-9090) Non-small Cell Lung Cancer Phase 2 Interim Results to be Presented at the Upcoming IASLC 11th Annual Targeted Therapies for the Treatment of Lung Cancer Meeting, Jan. 27, 2011.

Synta Press Release: Synta Announces Phase 2b/3 Trial for Ganetespib (STA-9090) in Advanced 2nd-line Non-small Cell Lung Cancer, Feb. 26, 2011.

Synta Press Release: Synta Announces Encouraging Preliminary Results for Ganetespib (STA-9090) in Phase 2 Non-small Cell Lung Cancer Trial, Feb. 26, 2011.

Synta Press Release: Synta to Host Investigator Panel Session on New Clinical Opportunities for Hsp90 Inhibition in Oncology, Mar. 21, 2011.

Synta Press Release: Synta Announces Ganetespib Results at AACR—Inhibition of Multiple Oncogenes and Resistance Mechanisms Leads to Potent Activity in NSCLC and Strong Enhancement of Radiation Therapy, Apr. 4, 2011.

Synta Press Release: Synta Announces Ganetespib Clinical Data Presentations at the 2011 American Society for Clinical Oncology (ASCO) Annual Meeting, May 18, 2011.

Synta Press Release: Synta Announces Publication of Results Showing Ganetespib (STA-9090) Exhibits Potent Activity in Models of Cancer with Activated JAK/STAT Signaling, May 26, 2011.

Synta Press Release: Synta Announces Ganetespib Phase 2 Non-small Cell Lung Cancer Trial Results Show Encouraging Single Agent Clinical Activity, Jun. 4, 2011.

Synta Press Release: Synta Announces Presentation of Additional Ganetespib Results at ASCO, Jun. 6, 2011.

Synta Press Release: Synta Announces Presentation of Ganetespib Phase 2 Non-small Cell Lung Cancer Trial Results at IASLC 14th World Conference on Lung Cancer, Jul. 7, 2011.

Synta Press Release: Synta Announces First Patient Treated in the GALAXY Trial™ a Phase 2b/3 Trial for Ganetespib in Advanced 2nd-line Non-small Cell Lung Cancer, Jul. 20, 2011 Synta Press Release: Synta Announces Presentation of Results of Ganetespib Study in Combination with Docetaxel in Solid Tumors, Sep. 26, 2011.

Synta Press Release: Synta Announces Results Show Ganetespib Sensitizes Rectal Cancer Cells to Chemoradiotherapy, Nov. 10, 2011.

Synta Press Release: Synta Presents Results on Ganetespib and Hsp90 Inhibitor Class at the AACR-EORTC-NCI Molecular Targets and Cancer Therapeutics Conference, Nov. 15, 2011.

Synta Press Release: Synta Announces Publication of Ganetespib Results in Molecular Cancer Therapeutics, Dec. 6, 2011.

Synta Press Release: Ganetespib Shows Clinical Activity in HER2+ and Triple Negative Metastatic Breast Cancer, Dec. 8, 2011.

Synta Press Release: Ganetespib Potently Inhibits Multiple Signaling Pathways Active in Breast Cancer, Dec. 12, 2011.

Synta Press Release: Ganetespib Showed Activity in KRAS-Mutant NSCLC as Monotherapy and in Combinations, Jan. 10, 2012.

Synta Press Release: Synta Announces Publication of Results Showing Ganetespib Synergizes with Taxanes in Multiple Non-small Cell Lung Cancer Models, Jan. 16, 2012.

Synta Press Release: Synta Announces Review of Ganetespib Results in Lung Cancer Presented at IASLC 12th Annual Targeted Therapies for the Treatment of Lung Cancer Meeting, Feb. 29, 2012.

Synta Press Release: Synta Announces Results on Ganetespib Across a Range of Malignancies at the American Association for Cancer Research (AACR) Annual Meeting, Apr. 4, 2012.

Synta Press Release: Multiple Myeloma Research Consortium (MMRC) and Synta Pharmaceuticals Announce Initiation of Ganetespib Clinical Trial in Multiple Myeloma, Apr. 10, 2012.

(56) References Cited

OTHER PUBLICATIONS

Synta Press Release: Synta Announces Results Demonstrating Potent Ganetespib Activity across Broad Range of Crizotinib-Resistant ALK+ NSCLC models at the European Lung Cancer Conference, Apr. 18, 2012.
Synta Press Release: Synta Announces Ganetespib Presentations at the Annual Meeting of the American Society for Clinical Oncology, Jun. 4, 2012.
Synta Press Release: Synta Announces Results from Interim Analysis of the Randomized Phase 2b/3 GALAXY Trial Evaluating Ganetespib plus Docetaxel in Second-Line Non-Small Cell Lung Cancer, Jun. 27, 2012.
Synta Press Release: Updated Results from Phase 2b/3 GALAXY Trial Show Promising Improvement in Survival from the Addition of Ganetespib to Docetaxel in Second-Line Non-Small Cell Lung Cancer, Sep. 29, 2012.
Synta Press Release: Synta Announces First Patients Treated in Pivotal GALAXY-2 Trial Evaluating Ganetespib in Advanced Non-Small Cell Lung Cancer, Apr. 22, 2013.
Synta Press Release: Synta Announces Positive Overall Survival Results From GALAXY-1 Phase 2b/3 Trial of Ganetespib in Second-Line Non-Small Cell Lung Cancer, Jun. 3, 2013.
Synta Press Release: Synta Announces Publication of Clinical and Non-Clinical Results Demonstrating Unique Anti-angiogenic Effects of Ganetespib, Jul. 17, 2013.
Synta Press Release: Synta Announces Fast Track Designation Granted for Ganetespib in Non-Small Cell Lung Adenocarcinoma, Sep. 12, 2013.
Synta Press Release: Synta Announces Presentation of Ganetespib Results at the 2013 European Cancer Congress, Sep. 28, 2013.
Synta Press Release: Synta Announces Positive One-Year Follow-up Results for the GALAXY-1 Trial of Ganetespib in NSCLC at the 2013 World Conference on Lung Cancer, Oct. 26, 2013.
Synta Press Release: Synta Announces Publications Demonstrating Ganetespib Activity in Triple-Negative Breast Cancer Models, Nov. 21, 2013.
Synta Press Release: Synta Announces Positive Interim Results from the ENCHANT-1 Trial of Ganetespib in Metastatic Breast Cancer at the 2013 San Antonio Breast Cancer Symposium, Dec. 12, 2013.
Synta Press Release: Synta Announces Launch of GANNET53, a Randomized, pan-European Study of Ganetespib in p53 Mutant, Metastatic Ovarian Cancer, Jan. 9, 2014.
Synta Press Release: Synta Announces Initiation of Three Multi-center, Randomized Phase II/III Trials of Ganetespib in Acute Myeloid Leukemia (AML) and High Risk Myelodysplastic Syndrome (MDS), Jan. 9, 2014.
Synta Press Release: Synta and QuantumLeap Healthcare Collaborative Announce Selection of Ganetespib for I-SPY 2 Trial in Breast Cancer, Mar. 11, 2014.
Synta Press Release: Synta Announces Positive Interim Results from the ENCHANT-1 Trial of Ganetespib in Metastatic Breast Cancer at the 9th European Breast Cancer Conference, Mar. 20, 2014.
Synta Press Release: Synta Announces Results From Final Analysis of the GALAXY-1 Trial of Ganetespib in NSCLC, May 8, 2014.
Synta Press Release: Synta Announces Advancement of Ganetespib into Phase 3 Extension of AML LI-1 Study for Patients with AML and High-Risk MDS, Jul. 21, 2014.
Synta Press Release: Synta Announces Initiation of I-SPY 2 Trial of Ganetespib in Breast Cancer, Oct. 29, 2014.
Synta Press Release: Synta Announces FDS's Oncologic Drugs Advisory Committee to Discuss Pediatric Uses for Ganetespib, Nov. 5, 2014.
Synta Press Release: Synta Announces Presentation of Results from an Investigator-Sponsored Phase 1 Trial of Ganetespib in HER2+ Metastatic Breast Cancer at the 2014 San Antonio Breast Cancer Symposium, Dec. 12, 2014.
Banerji et al., "An in vitro and in vivo study of the combination of the heat shock protein inhibitor 17-allylamino-17-demethoxygeldanamycin and carboplatin in human ovarian cancer models", Cancer Chemotherapy and Pharmacology, vol. 62, pp. 769-778 (Jan. 2008).
Dote et al., "Synergic antiproliferative effect of Hsp90 inhibitor in combination with cisplatin in gastric carcinoma cell lines", European Journal of Cancer Supplements, vol. 5, No. 4, p. 77, Abstract 374 (Sep. 2007).
Hwang et al., "HSP90 Inhibitors: Multi-Targeted Antitumor Effects and Novel Combinatorial Therapeutic Approaches in Cancer Therapy", Current Medicinal Chemistry, vol. 16, pp. 3081-3092 (Aug. 2009).
International Search Report and Written Opinion issued in PCT/US2012/063039 dated Apr. 1, 2013 (14 pages).
Moser et al., "Blocking heat shock protein-90 inhibits the invasive properties and hepatic growth of human colon cancer cells and improves the efficacy of oxaliplatin in p53-deficient colon cancer tumors in vivo", Molecular Cancer Therapeutics, vol. 6, No. 11, pp. 2868-2878 (Nov. 2007).

* cited by examiner

COMBINATION THERAPY OF HSP90 INHIBITORS WITH PLATINUM-CONTAINING AGENTS

CROSS-REFERENCE TO RELATED PATENTS

This application claims the benefit of priority to U.S. Provisional Patent Application Nos. 61/554,706, filed on Nov. 2, 2011. The contents of the above application are incorporated herein by reference in their entirety.

BACKGROUND OF THE INVENTION

Although tremendous advances have been made in elucidating the genomic abnormalities that cause malignant cancer cells, currently available chemotherapy remains unsatisfactory, and the prognosis for the majority of patients diagnosed with cancer remains dismal. Most chemotherapeutic agents act on a specific molecular target thought to be involved in the development of the malignant phenotype. However, a complex network of signaling pathways regulate cell proliferation and the majority of malignant cancers are facilitated by multiple genetic abnormalities in these pathways. Therefore, it is less likely that a therapeutic agent that acts on one molecular target will be fully effective in curing a patient who has cancer.

Heat shock proteins (HSPs) are a class of chaperone proteins that are up-regulated in response to elevated temperature and other environmental stresses, such as ultraviolet light, nutrient deprivation and oxygen deprivation. HSPs act as chaperones to other cellular proteins (called client proteins), facilitate their proper folding and repair and aid in the refolding of mis-folded client proteins. There are several known families of HSPs, each having its own set of client proteins. The Hsp90 family is one of the most abundant HSP families, accounting for about 1-2% of proteins in a cell that is not under stress and increasing to about 4-6% in a cell under stress. Inhibition of Hsp90 results in the degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer.

SUMMARY OF THE INVENTION

It has been found that certain triazolone Hsp90 inhibitor and platinum-containing anti-cancer agent combinations are surprisingly effective at treating subjects with certain cancers without further increasing the side effects profile of the individual agents. The particular combination therapies disclosed herein demonstrate surprising biological activity by demonstrating significant anticancer effects.

In an embodiment, the invention provides a method of utilizing Hsp90 inhibitors according to formulae (I) or (Ia), or a compound in Tables 1 or 2 for the treatment of proliferative disorders such as cancer, in combination with a platinum-containing anti-cancer agent. In an embodiment, a method of treating a subject with cancer includes administering to the subject an Hsp90 inhibitor according to formulae (I) or (Ia), or a compound in Tables 1 or 2, and a platinum-containing anti-cancer agent. In an embodiment, the administration of the Hsp90 inhibitor and the platinum-containing agent are done concurrently. In another embodiment, the administration of the Hsp90 inhibitor and the platinum-containing agent are done sequentially. In another embodiment, the administration of the Hsp90 inhibitor and the platinum-containing agent are dosed independently. In any one of these embodiments, the platinum-containing agent may be cisplatin, carboplatin, oxaliplatin, or their analogues. In any one of these embodiments, the Hsp90 inhibitor may be a compound represented in Tables 1 or 2. In any one of these embodiments, the platinum-containing agent may be cisplatin.

In some embodiments, the cancer may have mutations or translocations in the EGFR, K-Ras, c-Metc-Met, c-Kit, HER2, B-Raf, PI3K and/or ALK proteins. In some embodiments, the cancer may express wild-type EGFR and K-Ras. In some embodiments, the cancer may express mutated EGFR and wild-type K-Ras. In some embodiments, the cancer may express wild-type EGFR and mutated K-Ras protein. In some embodiments, the cancer may be ALK positive ("ALK+".) In some embodiments, the cancer may have an EML4-ALK translocation. In some embodiments, the cancer may have a HER2 mutation. In some embodiments, the cancer may have a PI#K mutation. In some embodiments, the cancer may have a B-Raf protein mutation.

In an embodiment, kits for administration of the combination therapy are provided. In an embodiment, the kit includes separate pharmaceutical compositions containing the Hsp90 inhibitor according to formulae (I) or (Ia) or a compound in Tables 1 or 2, and a platinum-containing anti-cancer agent. In another embodiment, the kit includes one pharmaceutical composition containing both the Hsp90 inhibitor and the platinum-containing anti-cancer agent. In any of these embodiments, each pharmaceutical composition includes one or more pharmaceutically acceptable carrier or diluent. In any one of these embodiments, the platinum-containing agent may be cisplatin, carboplatin, oxaliplatin, or their analogues. In any one of these embodiments, the Hsp90 inhibitor may be a compound represented in Tables 1 or 2. In any one of these embodiments, the platinum-containing agent may be cisplatin.

In an embodiment, the invention provides the use of an Hsp90 inhibitor according to formulae (I) or (Ia) or a compound in Tables 1 or 2 for the manufacture of a medicament for treating cancer in combination with a platinum-containing anti-cancer agent.

In an embodiment, a method of treating drug-resistant cancer in a subject includes administering to the subject an effective amount of the pharmaceutical combination including an Hsp90 compound according to formulae (I) or (Ia) or a compound in Tables 1 or 2 and a platinum-containing anti-cancer agent. In an embodiment, the method further includes the administration of one or more therapeutic agents. In certain embodiments, the combination treatment utilizes an Hsp90 compound according to formulae (I) or (Ia) or a compound in Tables 1 or 2 with a platinum-containing anti-cancer agent to help to arrest, partially or fully, or reduce the development of drug resistant cancer in a subject. The combinations described herein may allow a reduced dose of the platinum-containing agent given to a subject, because the Hsp90 inhibitor should inhibit the development of multidrug-resistant cancer cells. In an embodiment, the platinum-containing anti-cancer agent may be cisplatin, carboplatin, oxaliplatin, or their derivatives. In another embodiment, the platinum-containing agent may be cisplatin.

BRIEF DESCRIPTION OF THE DRAWINGS

The foregoing and other objects, features and advantages of the invention will be apparent from the following more particular description of some embodiments of the invention, as illustrated in the accompanying drawings. The drawings are not necessarily to scale, emphasis instead being placed upon illustrating the principles of the invention.

DETAILED DESCRIPTION OF THE INVENTION

Definitions

Figure 1:
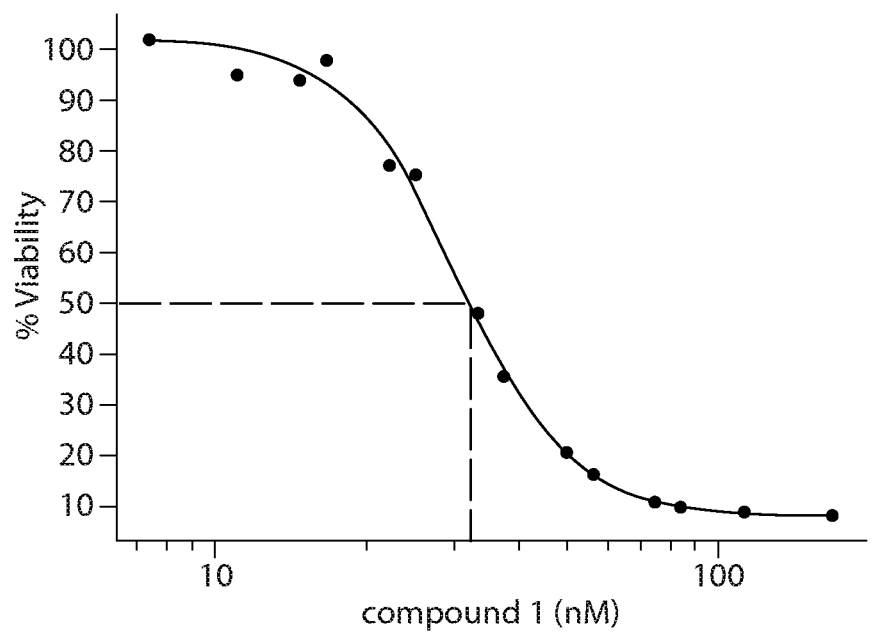
FIG. 1 shows a dose-dependent curve with the $IC_{50}$ of ganetespib, at about 32 nM.

Unless otherwise specified, the below terms used herein are defined as follows:

As used herein, the term "alkyl" means a saturated or unsaturated, straight chain or branched, non-cyclic hydrocarbon having from 1 to 10 carbon atoms. Representative straight chain alkyls include methyl, ethyl, n-propyl, n-butyl, n-pentyl, n-hexyl, n-heptyl, n-octyl, n-nonyl and n-decyl; while representative branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl, and the like. The term "$(C_1\text{-}C_6)$alkyl" means a saturated, straight chain or branched, non-cyclic hydrocarbon having from 1 to 6 carbon atoms. Alkyl groups included in compounds described herein may be optionally substituted with one or more substituents. Examples of unsaturated alkyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkyl groups included in compounds described herein may be optionally substituted with one or more substituents.

As used herein, the term "cycloalkyl" means a saturated or unsaturated, mono- or polycyclic, non-aromatic hydrocarbon having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, cyclodecyl, octahydropentalenyl, cyclohexenyl, cyclooctenyl, cyclohexynyl, and the like. Cycloalkyl groups included in compounds described herein may be optionally substituted with one or more substituents.

As used herein, the term "alkylene" refers to an alkyl group that has two points of attachment. The term "$(C_1\text{-}C_6)$ alkylene" refers to an alkylene group that has from one to six carbon atoms. Straight chain $(C_1\text{-}C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be saturated or unsaturated, and may be optionally substituted with one or more substituents.

As used herein, the term "lower" refers to a group having up to four atoms. For example, a "lower alkyl" refers to an alkyl radical having from 1 to 4 carbon atoms, "lower alkoxy" refers to "—O—$(C_1\text{-}C_4)$alkyl.

As used herein, the term "haloalkyl" means an alkyl group, in which one or more, including all, the hydrogen radicals are replaced by a halo group(s), wherein each halo group is independently selected from —F, —Cl, —Br, and —I. For example, the term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker. Alkoxy groups included in compounds described herein may be optionally substituted with one or more substituents.

As used herein, a "haloalkoxy" is a haloalkyl group which is attached to another moiety via an oxygen linker.

As used herein, the term an "aromatic ring" or "aryl" means a mono- or polycyclic hydrocarbon, containing from 6 to 15 carbon atoms, in which at least one ring is aromatic. Examples of suitable aryl groups include phenyl, tolyl, anthracenyl, fluorenyl, indenyl, azulenyl, and naphthyl, as well as benzo-fused carbocyclic moieties such as 5,6,7,8-tetrahydronaphthyl. Aryl groups included in compounds described herein may be optionally substituted with one or more substituents. In an embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1\text{-}C_6)$alkylene group. Representative aralkyl groups include benzyl, 2-phenylethyl, naphth-3-yl-methyl and the like. Aralkyl groups included in compounds described herein may be optionally substituted with one or more substituents.

As used herein, the term "heterocyclyl" means a monocyclic or a polycyclic, saturated or unsaturated, non-aromatic ring or ring system which typically contains 5- to 20-members and at least one heteroatom. A heterocyclic ring system can contain saturated ring(s) or unsaturated non-aromatic ring(s), or a mixture thereof. A 3- to 10-membered heterocycle can contain up to 5 heteroatoms, and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized, oxygen and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, a nitrogen atom may be substituted with a tert-butoxycarbonyl group. Furthermore, the heterocycle included in compounds described herein may be optionally substituted with one or more substituents. Only stable isomers of such substituted heterocyclic groups are contemplated in this definition.

As used herein, the term "heteroaryl", or like terms, means a monocyclic or a polycyclic, unsaturated radical containing at least one heteroatom, in which at least one ring is aromatic. Polycyclic heteroaryl rings must contain at least one heteroatom, but not all rings of a polycyclic heteroaryl moiety must contain heteroatoms. Each heteroatom is independently selected from nitrogen, which can be oxidized (e.g., N(O)) or quaternized, oxygen and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, an isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring may be a 5-8 membered monocyclic heteroaryl ring. The point of attachment of a heteroaromatic or heteroaryl ring may be at either a carbon atom or a heteroatom. Heteroaryl groups included in compounds described herein may be optionally substituted with one or more substituents. As used herein, the term "($C_5$)heteroaryl" means an heteroaromatic ring of 5 members, wherein at least one carbon atom of the ring is replaced with a heteroatom, such as, for example, oxygen, sulfur or nitrogen. Representative ($C_5$)heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like. As used herein, the term "($C_6$)heteroaryl" means an aromatic heterocyclic ring of 6 members, wherein at least one carbon atom of the ring is replaced with a heteroatom such as, for example, oxygen, nitrogen or sulfur. Representative ($C_6$)heteroaryls include pyridyl, pyridazinyl, pyrazinyl, triazinyl, tetrazinyl, and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl, and the like. Heteroaralkyl groups included in compounds described herein may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include are those substituents which form a stable compound described herein without significantly adversely affecting the reactivity or biological activity of the compound described herein. Examples of substituents for an alkyl, alkylene, alkenyl, alkynyl, cycloalkyl, cycloalkenyl, heterocyclyl, aryl, aralkyl, heteroaryl, and heteroaralkyl include an alkyl, alkenyl, alkynyl, cycloalkyl, cycloalkenyl, heterocyclyl, aryl, heteroaryl, aralkyl, heteraralkyl, heteroalkyl, alkoxy, (each of which can be optionally and independently substituted), —C(O)NR$^{28}$R$^{29}$, —C(S)NR$^{28}$R$^{29}$, —C(NR$^{32}$)NR$^{28}$R$^{29}$, —NR$^{33}$C(O)R$^{31}$, —NR$^{33}$C(S)R$^{31}$, —NR$^{33}$C(NR$^{32}$)R$^{31}$, halo, —OR$^{33}$, cyano, nitro, —C(O)R$^{33}$, —C(S)R$^{33}$, —C(NR$^{32}$)R$^{33}$, —NR$^{28}$R$^{29}$, —C(O)OR$^{33}$, —C(S)OR$^{33}$, —C(NR$^{32}$)OR$^{33}$, —OC(O)R$^{33}$, —OC(S)R$^{33}$, —OC(NR$^{32}$)R$^{33}$, —NR$^{30}$C(O)NR$^{28}$R$^{29}$, —NR$^{33}$C(S)NR$^{28}$R$^{29}$, —NR$^{33}$C(NR$^{32}$)NR$^{28}$R$^{29}$, —OC(O)NR$^{28}$R$^{29}$, —OC(S) NR$^{28}$R$^{29}$, —OC(NR$^{32}$)NR$^{28}$R$^{29}$, —NR$^{33}$C(O)OR$^{31}$, —NR$^{33}$C(S)OR$^{31}$, —NR$^{33}$C(NR$^{32}$)OR$^{31}$, —S(O)$_k$R$^{33}$, —OS(O)$_k$R$^{33}$, —NR$^{33}$S(O)$_k$R$^{33}$, —S(O)$_k$NR$^{28}$R$^{29}$, —OS(O)$_k$NR$^{28}$R$^{29}$, —NR$^{33}$S(O)$_k$NR$^{28}$R$^{29}$, guanidino, —C(O) SR$^{31}$, —C(S)SR$^{31}$, —C(NR$^{32}$)SR$^{31}$, —OC(O)OR$^{31}$, —OC (S)OR$^{31}$, —OC(NR$^{32}$)OR$^{31}$, —SC(O)R$^{33}$, —SC(O)OR$^{31}$, —SC(NR$^{32}$)OR$^{31}$, —SC(S)R$^{33}$, —SC(S)OR$^{31}$, —SC(O) NR$^{28}$R$^{29}$, —SC(NR$^{32}$)NR$^{28}$R$^{29}$, —SC(S)NR$^{28}$R$^{29}$, —SC (NR$^{32}$)R$^{33}$, —OS(O)$_k$OR$^{31}$, —S(O)$_k$OR$^{31}$, —NR$^{30}$S(O)$_k$ OR$^{31}$, —SS(O)$_k$R$^{33}$, —SS(O)$_k$OR$^{31}$, —SS(O)$_k$NR$^{28}$R$^{29}$, —OP(O)(OR$^{31}$)$_2$, or —SP(O)(OR$^{31}$)$_2$. In addition, any saturated portion of an alkyl, cycloalkyl, alkylene, heterocyclyl, alkenyl, cycloalkenyl, alkynyl, aralkyl and heteroaralkyl groups, may also be substituted with =O, =S, or =N—R$^{32}$. Each R$^{28}$ and R$^{29}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, or heteroalkyl represented by R$^{28}$ or R$^{29}$ is optionally and independently substituted. Each R$^{30}$, R$^{31}$ and R$^{33}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteroaralkyl represented by R$^{30}$ or R$^{31}$ or R$^{33}$ is optionally and independently unsubstituted. Each R$^{32}$ is independently H, alkyl, alkenyl, alkynyl, cycloalkyl, cycloalkenyl, heterocyclyl, aryl, heteroaryl, aralkyl, heteraralkyl, —C(O)R$^{33}$, —C(O)NR$^{28}$R$^{29}$, —S(O)$_k$R$^{33}$, or —S(O)$_k$NR$^{28}$R$^{29}$, wherein each alkyl, alkenyl, alkynyl, cycloalkyl, cycloalkenyl, heterocyclyl, aryl, heteroaryl, aralkyl and heteraralkyl represented by R$^{32}$ is optionally and independently substituted. The variable k is 0, 1 or 2. In some embodiments, suitable substituents include $C_1$-$C_4$ alkyl, $C_1$-$C_4$ haloalkyl, $C_1$-$C_4$ alkoxy, $C_1$-$C_4$ haloalkoxy, $C_1$-$C_4$ hydroxyalkyl, halo, or hydroxyl.

When a heterocyclyl, heteroaryl or heteroaralkyl group contains a nitrogen atom, it may be substituted or unsubstituted. When a nitrogen atom in the aromatic ring of a heteroaryl group has a substituent, the nitrogen may be oxidized or a quaternary nitrogen.

Unless indicated otherwise, the compounds described herein containing reactive functional groups, such as, for example, carboxy, hydroxy, thiol and amino moieties, also include corresponding protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. GREENE, PROTECTING GROUPS IN ORGANIC SYNTHESIS, (John Wiley & Sons, Inc., 1981).

As used herein, the term "compound(s) described herein" or similar terms refers to a compound of formulae (I), or (Ia) or a compound in Tables 1 or 2 or a tautomer or pharmaceutically acceptable salt thereof. Also included in the scope of the embodiments are a solvate, clathrate, hydrate, polymorph, prodrug, or protected derivative of a compound of formulae (I), or (Ia), or a compound in Tables 1 or 2.

The compounds described herein may contain one or more chiral centers and/or double bonds and, therefore, exist as stereoisomers, such as double-bond isomers (i.e., geometric isomers), enantiomers or diastereomers. Each chemical structure shown herein, including the compounds described herein, encompass all of the corresponding compound's enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds described herein are preferred.

When a disclosed compound is named or depicted by structure, it is to be understood that solvates (e.g., hydrates) of the compound or a pharmaceutically acceptable salt thereof is also included. "Solvates" refer to crystalline forms wherein solvent molecules are incorporated into the crystal lattice during crystallization. Solvates may include water or nonaqueous solvents such as ethanol, isopropanol, DMSO, acetic acid, ethanolamine and ethyl acetate. When water is the solvent molecule incorporated into the crystal lattice of a solvate, it is typically referred to as a "hydrate". Hydrates include stoichiometric hydrates as well as compositions containing variable amounts of water.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e., the capacity to occur in different crystalline forms). These different crystalline forms are typically known as "polymorphs." It is to be understood that when named or depicted by structure, the disclosed compounds and solvates (e.g., hydrates) also include all polymorphs thereof. Polymorphs have the same chemical composition but differ in packing, geometrical arrangement and other descriptive properties of the crystalline solid state. Polymorphs, therefore, may have different physical properties such as shape, density, hardness, deformability, stability and dissolution properties. Polymorphs typically exhibit different melting points, IR spectra and X-ray powder diffraction patterns, which may be used for identification. One of ordinary skill in the art will appreciate that different polymorphs may be produced, for example, by changing or adjusting the conditions used in crystallizing the compound. For example, changes in temperature, pressure or solvent may result in different polymorphs. In addition, one polymorph may spontaneously convert to another polymorph under certain conditions.

When a disclosed compound is named or depicted by structure, it is to be understood that clathrates ("inclusion compounds") of the compound or its pharmaceutically acceptable salt, solvate or polymorph, are also included. "Clathrate" means a compound described herein, or a salt thereof, in the form of a crystal lattice that contains spaces (e.g., channels) that have a guest molecule trapped within (e.g., a solvent or water).

As used herein, and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated herein include analogs or derivatives of compounds of formulae (I) or (Ia) or a compound in Tables 1 or 2 that comprise biohydrolyzable moieties such as biohydrolyzable amides, biohydrolyzable esters, biohydrolyzable carbamates, biohydrolyzable carbonates, biohydrolyzable ureides and phosphate analogues. Prodrugs can typically be prepared using well-known methods, such as those described by BURGER'S MEDICINAL CHEMISTRY AND DRUG DISCOVERY, (Manfred E. Wolff Ed., $5^h$ ed. (1995)) 172-178, 949-982.

The articles "a", "an" and "the" are used herein to refer to one or to more than one (i.e., to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In an embodiment, the subject is a non-human animal such as a farm animal (e.g., a horse, cow, pig or sheep), or a pet (e.g., a dog, cat, guinea pig or rabbit). In another embodiment, the subject is a human.

As used herein, "Hsp90" includes each member of the family of heat shock proteins having a mass of about 90-kiloDaltons. For example, in humans the highly conserved Hsp90 family includes the cytosolic Hsp90a and Hsp90β isoforms, as well as GRP94, which is found in the endoplasmic reticulum, and HSP75/TRAP1, which is found in the mitochondrial matrix.

The term "c-Kit" or "c-Kit kinase" refers to a membrane receptor protein tyrosine kinase which is preferably activated upon binding Stem Cell Factor (SCF) to its extracellular domain. Yarden, et al., *Embo. J.*, (1987) 11:3341-3351; Qiu, et al., *Embo. J.*, (1988) 7:1003-1011. The full length amino acid sequence of a c-Kit kinase preferably is as set forth in Yarden, et al.; and Qiu, et al., which are incorporated by reference herein in their entirety. Mutant versions of c-Kit kinase are encompassed by the term "c-Kit" or "c-Kit kinase" and include those that fall into two classes: (1) having a single amino acid substitution at codon 816 of the human c-Kit kinase, or its equivalent position in other species (Ma, et al., *J. Invest Dermatol.*, (1999) 112:165-170), and (2) those which have mutations involving the putative juxtamembrane z-helix of the protein (Ma, et al., *J. Biol. Chem.*, (1999) 274:13399-13402). Both of these publications are incorporated by reference herein in their entirety, including any drawings.

As used herein, "BCR-ABL" is a fusion protein that results from the translocation of gene sequences from c-ABL protein tyrosine kinase on chromosome 9 into BCR sequences on chromosome 22 producing the Philadelphia chromosome. A schematic representation of human BCR, ABL and BCR-ABL can be seen in FIG. 1 of U.S. patent application Ser. No. 10/193,651, filed on Jul. 9, 2002. Depending on the breaking point in the BCR gene, BCR-ABL fusion proteins can vary in size from 185-230 kD but they must contain at least the OLI domain from BCR and the TK domain from ABL for transforming activity. The most common BCR-ABL gene products found in humans are P230 BCR-ABL, P210 BCR-ABL and P190 BCR-ABL. P210 BCR-ABL is characteristic of CML and P190 BCR-ABL is characteristic of ALL.

FLT3 kinase is a tyrosine kinase receptor involved in the regulation and stimulation of cellular proliferation. Gilliland, et al., *Blood* (2002), 100:1532-42. The FLT3 kinase has five immunoglobulin-like domains in its extracellular region, as well as an insert region of 75-100 amino acids in the middle of its cytoplasmic domain. FLT3 kinase is activated upon the binding of the FLT3 ligand which causes receptor dimerization. Dimerization of the FLT3 kinase by FLT3 ligand activates the intracellular kinase activity as well as a cascade of downstream substrates including Stat5, Ras, phosphatidylinositol-3-kinase (PI3K), Erk2, Akt, MAPK, SHC, SHP2 and SHIP. Rosnet, et al., *Acta Haematol.* (1996), 95:218; Hayakawa, et al., *Oncogene* (2000), 19:624; Mizuki, et al., *Blood* (2000), 96:3907; Gilliland, et al., *Curr. Opin. Hematol.* (2002), 9: 274-81. Both membrane-bound and soluble FLT3 ligand bind, dimerize, and subsequently activate the FLT3 kinase.

Normal cells that express FLT3 kinase include immature hematopoietic cells, typically CD34+ cells, placenta, gonads and brain. Rosnet, et al., *Blood* (1993), 82:1110-19; Small, et al., *Proc. Natl. Acad. Sci. U.S.A.* (1994), 91:459-63; Rosnet, et al., *Leukemia* (1996), 10:238-48. However, efficient stimulation of proliferation via FLT3 kinase typically requires other hematopoietic growth factors or interleukins. FLT3 kinase also plays a critical role in immune function through its regulation of dendritic cell proliferation and differentiation. McKenna, et al., *Blood* (2000), 95:3489-497. Numerous hematologic malignancies express FLT3 kinase, the most prominent of which is AML. Yokota, et al., *Leukemia* (1997), 11:1605-09. Other FLT3 expressing malignancies include B-precursor cell acute lymphoblastic leukemias, myelodysplastic leukemias, T-cell acute lymphoblastic leukemias, and chronic myelogenous leukemias. Rasko, et al., *Leukemia* (1995), 9:2058-66.

FLT3 kinase mutations associated with hematologic malignancies are activating mutations. In other words, the FLT3 kinase is constitutively activated without the need for binding and dimerization by FLT3 ligand, and therefore stimulates the cell to grow continuously. Two types of activating mutations have been identified: internal tandem duplications (ITDs) and point mutation in the activating loop of the kinase domain. As used herein, the term "FLT3 kinase" refers to both wild type FLT3 kinase and mutant FLT3 kinases, such as FLT3 kinases that have activating mutations. Compounds provided herein are useful in treating conditions characterized by inappropriate FLT3 activity, such as proliferative disorders. Inappropriate FLT3 activity includes enhanced FLT3 activity resulting from increased or de novo expression of FLT3 in cells, increased FLT3 expression or activity, and FLT3 mutations resulting in constitutive activation. The existence of inappropriate or abnormal FLT3 ligand and FLT3 levels or activity can be determined using well-known methods in the art. For example, abnormally high FLT3 levels can be determined using commercially available ELISA kits. FLT3 levels can also be determined using flow cytometric analysis, immunohistochemical analysis and in situ hybridization techniques.

"Epidermal growth factor receptor" or "EGFR", as used herein, means any epidermal growth factor receptor (EGFR) protein, peptide, or polypeptide having EGFR or EGFR family activity (e.g., Her1, Her2, Her3 and/or Her4), such as encoded by EGFR Genbank Accession Nos. shown in Table I of U.S. patent application Ser. No. 10/923,354, filed on Aug. 20, 2004, or any other EGFR transcript derived from a EGFR gene and/or generated by EGFR translocation. The term "EGFR" is also meant to include other EGFR proteins, peptides, or polypeptides derived from EGFR isoforms (e.g., Her1, Her2, Her3 and/or Her4), mutant EGFR genes, splice variants of EGFR genes, and EGFR gene polymorphisms.

EGFR is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor α (TGFα), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

A number of human malignancies are associated with aberrant or overexpression of EGFR and/or overexpression of its specific ligands. Gullick, *Br. Med. Bull.* (1991), 47:87-98; Modijtahedi & Dean, *Int. J. Oncol.* (1994), 4:277-96; Salomon, et al., *Crit. Rev. Oncol. Hematol.* (1995), 19:183-232. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., *Anti-cancer Res.* (1999), 19:221-28; Veale, et al., *Br. J. Cancer* (1993); 68:162-65. Mutations in EGFR are associated with many types of cancer as well. For example, EGFR mutations are highly prevalent in non-mucinous BAC patients. Finberg, et al., *J. Mol. Diagnostics* (2007) 9(3): 320-26.

c-Met is a receptor tyrosine kinase that is encoded by the Met protooncogene and transduces the biological effects of hepatocyte growth factor (HGF), which is also referred to as scatter factor (SF). Jiang et al., *Crit. Rev. Oncol. Hemtol.* 29: 209-248 (1999), the entire teachings of which are incorporated herein by reference. c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). The c-Met receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-Met signaling is most commonly regulated by tumor-stroma (tumor-host) interactions. Furthermore, c-Met gene amplification, mutation, and rearrangement have been observed in a subset of human cancers. Families with germine mutations that activate c-Met kinase are prone to multiple kidney tumors as well as tumors in other tissues. Numerous studies have correlated the expression of c-Met and/or HGF/SF with the state of disease progression of different types of cancer (including lung, colon, breast, prostate, liver, pancreas, brain, kidney, ovaries, stomach, skin, and bone cancers). Furthermore, the overexpression of c-Met or HGF have been shown to correlate with poor prognosis and disease outcome in a number of major human cancers including lung, liver, gastric, and breast.

The anaplastic lymphoma kinase (ALK) tyrosine kinase receptor is an enzyme that, in humans, is encoded by the ALK gene. The 2;5 chromosomal translocation is frequently associated with anaplastic large cell lymphomas (ALCLs). The translocation creates a fusion gene consisting of the ALK (anaplastic lymphoma kinase) gene and the nucleophosmin (NPM) gene: the 3' half of ALK, derived from chromosome 2, is fused to the 5' portion of NPM from chromosome 5. The product of the NPM-ALK fusion gene is oncogenic. Other possible translocations of the ALK gene, such as the eml4 translocation, are also implicated in cancer.

The general role of ALK in cancer has been described. See, e.g., Pulford et al., *J. Cell Physiol.* 199(3): 330-358 (2004). Abnormalities in the anaplastic lymphoma kinase (ALK) gene have an established pathogenic role in many pediatric and adult cancers, including non-small cell lung cancer (NSCLC), diffuse large B-cell lymphoma (DLBCL), anaplastic large cell lymphoma (ALCL), neuroblastoma (NBL), and inflammatory myofibroblastic tumors (IMT), non-Hodgkin's lymphoma (NHL), and esophageal squamous cell carcinoma (ESCC). These diseases account for more than 250,000 new cancer diagnoses each year in the United States alone.

More particularly, EML4-ALK and KIF5B-ALK translocations have been found in non-small cell lung cancer. See. e.g. Mano H., Cancer Sci. 2008 December; 99(12):2349-55; Takeuchi K et al., Clin Cancer Res. 2009 May 1; 15(9): 3143-9. CLTC-ALK mutation has been found in DLBCL. See e.g. Rudzki Z et al., Pol J Pathol. 2005; 56 (1):37-45. NPM-ALK, MSN-ALK, and other mutations have been found in ALCL. See e.g. Lamant L et al., Genes Chromosomes Cancer. 2003 August; 37 (4):427-32; Webb T R et al. Expert Rev Anticancer Ther 2009 March; 9(3):331-56. TPM4-ALK mutation has been found in esophageal squamous cell carcinoma (ESCC). See e.g. Li R, Morris S W., Med Res Rev. 2008 May; 28 (3):372-412. F1174L, R1275Q, and other point mutations have been found in NBL. See e.g. van Roy N et al. Genome Med 2009 Jul. 27; 1 (7):74. TPM3-ALK, TPM4-ALK, CLTC-ALK, RanBP2-ALK, and TPM4-ALK mutations have been found in IMT. See e.g. Gleason B C, Hornick J L. J Clin Pathol 2008 April; 61(4):428-37. The methods of detection and identification of these alterations, mutations or rearrangements in an ALK gene or gene product can be found in the above-identified references and references cited therein.

The KRAS oncogene (the cellular homolog of the Kirsten rat sarcoma virus gene) is a critical gene in the development of a variety of cancers, and the mutation status of this gene is an important characteristic of many cancers. Mutation status of the gene can provide diagnostic, prognostic and predictive information for several cancers. The KRAS gene is a member of a family of genes (KRAS, NRAS and HRAS). KRAS is a member of the RAS family of oncogenes, a collection of small guanosine triphosphate (GTP)-binding proteins that integrate extracellular cues and activate intracellular signaling pathways to regulate cell proliferation, differentiation, and survival. Gain-of-function mutations that confer transforming capacity are frequently observed in KRAS, predominantly arising as single amino acid substitutions at amino acid residues G12, G13 or Q61. Constitutive activation of KRAS leads to the persistent stimulation of downstream signaling pathways that promote tumorigenesis, including the RAF/MEK/ERK and PI3K/AKT/mTOR cascades. In NSCLC, KRAS mutations are highly prevalent (20-30%) and are associated with unfavorable clinical outcomes. Mutations in KRAS appear mutually exclusive with those in EGFR in NSCLC tumors; more importantly, they can account for primary resistance to targeted EGFR TKI therapies. Mutations in the KRAS gene are common in many types of cancer, including pancreatic cancer (~65%), colon cancer (~40%), lung cancer (~20%) and ovarian cancer (~15%).

The methods and procedures for the detections and/or identifications of EGFR, KRAS, and/or ALK over-expressions and/or mutations are known in the literature and can be easily carried out by a skilled person. See, e.g., U.S. Pat. Nos. 7,700,339; 5,529,925; 5,770,421; U.S. Patent Application Publication No. US2011/0110923; Palmer et al, Biochem. J. (2009), 345-361; Koivunen et al, *Clin. Can. Res.*, 2008, 14, 4275-4283; Anderson, *Expert Rev. Mol. Diagn.* 11(6), 635-642 (2011); Pinto et al, *Cancer Genetics* 204 (2011), 439-446; Rekhtman et al; *Clin Cancer Res* 2012; 18:1167-1176; Massarelli et al, *Clin Cancer Res* 2007; 13:2890-2896; Lamy et al, *Modern Pathology* (2011) 24, 1090-1100; Balschun et al, *Expert Rev. Mol. Diagn.* 11(8), 799-802 (2011); Vakiani et al, *J Pathol* 2011; 223, 219-229; Okudela et al, *Pathology International* 2010; 60: 651-660; John et al, *Oncogene* (2009) 28, S14-S23; Jimeno et al, *J. Clin. Oncol.* 27, 1130-1135 (2009); Van Krieken et al, *Virchows Archiv.* 453, 417-431 (2008); and the references cited in the-above identified references. Thresholds of increased expression that constitute an EGFR mutation or an ALK mutation are well known in the art. Moreover, it is generally recognized that once an EGFR mutation is detected in a cancer, the KRAS mutation will be eliminated in the same cancer. Put reversely, if a KRAS mutation is positively identified in a cancer from a subject, it is then not necessary to engage in any further EGFR-related identification. Similar principle can be applied to an ALK mutation in a cancer. That is if there is an ALK mutation detected in a cancer, it is extremely rare that an EGFR or KRAS mutation will be implicated. Stated another way, once an ALK mutation is positively identified in a cancer, no further identification is necessary either for EGFR mutation or for KRAS mutation in the same cancer.

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, (e.g., diabetic retinopathy or other retinopathies), cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis and desmoid tumors. Non-cancerous proliferative disorders also include hyperproliferation of cells in the skin such as psoriasis and its varied clinical forms, Reiter's syndrome, pityriasis rubra pilaris, hyperproliferative variants of disorders of keratinization (e.g., actinic keratosis, senile keratosis), scleroderma, and the like. In an embodiment, the proliferative disorder is cancer.

In an embodiment, the invention provides a method of treating a proliferative disorder in a subject, comprising administering to the subject an effective amount of the combination of Hsp90 inhibitor and platinum-containing anti-cancer agent as described herein. In an embodiment, the proliferative disorder is cancer. In an embodiment, the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer is solid cancer, gastric cancer, bladder cancer, ovarian cancer, or colorectal cancer. In an embodiment, the cancer is colon cancer. In an embodiment, the cancer is metastatic colorectal cancer. In an embodiment, the cancer is bladder cancer. In an embodiment, the cancer is solid cancer. In an embodiment, the cancer is gastric cancer. In an embodiment, the cancer may have a mutation or translocation in EGFR, K-Ras, PI3K, ALK, HER2 and/or B-Raf proteins.

Some of the disclosed methods can be particularly effective at treating subjects whose cancer has become "drug resistant" or "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. "Drug resistant" tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Other anti-proliferative or anti-cancer therapies may be combined with the pharmaceutical combination of this invention to treat proliferative diseases and cancer. Other therapies or anti-cancer agents that may be used in combination with the inventive anti-cancer agents of the present invention include surgery, radiotherapy (including, but not limited to, gamma-radiation, neutron beam radiotherapy, electron beam radiotherapy, proton therapy, brachytherapy, and systemic radioactive isotopes), endocrine therapy, biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs. In an embodiment, the pharmaceutical combination of the invention is administered with one or more therapeutic agent selected from DFMO, vandetanib, trastuzumab, temodar, dexamethasone, epirubicin, ifosfamide, mitoxantrone, vorinostat, interferon alpha, rituximab, prednisone, cyclophosphamide, bendamustine, adriamycin, valproate, celecoxib, thalidomide, nelarabine, methotrexate, filgrastim, gemtuzumab ozogamicin, testosterone, clofarabine, cytarabine, everolimus, rituxumab, busulfan, capecitabine, pegfilgrastim, mesna, amrubicin, obatoclax, gefitinib, cyclosporine, dasatinib, temozolomide, thiotepa, plerixafor, mitotane, vincristine, doxorubicin, cixutumumab, endostar, fenofibrate, melphalan, sunitinib, rubitecan, enoxaparin, isotretinoin, tariquidar, pomalidomide, sorafenib, altretamine, idarubicin, rapamycin, zevalin, everolimus, pravastatin, carmustine, nelfinavir, streptozocin, tirapazamine, aprepitant, lenalidomide, G-CSF, procarbazine, alemtuzumab, amifostine, valspodar, lomustine, oblimersen, temsirolimus, vinblastine, figitumumab, belinostat, niacinamide, tipifarnib, estramustine, erlotinib, bevacizumab, paclitaxel, docetaxel, Abraxane®, pemetrexed, bortezomib, cetuximab, gemcitabine, 5-fluorouracil, leucovorin and tetracycline. In an embodiment, the one or more therapeutic agent is selected from erlotinib, bevacizumab, bortezomib, paclitaxel, doxorubicin, docetaxel, mitoxantrone, cytarabine, 5-fluorouracil, leucovorin, pemetrexed and vincristine.

As used herein, the term "pharmaceutically acceptable salt" refers to a salt prepared from a compound of formulae (I) or (Ia) or a compound in Tables 1 or 2 having an acidic functional group, such as a carboxylic acid functional group, and a pharmaceutically acceptable inorganic or organic base. Suitable bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of formulae (I) or (Ia) or a compound in Tables 1 or 2 having a basic functional group, such as an amine functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, isonicotinic acid, oleic acid, tannic acid, pantothenic acid, saccharic acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, pamoic acid and p-toluenesulfonic acid.

As used herein, the term "pharmaceutically acceptable solvate," is a solvate formed from the association of one or more pharmaceutically acceptable solvent molecules to one of the compounds of formulae (I) or (Ia) or a compound in Tables 1 or 2. The term "solvate" includes hydrates, e.g., hemihydrate, monohydrate, dihydrate, trihydrate, tetrahydrate, and the like.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON, J. P., REMINGTON'S PHARMACEUTICAL SCIENCES (Mack Pub. Co., $17^{th}$ ed., 1985). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate, and the like. Methods for encapsulating compositions, such as in a coating of hard gelatin or cyclodextran, are known in the art. See BAKER, ET AL., CONTROLLED RELEASE OF BIOLOGICAL ACTIVE AGENTS, (John Wiley and Sons, 1986).

As used herein, the term "effective amount" refers to an amount of a compound described herein which is sufficient to reduce or ameliorate the severity, duration, progression, or onset of a disease or disorder, delay onset of a disease or disorder, retard or halt the advancement of a disease or disorder, cause the regression of a disease or disorder, prevent or delay the recurrence, development, onset or progression of a symptom associated with a disease or disorder, or enhance or improve the therapeutic effect(s) of another therapy. In an embodiment of the invention, the disease or disorder is a proliferative disorder. The precise amount of compound administered to a subject will depend on the mode of administration, the type and severity of the disease or condition and on the characteristics of the subject, such as general health, age, sex, body weight and tolerance to drugs. For example, for a proliferative disease or disorder, determination of an effective amount will also depend on the degree, severity and type of cell proliferation. The skilled artisan will be able to determine appropriate dosages depending on these and other factors. When co-administered with other therapeutic agents, e.g., when co-administered with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used. In cases where no amount is expressly noted, an effective amount should be assumed. Non-limiting examples of an effective amount of a compound described herein are provided herein below. In a specific embodiment, the invention provides a method of treating, managing, or ameliorating a disease or disorder, e.g. a proliferative disorder, or one or more symptoms thereof, the method comprising administering to a subject in need thereof a dose of the Hsp90 inhibitor at least 150 µg/kg, at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, once every 2 days, once every 3 days, once every 4 days, once every 5 days, once every 6 days, once every 7 days, once every 8 days, once every 10 days, once every two weeks, once every three weeks, or once a month.

The dosage of the individual platinum-containing anticancer agent used in the pharmaceutical combination may be equal to or lower than the dose of an individual therapeutic agent when given independently to treat, manage, or ameliorate a disease or disorder, or one or more symptoms thereof. In an embodiment of the invention, the disease or disorder being treated with a combination therapy is a proliferative disorder. In an embodiment, the proliferative disorder is cancer. In an embodiment, the platinum-containing anticancer agent cisplatin is administered IV at a dose of between about 20 mg/m$^2$ to about 150 mg/m$^2$. In an embodiment, cisplatin is administered once daily. In an embodiment, cisplatin is administered IV at 20 mg/m$^2$ once daily. In an embodiment, cisplatin is administered IV at a dose of between about 75 mg/m$^2$ to about 100 mg/m$^2$. A treatment cycle can last between one and 6 weeks. The recommended dosages of therapeutic agents currently used for the treatment, management, or amelioration of a disease or disorder, or one or more symptoms thereof, can obtained from any reference in the art. For a more in depth review of dosage and treatment schedules for various disorders, see, e.g., GOODMAN & GILMAN'S THE PHARMACOLOGICAL BASIS OF BASIS OF THERAPEUTICS $9^{TH}$ ED, (Hardman, et al., Eds., NY:Mc-Graw-Hill (1996)); PHYSICIAN'S DESK REFERENCE $57^{TH}$ ED. (Medical Economics Co., Inc., Montvale, N.J. (2003)).

As used herein, the terms "treat", "treatment", "inhibiting", and "treating" refer to the reduction or amelioration of the progression, severity and/or duration of a disease or disorder, delay of the onset of a disease or disorder, or the amelioration of one or more symptoms (preferably, one or more discernible symptoms) of a disease or disorder, resulting from the administration of one or more therapies (e.g., one or more therapeutic agents such as a compound of the invention). The terms "treat", "treatment" and "treating" also encompass the reduction of the risk of developing a disease or disorder, and the delay or inhibition of the recurrence of a disease or disorder. In an embodiment, the disease or disorder being treated is a proliferative disorder such as cancer. In specific embodiments, the terms "treat", "treatment" and "treating" refer to the amelioration of at least one measurable physical parameter of a disease or disorder, such as growth of a tumor, not necessarily discernible by the patient. In other embodiments the terms "treat", "treatment" and "treating" refer to the inhibition of the progression of a disease or disorder, e.g., a proliferative disorder, either physically by the stabilization of a discernible symptom, physiologically by the stabilization of a physical parameter, or both. In another embodiment, the terms "treat", "treatment" and "treating" of a proliferative disease or disorder refers to the reduction or stabilization of tumor size or cancerous cell count, and/or delay of tumor formation. In another embodiment, the terms "treat", "treating" and "treatment" also encompass the administration of a compound described herein as a prophylactic measure to patients with a predisposition (genetic or environmental) to any disease or disorder described herein.

As used herein, the terms "therapeutic agent" and "therapeutic agents" refer to any agent(s) that can be used in the treatment of a disease or disorder, e.g. a proliferative disorder, or one or more symptoms thereof. In certain embodiments, the term "therapeutic agent" refers to a compound described herein. In certain other embodiments, the term "therapeutic agent" does not refer to a compound described herein. Preferably, a therapeutic agent is an agent that is known to be useful for, or has been or is currently being used for the treatment of a disease or disorder, e.g., a proliferative disorder, or one or more symptoms thereof.

As used herein, the term "synergistic" refers to a combination of a compound described herein and another therapeutic agent, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of the agent(s) to a subject with a disease or disorder, e.g., a proliferative disorder. The ability to utilize lower the dosage of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone.

As used herein, the phrase "side effects" encompasses unwanted and adverse effects of a therapeutic agent. Side effects are always unwanted, but unwanted effects are not necessarily adverse. An adverse effect from a therapeutic agent might be harmful or uncomfortable or risky to a subject. Side effects include fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapeutic agent. The use of the term "in combination" does not restrict the order in which the therapeutic agents are administered to a subject with a disease or disorder, e.g., a proliferative disorder. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer. In an embodiment, the Hsp90 inhibitor and the platinum-containing anti-cancer agent are dosed on independent schedules. In another embodiment, the Hsp90 inhibitor and the platinum-containing anti-cancer agent are dosed on approximately the same schedule. In another embodiment, the Hsp90 inhibitor and the platinum-containing anticancer agent are dosed concurrently or sequentially on the same day.

As used herein, the terms "therapies" and "therapy" can refer to any protocol(s), method(s), and/or agent(s) that can be used in the prevention, treatment, management, or amelioration of a disease or disorder, e.g., a proliferative disorder, or one or more symptoms thereof.

A used herein, a "protocol" includes dosing schedules and dosing regimens. The protocols herein are methods of use and include therapeutic protocols.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a "racemic mixture" means about 50% of one enantiomer and about 50% of is corresponding enantiomer of the molecule. The combination encompasses all enantiomerically-pure, enantiomerically-enriched, diastereomerically pure, diastereomerically enriched, and racemic mixtures of the compounds described herein. Enantiomeric and diastereomeric mixtures can be resolved into their component enantiomers or diastereomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

The compounds described herein are defined by their chemical structures and/or chemical names. Where a compound is referred to by both a chemical structure and a chemical name, and the chemical structure and the chemical name conflict, the chemical structure is determinative of the compound's identity.

When administered to a subject (e.g., a non-human animal for veterinary use or for improvement of livestock or to a human for clinical use), the compounds described herein are administered in an isolated form, or as the isolated form in a pharmaceutical composition. As used herein, "isolated" means that the compounds described herein are separated from other components of either: (a) a natural source, such as a plant or cell, preferably bacterial culture, or (b) a synthetic organic chemical reaction mixture. Preferably, the compounds described herein are purified via conventional techniques. As used herein, "purified" means that when isolated, the isolate contains at least 95%, preferably at least 98%, of a compound described herein by weight of the isolate either as a mixture of stereoisomers, or as a diastereomerically or enantiomerically pure isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

The methods described herein utilize triazolone compounds listed in Tables 1 or 2, or a compound represented by Formulae (I) or (Ia):

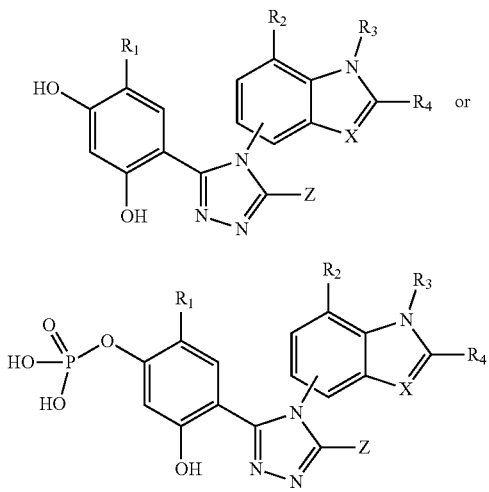

(I)

(Ia)

or a tautomer, or a pharmaceutically acceptable salt thereof, wherein:

Z is OH, SH, or $NH_2$;

X is $CR_4$ or N;

$R_1$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanidino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_2$ is —H, —OH, —SH, —$NR_7H$, —$OR_{15}$, —$SR_{15}$, —$NHR_{15}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$;

$R^3$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, hydroxyalkyl, alkoxyalkyl, a haloalkyl, a heteroalkyl, —$C(O)R^7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or —$S(O)_pNR_{10}R_{11}$;

$R^4$ is —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanidino, a haloalkyl, a heteroalkyl, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, —$S(O)_pNR_{10}R_{11}$, or $R_3$ and $R_4$ taken together with the carbon atoms to which they are attached form an optionally substituted cycloalkenyl, an optionally substituted aryl, an optionally substituted heterocyclyl, or an optionally substituted heteroaryl;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{15}$, for each occurrence, is independently, a lower alkyl;

p, for each occurrence, is, independently, 1 or 2; and m, for each occurrence, is independently, 1, 2, 3, or 4.

In an embodiment, in formula (I) or (Ia), X is $CR_4$. In another embodiment, in formula (I) or (Ia), X is N.

In another embodiment, in formula (I) or (Ia), $R_1$ may be —H, lower alkyl, lower alkoxy, lower cycloalkyl, or lower cycloalkoxy.

In another embodiment, in formula (I) or (Ia), $R_1$ may be —H, methyl, ethyl, propyl, isopropyl, cyclopropyl, methoxy, ethoxy, propoxy, or cyclopropoxy.

In another embodiment, in formula (I) or (Ia), $R^3$ may be —H, a lower alkyl, a lower cycloalkyl, —$C(O)N(R_{27})_2$, or —$C(O)OH$, wherein $R_{27}$ is —H or a lower alkyl.

In another embodiment, in formula (I) or (Ia), $R_3$ may be —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, or —C(O)N(CH$_3$)$_2$.

In another embodiment, $R_4$ may be H or a lower alkyl. In another embodiment, in formula (I) or (Ia), $R_4$ may be —H, methyl, ethyl, propyl, isopropyl or cyclopropyl.

In another embodiment, in formula (I) or (Ia), $R_1$ may be —H, —OH, —SH, —NH$_2$, a lower alkoxy or a lower alkyl amino. In another embodiment, in formula (I) or (Ia), $R_1$ may be —H, —OH, methoxy or ethoxy.

In another embodiment, in formula (I) or (Ia), Z is —OH.
In another embodiment, in formula (I) or (Ia), Z is —SH.
In another embodiment, in formula (I) or (Ia), $R_2$ may be —H, —OH, —SH, —NH$_2$, a lower alkoxy or a lower alkyl amino.

In another embodiment, in formula (I) or (Ia), $R_2$ may be —H, —OH, methoxy, or ethoxy.

In another embodiment, in formula (I) or (Ia), $R_1$ may be —H, methyl, ethyl, propyl, isopropyl, cyclopropyl, methoxy, ethoxy, propoxy, or cyclopropoxy; $R_3$ may be —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, or —C(O)N(CH$_3$)$_2$; $R_4$ may be —H, methyl, ethyl, propyl, isopropyl or cyclopropyl; $R_2$ may be —H, —OH, —SH, —NH$_2$, a lower alkoxy or a lower alkyl amino; and Z is OH.

In another embodiment, in formula (I) or (Ia), $R_1$ may be —H, methyl, ethyl, propyl, isopropyl, cyclopropyl, methoxy, ethoxy, propoxy, or cyclopropoxy; $R_3$ may be of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, or —C(O)N(CH$_3$)$_2$; $R_4$ may be —H, methyl, ethyl, propyl, isopropyl or cyclopropyl; $R_2$ may be of —H, —OH, —SH, —NH$_2$, a lower alkoxy or a lower alkyl amino; and Z is SH.

In another embodiment, the compound may be:
3-(2,4-dihydroxy-5-ethyl-phenyl)-4-(1,3-dimethyl-indol-5-yl)-5-hydroxy-[1,2,4]triazole,
3-(2,4-dihydroxy-5-isopropyl-phenyl)-4-(1,3-dimethyl-indol-5-yl)-5-hydroxy-[1,2,4]triazole,
3-(2,4-dihydroxy-5-isopropyl-phenyl)-4-(1-methyl-indol-5-yl)-5-hydroxy-[1,2,4]triazole,
3-(2,4-dihydroxy-5-isopropyl-phenyl)-4-(1-isopropyl-indol-4-yl)-5-hydroxy-[1,2,4]triazole,
3-(2,4-dihydroxy-5-isopropyl-phenyl)-4-(1-methyl-indazol-5-yl)-5-mercapto-[1,2,4]triazole,
3-(2,4-dihydroxy-5-isopropyl-phenyl)-4-(1-methyl-indazol-6-yl)-5-mercapto-[1,2,4]triazole,
3-(2,4-dihydroxyphenyl)-4-(1-ethyl-indol-4-yl)-5-mercapto-[1,2,4]triazole,
3-(2,4-dihydroxyphenyl)-4-(1-isopropyl-indol-4-yl)-5-mercapto-[1,2,4]triazole,
3-(2,4-dihydroxyphenyl)-4-(indol-4-yl)-5-mercapto-[1,2,4]triazole,
3-(2,4-dihydroxyphenyl)-4-(1-methoxyethyl-indol-4-yl)-5-mercapto-[1,2,4]triazole,
3-(2,4-dihydroxy-5-ethyl-phenyl)-4-(1-isopropyl-indol-4-yl)-5-mercapto-[1,2,4]triazole,
3-(2,4-dihydroxyphenyl)-4-(1-dimethylcarbamoyl-indol-4-yl)-5-mercapto-[1,2,4]triazole,
3-(2,4-dihydroxy-5-ethyl-phenyl)-4-(1-propyl-indol-4-yl)-5-mercapto-[1,2,4]triazole,
3-(2,4-dihydroxy-5-ethyl-phenyl)-4-(1,2,3-trimethyl-indol-5-yl)-5-mercapto-[1,2,4]triazole,
3-(2,4-dihydroxy-5-ethyl-phenyl)-4-(2,3-dimethyl-indol-5-yl)-5-mercapto-[1,2,4]triazole,
3-(2,4-dihydroxy-5-ethyl-phenyl)-4-(1-acetyl-2,3-dimethyl-indol-5-yl)-5-mercapto-[1,2,4]triazole,
3-(2,4-dihydroxy-5-ethyl-phenyl)-4-(1-propyl-2,3-dimethyl-indol-5-yl)-5-mercapto-[1,2,4]triazole,
3-(2,4-dihydroxy-5-ethyl-phenyl)-4-(1-n-butyl-indol-4-yl)-5-mercapto-[1,2,4]triazole,
3-(2,4-dihydroxy-5-ethyl-phenyl)-4-(1-n-pentyl-indol-4-yl)-5-mercapto-[1,2,4]triazole,
3-(2,4-dihydroxy-5-ethyl-phenyl)-4-(1-n-hexyl-indol-4-yl)-5-mercapto-[1,2,4]triazole,
3-(2,4-dihydroxy-5-cyclopropyl-phenyl)-4-(1-(1-methylcyclopropyl)-indol-4-yl)-5-mercapto-[1,2,4]triazole,
3-(2,4-dihydroxy-5-cyclopropyl-phenyl)-4-(1,2,3-trimethyl-indol-5-yl)-5-mercapto-[1,2,4]triazole,
3-(2,4-dihydroxy-5-ethyl-phenyl)-4-(1-methyl-3-ethyl-indol-5-yl)-5-mercapto-[1,2,4]triazole,
3-(2,4-dihydroxy-5-ethyl-phenyl)-4-(1,3-dimethyl-indol-5-yl)-5-mercapto-[1,2,4]triazole,
3-(2,4-dihydroxy-5-ethyl-phenyl)-4-(1-methyl-3-isopropyl-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-ethyl-phenyl)-4-(N-methyl-indol-5-yl)-5-mercapto-[1,2,4]triazole,
3-(2,4-dihydroxy-5-isopropyl-phenyl)-4-(1,3-dimethyl-indol-5-yl)-5-mercapto-[1,2,4]triazole,
3-(2,4-dihydroxy-5-cyclopropyl-phenyl)-4-(1,3-dimethyl-indol-5-yl)-5-mercapto-[1,2,4]triazole,
3-(2,4-dihydroxy-5-cyclopropyl-phenyl)-4-(1-methyl-indol-5-yl)-5-mercapto-[1,2,4]triazole,
3-(2,4-dihydroxy-5-isopropyl-phenyl)-4-(1H-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-isopropyl-phenyl)-4-(1-ethyl-indol-5-yl)-5-mercapto-[1,2,4]triazole, or
3-(2,4-dihydroxy-5-isopropyl-phenyl)-4-(1-propyl-indol-5-yl)-5-mercapto-[1,2,4]triazole, or a tautomer, or a pharmaceutically acceptable salt thereof.

In another embodiment, the compound may be:
3-(2,4-dihydroxy-5-ethyl-phenyl)-4-(1-ethyl-benzimidazol-4-yl)-5-mercapto-[1,2,4]triazole,
3-(2,4-dihydroxy-5-ethyl-phenyl)-4-(1-ethyl-benzimidazol-4-yl)-5-mercapto-[1,2,4]triazole HCL salt,
3-(2,4-dihydroxy-5-ethyl-phenyl)-4-(2-methyl-3-ethyl-benzimidazol-5-yl)-5-mercapto-[1,2,4]triazole,
3-(2,4-dihydroxy-5-ethyl-phenyl)-4-(1-ethyl-2-methyl-benzimidazol-5-yl)-5-mercapto-[1,2,4]triazole, or
3-(2,4-dihydroxy-5-isopropyl-phenyl)-4-(1-methyl-2-trifluoromethyl-benzimidazol-5-yl)-5-mercapto-[1,2,4]triazole,
or a tautomer, or a pharmaceutically acceptable salt thereof.

In another embodiment, the compound may be:
5-hydroxy-4-(5-hydroxy-4-(1-methyl-1H-indol-5-yl)-4H-1,2,4-triazol-3-yl)-2-isopropylphenyl dihydrogen phosphate,
sodium 5-hydroxy-4-(5-hydroxy-4-(1-methyl-1H-indol-5-yl)-4H-1,2,4-triazol-3-yl)-2-isopropylphenyl phosphate,
2-(3,4-dimethoxyphenethyl)-5-hydroxy-4-(5-hydroxy-4-(1-methyl-1H-indol-5-yl)-4H-1,2,4-triazol-3-yl)phenyl dihydrogen phosphate, 5-hydroxy-2-isopropyl-4-(5-mercapto-4-(4-methoxybenzyl)-4H-1,2,4-triazol-3-yl)phenyl dihydrogen phosphate,
5-hydroxy-4-(5-hydroxy-4-(4-methoxybenzyl)-4H-1,2,4-triazol-3-yl)-2-isopropylphenyl dihydrogen phosphate, or
4-(4-(1,3-dimethyl-1H-indol-5-yl)-5-hydroxy-4H-1,2,4-triazol-3-yl)-2-ethyl-5-hydroxyphenyl dihydrogen phosphate, or a tautomer, or a pharmaceutically acceptable salt thereof.

Hsp90 inhibitory compounds, as well as tautomers or pharmaceutically acceptable salts thereof that may be used in the methods described herein are depicted in Tables 1 or 2.

TABLE 1

| | STRUCTURE | TAUTOMERIC STRUCTURE | NAME |
|---|---|---|---|
| 1 | 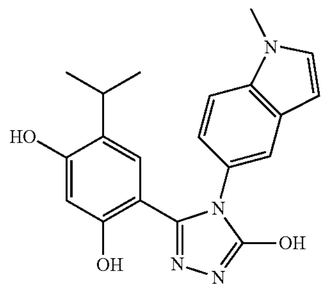 [SMILES: CC(C)c1cc(-c2nnc(O)n2-c2ccc3c(ccn3C)c2)c(O)cc1O] | | 3-(2,4-DIHYDROXY-5-ISOPROPYL-PHENYL)-4-(1-METHYL-INDOL-5-YL)-5-HYDROXY-[1,2,4] TRIAZOLE (GANETESPIB) |
| 2 | 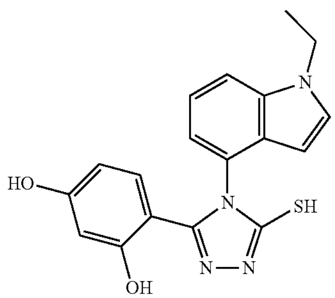 [SMILES: CCn1ccc2c(-n3c(S)nnc3-c3ccc(O)cc3O)cccc21] | | 3-(2,4-DIHYDROXYPHENYL)-4-(1-ETHYL-INDOL-4-YL)-5-MERCAPTO-[1,2,4] TRIAZOLE |
| 3 | 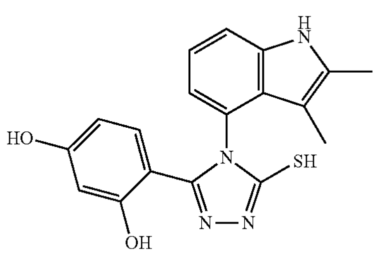 [SMILES: Cc1[nH]c2cccc(-n3c(S)nnc3-c3ccc(O)cc3O)c2c1C] | | 3-(2,4-DIHYDROXY-PHENYL)-4-(2,3-DIMETHYL-1H-INDOL-4-YL)-5-MERCAPTO-[1,2,4] TRIAZOLE |
| 4 | 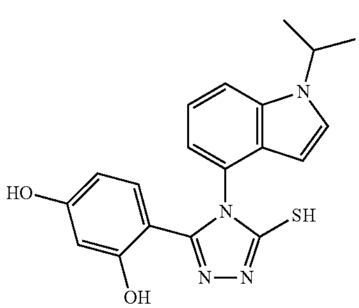 [SMILES: CC(C)n1ccc2c(-n3c(S)nnc3-c3ccc(O)cc3O)cccc21] | | 3-(2,4-DIHYDROXYPHENYL)-4-(1-ISOPROPYL-INDOL-4-YL)-5-MERCAPTO-[1,2,4] TRIAZOLE |
| 5 | 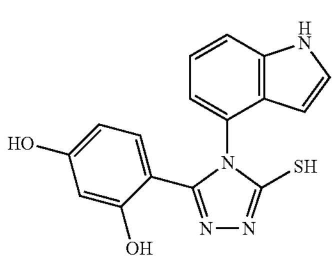 [SMILES: Oc1ccc(-c2nnc(S)n2-c2cccc3[nH]ccc23)c(O)c1] | | 3-(2,4-DIHYDROXY-PHENYL)-4-(INDOL-4-YL)-5-MERCAPTO-[1,2,4] TRIAZOLE |

TABLE 1-continued

| | STRUCTURE | TAUTOMERIC STRUCTURE | NAME |
|---|---|---|---|
| 6 | 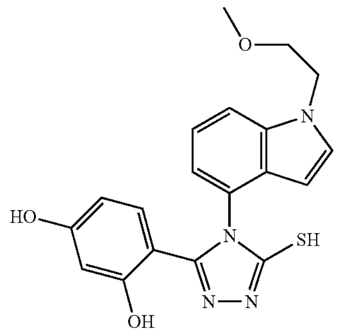 [SMILES: COCCn1ccc2c(-n3c(S)nnc3-c3ccc(O)cc3O)cccc21] | | 3-(2,4-DIHYDROXY-PHENYL)-4-[1-(2-METHOXYETHOXY)-INDOL-4-YL]-5-MERCAPTO-[1,2,4] TRIAZOLE |
| 7 | 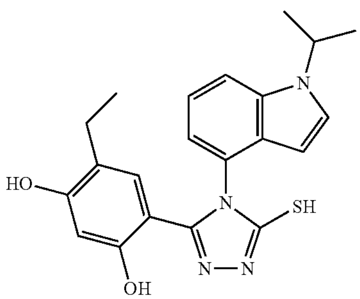 [SMILES: CCc1cc(-c2nnc(S)n2-c2cccc3c2ccn3C(C)C)c(O)cc1O] | | 3-(2,4-DIHYDROXY-5-ETHYL-PHENYL)-4-(1-ISOPROPYL-INDOL-4-YL)-5-MERCAPTO-[1,2,4] TRIAZOLE |
| 8 | 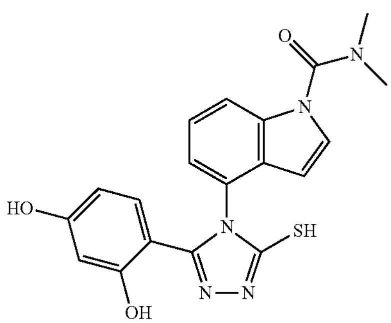 [SMILES: CN(C)C(=O)n1ccc2c(-n3c(S)nnc3-c3ccc(O)cc3O)cccc21] | | 3-(2,4-DIHYDROXY-5-ETHYL-PHENYL)-4-[1-(DIMETHYL-CARBAMOYL)-INDOL-4-YL]-5-MERCAPTO-[1,2,4] TRIAZOLE |
| 9 | 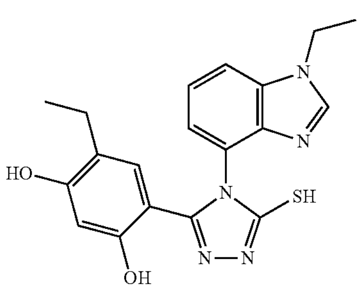 [SMILES: CCc1cc(-c2nnc(S)n2-c2cccc3c2ncn3CC)c(O)cc1O] | | 3-(2,4-DIHYDROXY-5-ETHYL-PHENYL)-4-(1-ETHYL-BENZOIMIDAZOL-4-YL)-5-MERCAPTO-[1,2,4] TRIAZOLE |
| 10 | 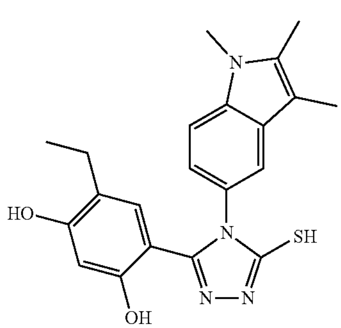 [SMILES: CCc1cc(-c2nnc(S)n2-c2ccc3c(c2)c(C)c(C)n3C)c(O)cc1O] | | 3-(2,4-DIHYDROXY-5-ETHYL-PHENYL)-4-(1,2,3-TRIMETHYL-INDOL-5-YL)-5-MERCAPTO-[1,2,4] TRIAZOLE |

TABLE 1-continued

| | STRUCTURE | TAUTOMERIC STRUCTURE | NAME |
|---|---|---|---|
| 11 | 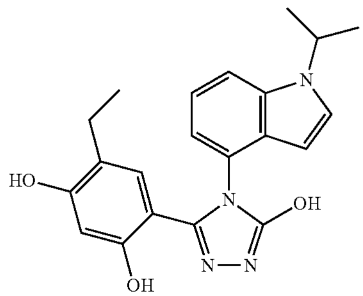 [SMILES: CCc1cc(-c2nnc(O)n2-c2cccc3c2ccn3C(C)C)c(O)cc1O] | | 3-(2,4-DIHYDROXY-5-ETHYL-PHENYL)-4-(1-ISOPROPYL-INDOL-3-YL)-5-HYDROXY-[1,2,4] TRIAZOLE |
| 12 | 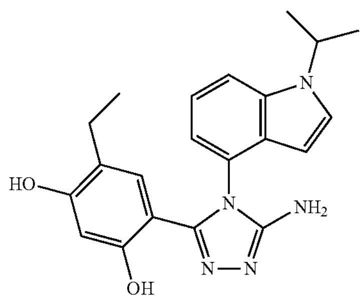 [SMILES: CCc1cc(-c2nnc(N)n2-c2cccc3c2ccn3C(C)C)c(O)cc1O] | | 3-(2,4-DIHYDROXY-5-ETHYL-PHENYL)-4-(1-ISOPROPYL-INDOL-4-YL)-5-AMINO-[1,2,4] TRIAZOLE |
| 15 | 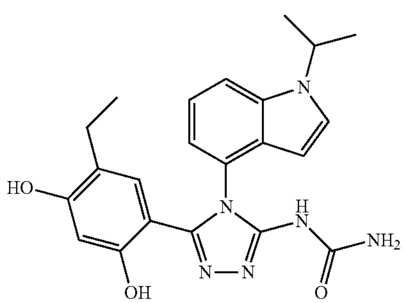 [SMILES: CCc1cc(-c2nnc(NC(N)=O)n2-c2cccc3c2ccn3C(C)C)c(O)cc1O] | | 3-(2,4-DIHYDROXY-5-ETHYL-PHENYL)-4-(1-ISOPROPYL-INDOL-4-YL)-5-UREIDO-[1,2,4] TRIAZOLE |
| 16 | 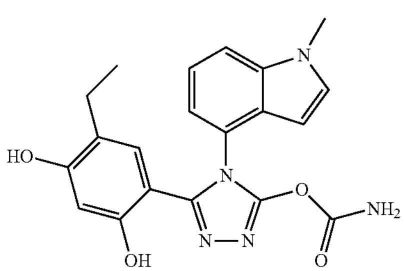 [SMILES: CCc1cc(-c2nnc(OC(N)=O)n2-c2cccc3c2ccn3C)c(O)cc1O] | | 3-(2,4-DIHYDROXY-5-ETHYL-PHENYL)-4-(1-METHYL-INDOL-4-YL)-5-CARBAMOYLOXY-[1,2,4] TRIAZOLE |
| 17 | 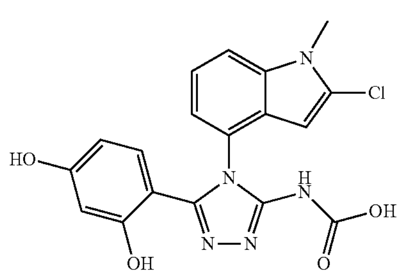 [SMILES: Cn1c(Cl)cc2c(-n3c(NC(=O)O)nnc3-c3ccc(O)cc3O)cccc21] | | 3-(2,4-DIHYDROXY-PHENYL)-4-(1-METHYL-2-CHLORO-INDOL-4-YL)-5-CARBAMOYLOXY-[1,2,4] TRIAZOLE |

TABLE 1-continued

| | STRUCTURE | TAUTOMERIC STRUCTURE | NAME |
|---|---|---|---|
| 18 | 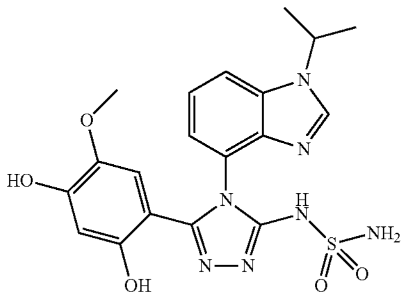 [SMILES: COc1cc(-c2nnc(NS(N)(=O)=O)n2-c2cccc3c2ncn3C(C)C)c(O)cc1O] | | 3-(2,4-DIHYDROXY-5-METHOXY-PHENYL)-4-(1-ISOPROPYL-BENZOIMIDAZOL-4-YL)-5-(SULFAMOYLAMINO)-[1,2,4] TRIAZOLE |
| 20 | 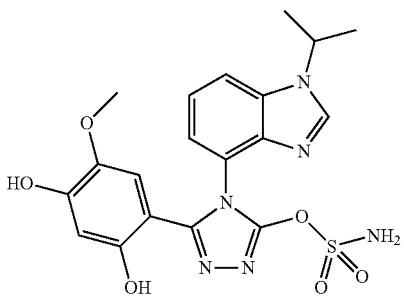 [SMILES: COc1cc(-c2nnc(OS(N)(=O)=O)n2-c2cccc3c2ncn3C(C)C)c(O)cc1O] | | 3-(2,4-DIHYDROXY-5-METHOXY-PHENYL)-4-(1-ISOPROPYL-BENZOIMIDAZOL-4-YL)-5-(SULFAMOYLOXY)-[1,2,4] TRIAZOLE |
| 21 | 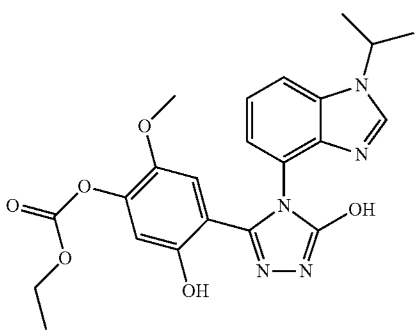 [SMILES: CCOC(=O)Oc1cc(O)c(-c2nnc(O)n2-c2cccc3c2ncn3C(C)C)cc1OC] | | 3-(2-HYDROXY-4-ETHOXYCARBONYOXY-5-METHOXY-PHENYL)-4-(1-ISOPROPYL-BENZOIMIDAZOL-4-YL)-5-HYDROXY-[1,2,4] TRIAZOLE |
| 22 | 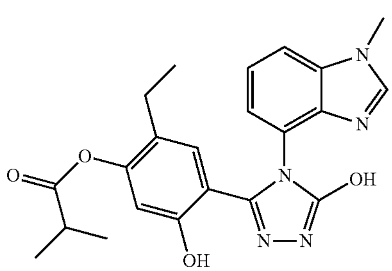 [SMILES: CCc1cc(-c2nnc(O)n2-c2cccc3c2ncn3C)c(O)cc1OC(=O)C(C)C] | | 3-[2-HYDROXY-4-ISOBUTYRYLOXY-5-ETHYL-PHENYL]-4-(1-METHYL-BENZO-IMIDAZOL-4-YL)-5-HYDROXY-[1,2,4] TRIAZOLE |
| 23 | 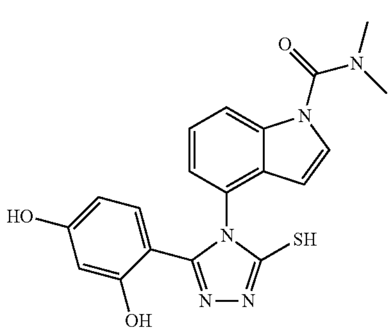 [SMILES: CN(C)C(=O)n1ccc2c(-n3c(S)nnc3-c3ccc(O)cc3O)cccc21] | | 3-(2,4-DIHYDROXY-PHENYL)-4-(1-DIMETHYL-CARBAMOYL-INDOL-4-YL)-5-MERCAPTO-[1,2,4] TRIAZOLE |

TABLE 1-continued

| | STRUCTURE | TAUTOMERIC STRUCTURE | NAME |
|---|---|---|---|
| 24 | 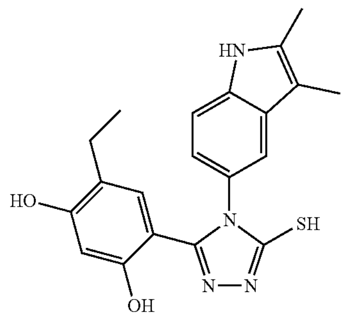 [SMILES: CCc1cc(-c2nnc(S)n2-c2ccc3[nH]c(C)c(C)c3c2)c(O)cc1O] | | 3-(2,4-DIHYDROXY-5-ETHYL-PHENYL)-4-(2,3-DIMETHYL-INDOL-5-YL)-5-MERCAPTO-[1,2,4] TRIAZOLE |
| 25 | 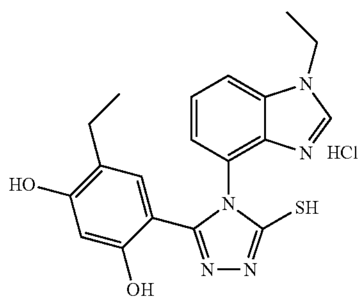 [SMILES: CCc1cc(-c2nnc(S)n2-c2cccc3c2ncn3CC)c(O)cc1O ; Cl] | | 3-(2,4-DIHYDROXY-5-ETHYL-PHENYL)-4-(1-ETHYL-1H-BENZOIMIDAZOL-4-YL)-5-MERCAPTO-[1,2,4] TRIAZOLE, HCL SALT |
| 26 | 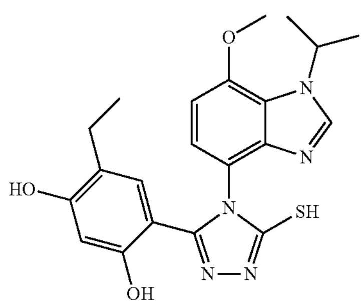 [SMILES: CCc1cc(-c2nnc(S)n2-c2ccc(OC)c3c2ncn3C(C)C)c(O)cc1O] | | 3-(2,4-DIHYDROXY-5-ETHYL-PHENYL)-4-(1-ISOPROPYL-7-METHOXY-INDOL-4-YL)-5-MERCAPTO-[1,2,4] TRIAZOLE |
| 27 | 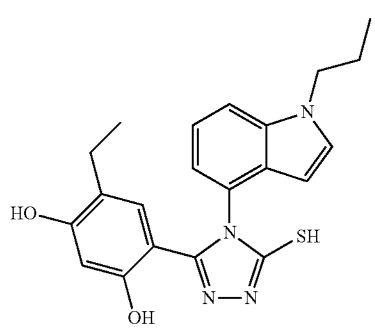 [SMILES: CCCn1ccc2c(-n3c(S)nnc3-c3cc(CC)c(O)cc3O)cccc21] | | 3-(2,4-DIHYDROXY-5-ETHYL-PHENYL)-4-(1-PROPYL-INDOL-4-YL)-5-MERCAPTO-[1,2,4] TRIAZOLE |
| 28 | 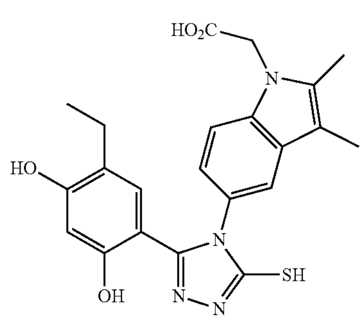 [SMILES: CCc1cc(-c2nnc(S)n2-c2ccc3c(c2)c(C)c(C)n3CC(=O)O)c(O)cc1O] | | 3-(2,4-DIHYDROXY-5-ETHYL-PHENYL)-4-(1-ACETYL-2,3-DIMETHYL-INDOL-5-YL)-5-MERCAPTO-[1,2,4] TRIAZOLE |

TABLE 1-continued

| | STRUCTURE | TAUTOMERIC STRUCTURE | NAME |
|---|---|---|---|
| 29 | 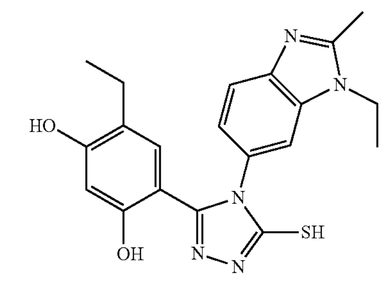 [SMILES: CCc1cc(-c2nnc(S)n2-c2ccc3nc(C)n(CC)c3c2)c(O)cc1O] | | 3-(2,4-DIHYDROXY-5-ETHYL-PHENYL)-4-(2-METHYL-3-ETHYL-BENZIMIDAZOL-5-YL)-5-MERCAPTO-[1,2,4]TRIAZOLE |
| 30 | 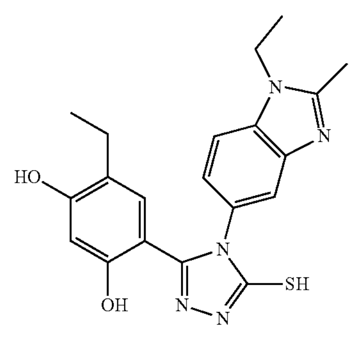 [SMILES: CCc1cc(-c2nnc(S)n2-c2ccc3c(c2)nc(C)n3CC)c(O)cc1O] | | 3-(2,4-DIHYDROXY-5-ETHYL-PHENYL)-4-(1-ETHYL-2-METHYL-BENZIMIDAZOL-5-YL)-5-MERCAPTO-[1,2,4]TRIAZOLE |
| 31 | 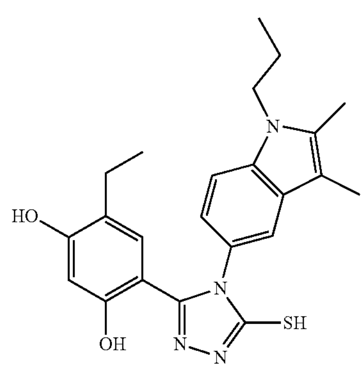 [SMILES: CCCn1c(C)c(C)c2cc(-n3c(S)nnc3-c3cc(CC)c(O)cc3O)ccc21] | | 3-(2,4-DIHYDROXY-5-ETHYL-PHENYL)-4-(1-PROPYL-2,3-DIMETHYL-INDOL-5-YL)-5-MERCAPTO-[1,2,4]TRIAZOLE |
| 34 | 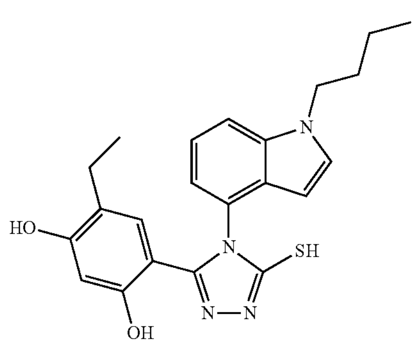 [SMILES: CCCCn1ccc2c(-n3c(S)nnc3-c3cc(CC)c(O)cc3O)cccc21] | | 3-(2,4-DIHYDROXY-5-ETHYL-PHENYL)-4-(1-N-BUTYL-INDOL-4-YL)-5-MERCAPTO-[1,2,4]TRIAZOLE |

TABLE 1-continued

| STRUCTURE | TAUTOMERIC STRUCTURE | NAME |
|---|---|---|
| 35 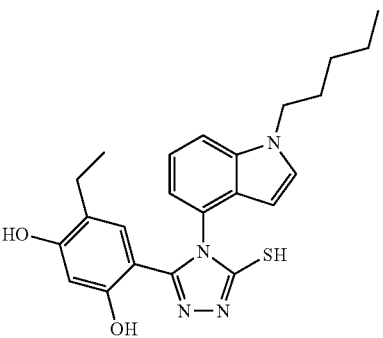 [SMILES: CCCCCn1ccc2c(-n3c(S)nnc3-c3cc(CC)c(O)cc3O)cccc21] | 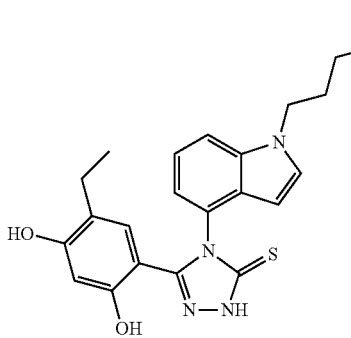 | 3-(2,4-DIHYDROXY-5-ETHYL-PHENYL)-4-(1-N-PENTYL-INDOL-4-YL)-5-MERCAPTO-[1,2,4] TRIAZOLE |
| 36 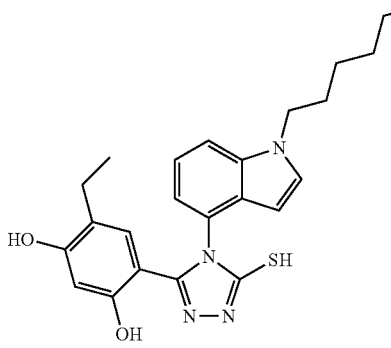 | 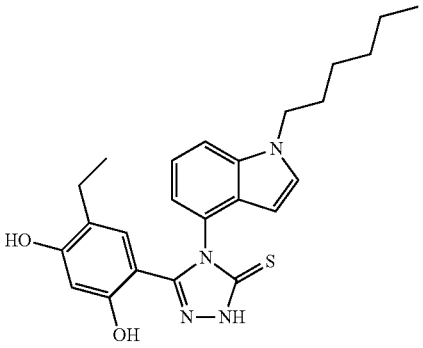 [SMILES: CCCCCCn1ccc2c(-n3c(-c4cc(CC)c(O)cc4O)n[nH]c3=S)cccc21] | 3-(2,4-DIHYDROXY-5-ETHYL-PHENYL)-4-(1-N-HEXYL-INDOL-4-YL)-5-MERCAPTO-[1,2,4] TRIAZOLE |
| 37 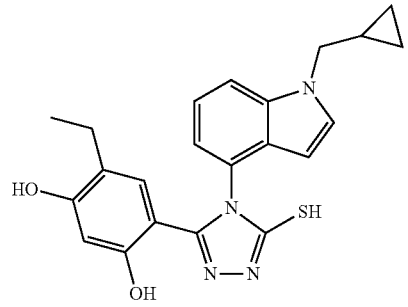 [SMILES: CCc1cc(-c2nnc(S)n2-c2cccc3c2ccn3CC2CC2)c(O)cc1O] | 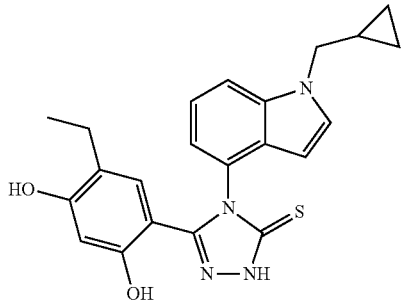 [SMILES: CCc1cc(-c2n[nH]c(=S)n2-c2cccc3c2ccn3CC2CC2)c(O)cc1O] | 3-(2,4-DIHYDROXY-5-CYCLOPROPYL-PHENYL)-4-(1-(1-METHYL-CYCLOPROPYL)-INDOL-4-YL)-5-MERCAPTO-[1,2,4] TRIAZOLE |
| 38 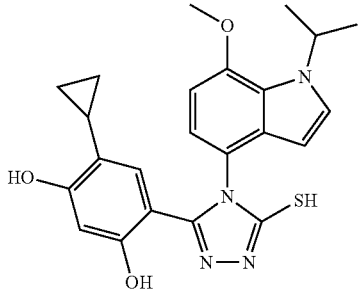 [SMILES: COc1ccc(-n2c(S)nnc2-c2cc(C3CC3)c(O)cc2O)c2ccn(C(C)C)c12] | 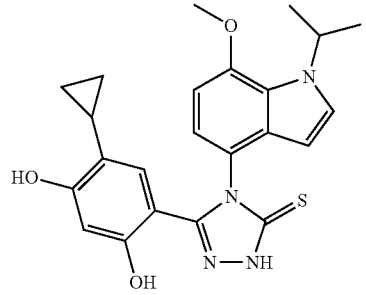 [SMILES: COc1ccc(-n2c(-c3cc(C4CC4)c(O)cc3O)n[nH]c2=S)c2ccn(C(C)C)c12] | 3-(2,4-DIHYDROXY-5-CYCLOPROPYL-PHENYL)-4-(1-ISOPROPYL-7-METHOXY-INDOL-4-YL)-5-MERCAPTO-[1,2,4] TRIAZOLE |
| 39 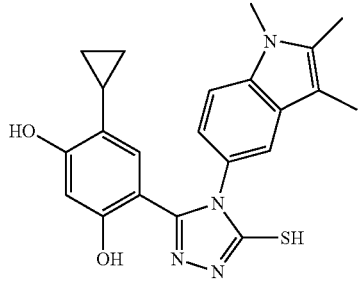 | 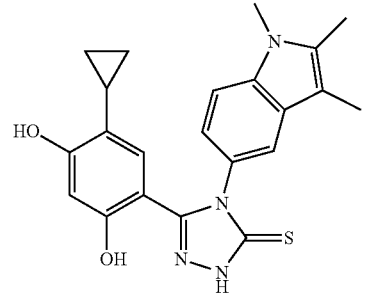 [SMILES: Cc1c(C)n(C)c2ccc(-n3c(-c4cc(C5CC5)c(O)cc4O)n[nH]c3=S)cc12] | 3-(2,4-DIHYDROXY-5-CYCLOPROPYL-PHENYL)-4-(1,2,3-TRIMETHYL-INDOL-5-YL)-5-MERCAPTO-[1,2,4] TRIAZOLE |

TABLE 1-continued

| STRUCTURE | TAUTOMERIC STRUCTURE | NAME |
|---|---|---|
| 40 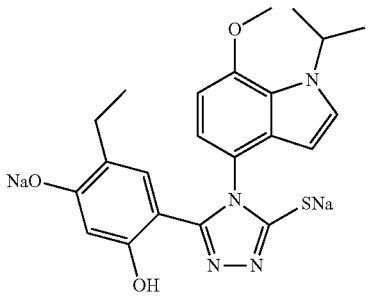 | | 3-(2,4-DIHYDROXY-5-ETHYL-PHENYL)-4-(1-ISOPROPYL-7-METHOXY-INDOL-4-YL)-5-MERCAPTO-[1,2,4] TRIAZOLE DISODIUM SALT |
| 41  | 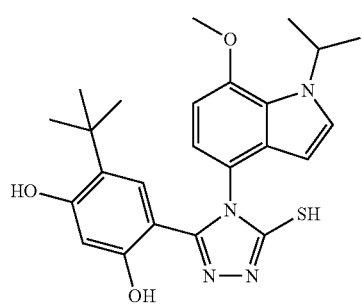 [SMILES: COc1ccc(-n2c(S)nnc2-c2cc(C(C)(C)C)c(O)cc2O)c2ccn(C(C)C)c12] | 3-(2,4-DIHYDROXY-5-TERT-BUTYL-PHENYL)-4-(1-ISOPROPYL-7-METHOXY-INDOL-4-YL)-5-MERCAPTO-[1,2,4] TRIAZOLE |
| 42 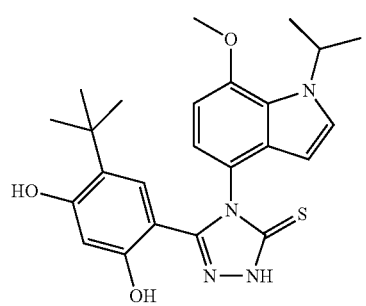 [SMILES: COc1ccc(-n2c(-c3cc(C(C)(C)C)c(O)cc3O)n[nH]c2=S)c2ccn(C(C)C)c12] | 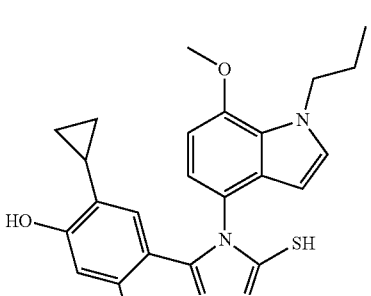 | 3-(2,4-DIHYDROXY-5-CYCLOPROPYL-PHENYL)-4-(1-PROPYL-7-METHOXY-INDOL-4-YL)-5-MERCAPTO-[1,2,4] TRIAZOLE |
| 43 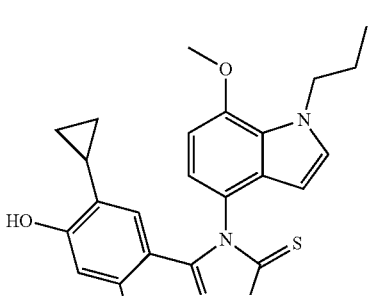 | 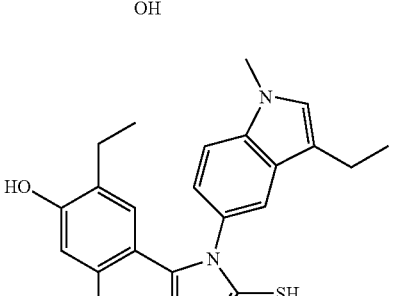 | 3-(2,4-DIHYDROXY-5-ETHYL-PHENYL)-4-(1-METHYL-3-ETHYL-INDOL-5-YL)-5-MERCAPTO-[1,2,4] TRIAZOLE |
| 44 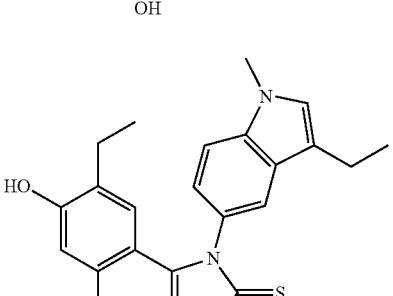 | 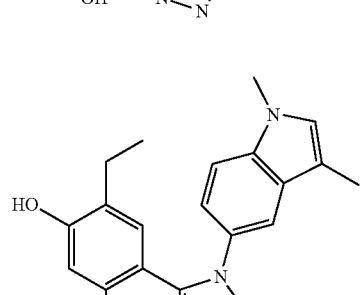 | 3-(2,4-DIHYDROXY-5-ETHYL-PHENYL)-4-(1,3-DIMETHYL-INDOL-5-YL)-5-MERCAPTO-[1,2,4] TRIAZOLE |

TABLE 1-continued

| STRUCTURE | TAUTOMERIC STRUCTURE | NAME |
|---|---|---|
| 45 | | 3-(2,4-DIHYDROXY-5-ISOPROPYL-PHENYL)-4-(1-ISOPROPYL-7-METHOXY-INDOL-4-YL)-5-MERCAPTO-[1,2,4] TRIAZOLE |
| 46 | | 3-(2,4-DIHYDROXY-5-ETHYL-PHENYL)-4-(1-METHYL-3-ISOPROPYL-INDOL-5-YL)-5-MERCAPTO-[1,2,4] TRIAZOLE |
| 48 | | 3-(2,4-DIHYDROXY-5-ETHYL-PHENYL)-4-(1-ISOPROPYL-7-HYDROXY-INDOL-4-YL)-5-MERCAPTO-[1,2,4] TRIAZOLE |
| 49 | | 3-(2,4-DIHYDROXY-5-ETHYL-PHENYL)-4-(1-ISOPROPYL-7-ETHOXY-INDOL-4-YL)-5-MERCAPTO-[1,2,4] TRIAZOLE |
| 50 | | 3-(2,4-DIHYDROXY-5-ETHYL-PHENYL)-4-(1,2-DIMETHYL-INDOL-5-YL)-5-MERCAPTO-[1,2,4] TRIAZOLE |

TABLE 1-continued

| | STRUCTURE | TAUTOMERIC STRUCTURE | NAME |
|---|---|---|---|
| 51 | 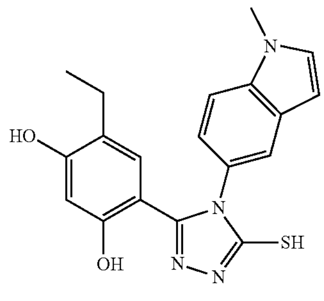 [SMILES: CCc1cc(-c2nnc(S)n2-c2ccc3c(ccn3C)c2)c(O)cc1O] | | 3-(2,4-DIHYDROXY-5-ETHYL-PHENYL)-4-(N-METHYL-INDOL-5-YL)-5-MERCAPTO-[1,2,4] TRIAZOLE |
| 55 | 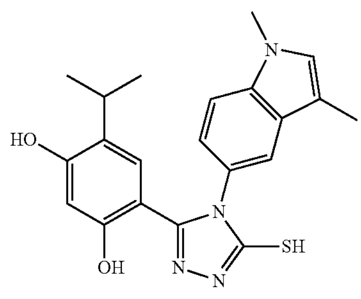 [SMILES: Cc1cn(C)c2ccc(-n3c(S)nnc3-c3cc(C(C)C)c(O)cc3O)cc12] | | 3-(2,4-DIHYDROXY-5-ISOPROPYL-PHENYL)-4-(1,3-DIMETHYL-INDOL-5-YL)-5-MERCAPTO-[1,2,4] TRIAZOLE |
| 56 | 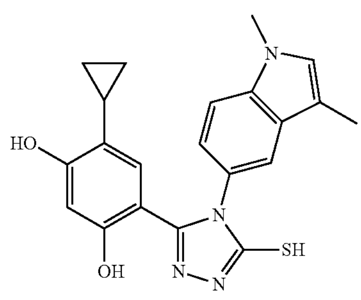 [SMILES: Cc1cn(C)c2ccc(-n3c(S)nnc3-c3cc(C4CC4)c(O)cc3O)cc12] | | 3-(2,4-DIHYDROXY-5-CYCLOPROPYL-PHENYL)-4-(1,3-DIMETHYL-INDOL-5-YL)-5-MERCAPTO-[1,2,4] TRIAZOLE |
| 57 | 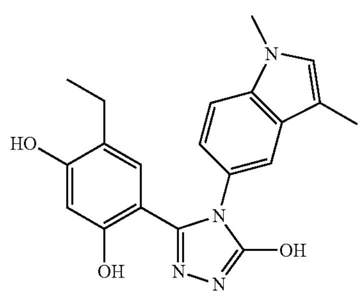 [SMILES: CCc1cc(-c2nnc(O)n2-c2ccc3c(c2)c(C)cn3C)c(O)cc1O] | | 3-(2,4-DIHYDROXY-5-ETHYL-PHENYL)-4-(1,3-DIMETHYL-INDOL-5-YL)-5-HYDROXY-[1,2,4] TRIAZOLE |
| 58 | 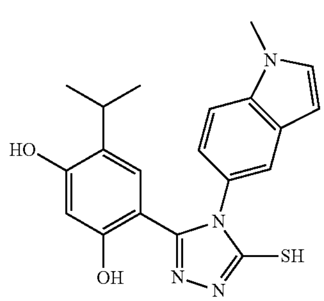 [SMILES: CC(C)c1cc(-c2nnc(S)n2-c2ccc3c(ccn3C)c2)c(O)cc1O] | | 3-(2,4-DIHYDROXY-5-ISOPROPYL-PHENYL)-4-(N-METHYL-INDOL-5-YL)-5-MERCAPTO-[1,2,4] TRIAZOLE |

TABLE 1-continued

| | STRUCTURE | TAUTOMERIC STRUCTURE | NAME |
|---|---|---|---|
| 59 | 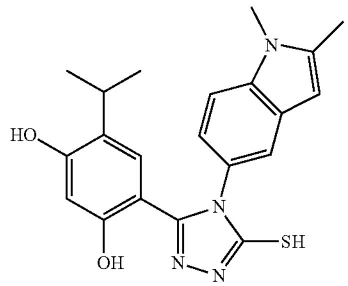 [SMILES: Cc1cc2cc(-n3c(S)nnc3-c3cc(C(C)C)c(O)cc3O)ccc2n1C] | | 3-(2,4-DIHYDROXY-5-ISOPROPYL-PHENYL)-4-(1,2-DIMETHYL-INDOL-5-YL)-5-MERCAPTO-[1,2,4] TRIAZOLE |
| 60 | 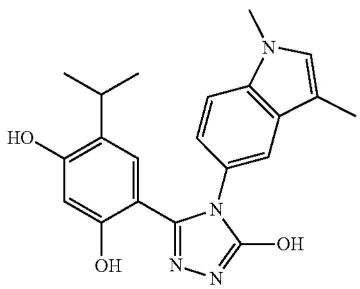 [SMILES: Cc1cn(C)c2ccc(-n3c(O)nnc3-c3cc(C(C)C)c(O)cc3O)cc12] | | 3-(2,4-DIHYDROXY-5-ISOPROPYL-PHENYL)-4-(1,3-DIMETHYL-INDOL-5-YL)-5-HYDROXY-[1,2,4] TRIAZOLE |
| 62 | 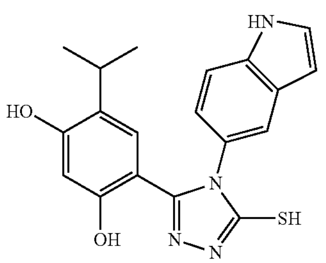 [SMILES: CC(C)c1cc(-c2nnc(S)n2-c2ccc3[nH]ccc3c2)c(O)cc1O] | | 3-(2,4-DIHYDROXY-5-ISOPROPYL-PHENYL)-4-(1H-INDOL-5-YL)-5-MERCAPTO-[1,2,4] TRIAZOLE |
| 63 | 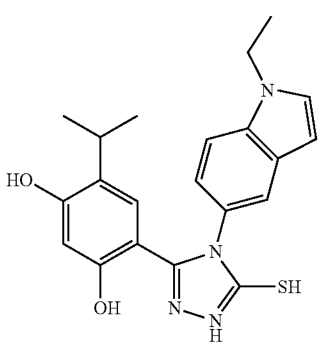 [SMILES: CCn1ccc2cc(-n3c(S)nnc3-c3cc(C(C)C)c(O)cc3O)ccc21] | | 3-(2,4-DIHYDROXY-5-ISOPROPYL-PHENYL)-4-(1-ETHYL-INDOL-5-YL)-5-MERCAPTO-[1,2,4] TRIAZOLE |
| 64 | 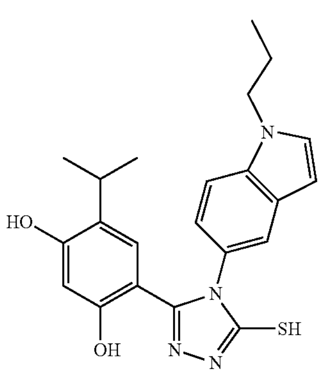 [SMILES: CCCn1ccc2cc(-n3c(S)nnc3-c3cc(C(C)C)c(O)cc3O)ccc21] | | 3-(2,4-DIHYDROXY-5-ISOPROPYL-PHENYL)-4-(1-PROPYL-INDOL-5-YL)-5-MERCAPTO-[1,2,4] TRIAZOLE |

TABLE 1-continued

| | STRUCTURE | TAUTOMERIC STRUCTURE | NAME |
|---|---|---|---|
| 65 | 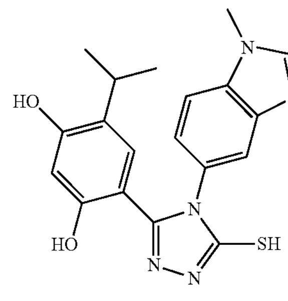 | | 3-(2,4-DIHYDROXY-5-ISOPROPYL-PHENYL)-4-(1-METHYL-2-TRIFLUOROMETHYL-BENZIMIDAZOL-5-YL)-5-MERCAPTO-[1,2,4]TRIAZOLE |
| 66 | 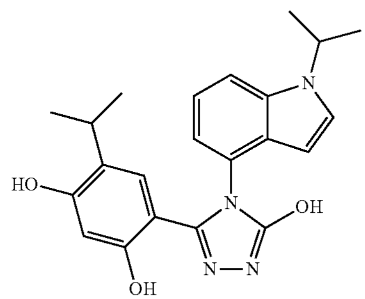 [SMILES: CC(C)c1cc(-c2nnc(O)n2-c2cccc3c2ccn3C(C)C)c(O)cc1O] | | 3-(2,4-DIHYDROXY-5-ISOPROPYL-PHENYL)-4-(1-ISOPROPYL-INDOL-4-YL)-5-HYDROXY-[1,2,4]TRIAZOLE |

TABLE 2

Compounds according to Formula (Ia)

| NO. | STRUCTURE | TAUTOMERIC STRUCTURE | NAME |
|---|---|---|---|
| 1A | 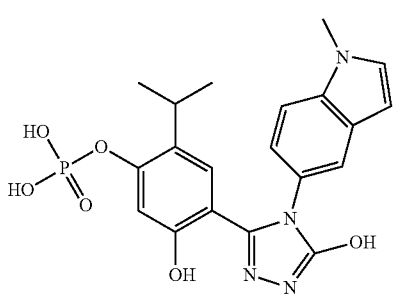 [SMILES: CC(C)c1cc(-c2nnc(O)n2-c2ccc3c(ccn3C)c2)c(O)cc1OP(=O)(O)O] | | 5-HYDROXY-4-(5-HYDROXY-4-(1-METHYL-1H-INDOL-5-YL)-4H-1,2,4-TRIAZOL-3-YL)-2-ISOPROPYLPHENYL DIHYDROGEN PHOSPHATE |
| 2A | 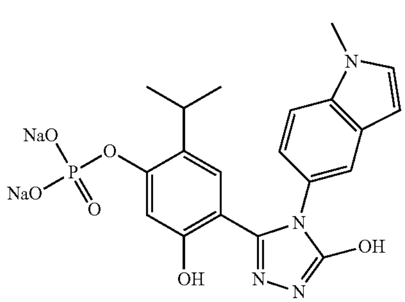 | | SODIUM 5-HYDROXY-4-(5-HYDROXY-4-(1-METHYL-1H-INDOL-5-YL)-4H-1,2,4-TRIAZOL-3-YL)-2-ISOPROPYLPHENYL PHOSPHATE |

TABLE 2-continued

Compounds according to Formula (Ia)

| NO. | STRUCTURE | TAUTOMERIC STRUCTURE | NAME |
|---|---|---|---|
| 3A | 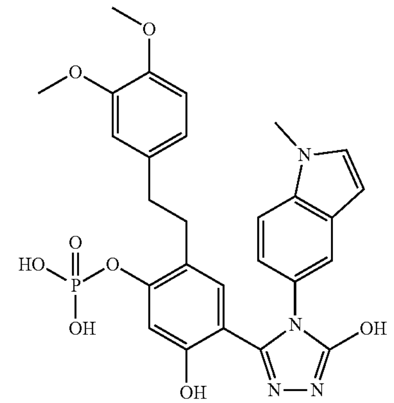 [SMILES: COc1ccc(CCc2cc(-c3nnc(O)n3-c3ccc4c(ccn4C)c3)c(O)cc2OP(=O)(O)O)cc1OC] | | 2-(3,4-DIMETHOXY-PHENETHYL)-5-HYDROXY-4-(5-HYDROXY-4-(1-METHYL-1H-INDOL-5-YL)-4H-1,2,4-TRIAZOL-3-YL)PHENYL DIHYDROGEN PHOSPHATE |
| 4A | 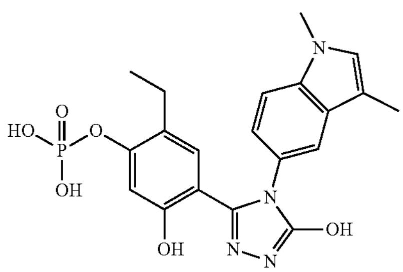 [SMILES: CCc1cc(-c2nnc(O)n2-c2ccc3c(c2)c(C)cn3C)c(O)cc1OP(=O)(O)O] | | 4-(4-(1,3-DIMETHYL-1H-INDOL-5-YL)-5-HYDROXY-4H-1,2,4-TRIAZOL-3-YL)-2-ETHYL-5-HYDROXYPHENYL DIHYDROGEN PHOSPHATE |

The Hsp90 inhibitory compounds used in the disclosed combination methods can be prepared according to the procedures disclosed in U.S. Patent Publication No. 2006/0,167,070, and WO2009/023,211.

These triazolone compounds typically can form a tautomeric structure as shown below and as exemplified by the tautomeric structures shown in Tables 1 and 2:

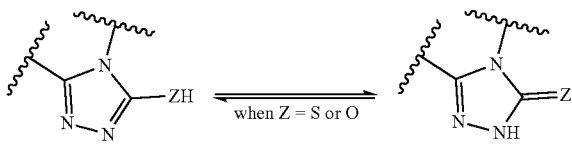

In an embodiment, the present invention provides a pharmaceutical combination for the treatment, prophylaxis, and amelioration of proliferative disorders, such as cancer. In a specific embodiment, the combination comprises one or more Hsp90 inhibitors according to formulae (I) or (Ia), or a compound in Tables 1 or 2, or a tautomer or a pharmaceutically acceptable salt thereof in addition to a platinum-containing anti-cancer agent.

In an embodiment, the combination includes a pharmaceutical composition or a single unit dosage form containing both an Hsp90 inhibitor and a platinum-containing anti-cancer agent. Pharmaceutical combinations and dosage forms described herein comprise the two active ingredients in relative amounts and formulated in such a way that a given pharmaceutical combination or dosage form can be used to treat proliferative disorders, such as cancer. Preferred pharmaceutical combinations and dosage forms comprise a compound of formulae (I) or (Ia), or a compound in Tables 1 or 2, or a tautomer or pharmaceutically acceptable salt thereof, in combination with a platinum-containing anticancer agent. In other embodiments, the Hsp90 inhibitor and the platinum-containing anticancer agent may be in individual or separate pharmaceutical compositions, depending on the dosing schedules, preferred routes of administration, and available formulations of the two compounds. Optionally, these embodiments can also contain one or more additional therapeutic agents.

The pharmaceutical combinations described herein are formulated to be compatible with its intended route of administration. Examples of routes of administration include parenteral, e.g., intravenous, intradermal, subcutaneous, oral, intranasal (e.g., inhalation), transdermal (topical), transmucosal, and rectal administration. In a specific embodiment, the combination is formulated in accordance with routine procedures as a pharmaceutical composition adapted for intravenous, subcutaneous, intramuscular, oral, intranasal or topical administration to human beings. In an embodiment, the combination is formulated in accordance with routine procedures for subcutaneous administration to human beings.

In a specific embodiment, the combination therapies described herein comprise one or more compounds and at least one other therapy which has the same mechanism of action as the compounds. In another specific embodiment, the combination therapies described herein comprise one or more compounds described herein and at least one other therapy which has a different mechanism of action than the compounds. In certain embodiments, the combination therapies described herein improve the therapeutic effect of one or more triazolone compounds described herein by functioning together with the platinum-containing anticancer agent to have an additive or synergistic effect. In certain embodiments, the combination therapies described herein reduce the side effects associated with the therapies. In certain embodiments, the combination therapies described herein reduce the effective dosage of one or more of the therapies.

In a specific embodiment, the combination comprising one or more triazolone compounds described herein is administered to a subject, preferably a human, to prevent, treat, manage, or ameliorate cancer, or one or more symptom thereof. In accordance with the invention, the pharmaceutical combinations described herein may also comprise one or more other agents being used, have been used, or are known to be useful in the treatment or amelioration of cancer, particularly breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, or colon cancer. The pharmaceutical combinations described herein utilize pharmaceutical compositions and dosage forms which comprise one or more excipients. Suitable excipients are well known to those skilled in the art of pharmacy.

The triazolone compounds described herein can be also formulated into or administered by controlled release means or by delivery devices that are well known to those of ordinary skill in the art. Examples include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566.

In an embodiment, the present invention also provides a method of treating a proliferative disorder in a subject, comprising administering to the subject an effective amount of the combination of an Hsp90 inhibitor and a platinum-containing anticancer agent as described herein. In an embodiment, the proliferative disorder is cancer. In one aspect of this embodiment, the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer.

Other anti-proliferative or anti-cancer therapies may be combined with the compounds described herein to treat proliferative diseases and cancer. Other therapies or anticancer agents that may be used in combination with the inventive anti-cancer agents described herein include surgery, radiotherapy (including gamma-radiation, neutron beam radiotherapy, electron beam radiotherapy, proton therapy, brachytherapy, and systemic radioactive isotopes), endocrine therapy, biologic response modifiers (including interferons, interleukins, and tumor necrosis factor (TNF)), hyperthermia and cryotherapy, agents to attenuate any adverse effects (e.g., antiemetics), and other approved chemotherapeutic drugs.

The therapeutic agents of the combination therapies described herein can be administered sequentially or concurrently. In an embodiment, the administration of the Hsp90 inhibitor and the platinum-containing anticancer agent are done concurrently. In another embodiment, the administration of the Hsp90 inhibitor and the platinum-containing anticancer agent are done separately. In another embodiment, the administration of the Hsp90 inhibitor and the platinum-containing anticancer agent are done sequentially. In an embodiment, the administration of the Hsp90 inhibitor and the platinum-containing anticancer agent are done until the cancer is cured or stabilized or improved.

In a specific embodiment, the present method includes treating, managing, or ameliorating cancer, or one or more symptoms thereof, comprising administering to a subject in need thereof one or more compounds represented by the structural formulae (I) or (Ia) or a compound in Table 1 or Table 2, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer.

In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an effective amount of a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with an effective amount of cisplatin. In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with a synergistic amount of cisplatin. In an embodiment, cisplatin is administered IV at a dose of between about 20 mg/m$^2$ to about 150 mg/m$^2$. In an embodiment, cisplatin is administered at a dose of about 20 mg/m$^2$ once daily. In an embodiment, cisplatin is administered IV at about 20 mg/m$^2$ once daily for 5 days per cycle. In an embodiment, cisplatin is administered IV at a dose of between about 75 mg/m$^2$ to about 100 mg/m$^2$. In an embodiment, cisplatin is administered IV at a dose of between about 75 mg/m$^2$ to about 100 mg/m$^2$ once every 4 weeks per cycle. In an embodiment, cisplatin is administered IV at a dose of about 100 mg/m$^2$ once every 4 weeks per cycle. In an embodiment, cisplatin is administered IV at a dose of between about 50 mg/m$^2$ to about 70 mg/m$^2$ once every 3 or 4 weeks per cycle. In an embodiment, the amount of the Hsp90 inhibitor is from about 2 mg/m$^2$ to about 260 mg/m$^2$. In an embodiment, the amount of the Hsp90 inhibitor is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. In an embodiment, the Hsp90 inhibitor is administered IV once weekly or twice weekly. In any one of the above embodiments, the cancer may have a KRAS mutation. In any one of the above embodiments, the cancer may have an ALK mutation. In any one of the above embodiments, the cancer may have a BRAF mutation.

In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an effective amount of a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with an effective amount of cisplatin. In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with a synergistic amount of cisplatin. In an embodiment, cisplatin is administered IV at a dose of between about 20 mg/m$^2$ to about 150 mg/m$^2$. In an embodiment, cisplatin is administered at a dose of about 20 mg/m$^2$ once daily. In an embodiment, cisplatin is administered IV at about 20 mg/m$^2$ once daily for 5 days per cycle. In an embodiment, cisplatin is administered IV at a dose of between about 75 mg/m$^2$ to about 100 mg/m$^2$. In an embodiment, cisplatin is administered IV at a dose of between about 75 mg/m$^2$ to about 100 mg/m$^2$ once every 4 weeks per cycle. In an embodiment, cisplatin is administered IV at a dose of about 100 mg/m$^2$ once every 4 weeks per cycle. In an embodiment, cisplatin is administered IV at a dose of between about 50 mg/m$^2$ to about 70 mg/m$^2$ once every 3 or 4 weeks per cycle. In an embodiment, the amount of the Hsp90 inhibitor is from about 2 mg/m$^2$ to about 260 mg/m$^2$. In an embodiment, the amount of the Hsp90 inhibitor is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. In an embodiment, the Hsp90 inhibitor is administered IV once weekly or twice weekly. In any one of the above embodiments, the cancer may have a KRAS mutation. In any one of the above embodiments, the cancer may have an ALK mutation. In any one of the above embodiments, the cancer may have a BRAF mutation.

In another embodiment, the method of treating a subject with cancer includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In another embodiment, the method of treating a subject with cancer includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or cancer. In an embodiment, the cancer has a KRAS mutation. In an embodiment, the cancer has an ALK mutation. In an embodiment, the cancer has a BRAF mutation.

In yet another embodiment, the method of treating a subject with cancer, wherein the subject is being or has been treated with a chemotherapeutic agent, includes administering to the subject an effective amount of a triazolone compound represented by the structural formulae (I) or (Ia) or a compound in Table 1 or Table 2, in combination with a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In an embodiment, the method of treating a subject with cancer, wherein the subject is being or has been treated with a chemotherapeutic agent, includes administering to the subject an effective amount of a triazolone compound represented by the structural formulae (I) or (Ia) or a compound in Table 1 or Table 2, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In another embodiment, the method of treating a subject with cancer, wherein the subject is being or has been treated with a chemotherapeutic agent, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the method of treating a subject with cancer, wherein the subject is being or has been treated with a chemotherapeutic agent, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with cisplatin. In an embodiment, cisplatin is administered IV at a dose of between about 20 mg/m$^2$ to about 150 mg/m$^2$. In an embodiment, cisplatin is administered at a dose of about 20 mg/m$^2$ once daily. In an embodiment, cisplatin is administered IV at about 20 mg/m$^2$ once daily for 5 days per cycle. In an embodiment, cisplatin is administered IV at a dose of between about 75 mg/m$^2$ to about 100 mg/m$^2$. In an embodiment, cisplatin is administered IV at a dose of between about 75 mg/m$^2$ to about 100 mg/m$^2$ once every 4 weeks per cycle. In an embodiment, cisplatin is administered IV at a dose of about 100 mg/m$^2$ once every 4 weeks per cycle. In an embodiment, cisplatin is administered IV at a dose of between about 50 mg/m$^2$ to about 70 mg/m$^2$ once every 3 or 4 weeks per cycle. In an embodiment, the amount of the Hsp90 inhibitor is from about 2 mg/m$^2$ to about 260 mg/m$^2$. In an embodiment, the amount of the Hsp90 inhibitor is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. In an embodiment, the Hsp90 inhibitor is administered IV once weekly or twice weekly. In any one of the above embodiments, the cancer may have a KRAS mutation. In any one of the above embodiments, the cancer may have an ALK mutation. In any one of the above embodiments, the cancer may have a BRAF mutation.

In another embodiment, the method of treating a subject with cancer, wherein the subject is being or has been treated with a chemotherapeutic agent, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the method of treating a subject with cancer, wherein the subject is being or has been treated with a chemotherapeutic agent, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with cisplatin. In an embodiment, cisplatin is administered IV at a dose of between about 20 mg/m$^2$ to about 150 mg/m$^2$. In an embodiment, cisplatin is administered at a dose of about 20 mg/m$^2$ once daily. In an embodiment, cisplatin is administered IV at about 20 mg/m$^2$ once daily for 5 days per cycle. In an embodiment, cisplatin is administered IV at a dose of between about 75 mg/m$^2$ to about 100 mg/m$^2$. In an embodiment, cisplatin is administered IV at a dose of between about 75 mg/m$^2$ to about 100 mg/m$^2$ once every 4 weeks per cycle. In an embodiment, cisplatin is administered IV at a dose of about 100 mg/m$^2$ once every 4 weeks per cycle. In an embodiment, cisplatin is administered IV at a dose of between about 50 mg/m$^2$ to about 70 mg/m$^2$ once every 3 or 4 weeks per cycle. In an embodiment, the amount of the Hsp90 inhibitor is from about 2 mg/m$^2$ to about 260 mg/m$^2$. In an embodiment, the amount of the Hsp90 inhibitor is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. In an embodiment, the Hsp90 inhibitor is administered IV once weekly or twice weekly. In any one of the above embodiments, the cancer may have a KRAS mutation. In any one of the above embodiments, the cancer may have an ALK mutation. In any one of the above embodiments, the cancer may have a BRAF mutation.

In an embodiment, the method of treating a subject with cancer, wherein the subject is being or has been treated with a chemotherapeutic agent, includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In an embodiment, the method of treating a subject with cancer, wherein the subject is being or has been treated with a chemotherapeutic agent, includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In an embodiment, the method of treating a subject with cancer, wherein the subject has proven refractory to other therapies but is no longer on these therapies, includes administering to the subject an effective amount of a triazolone compound represented by the structural formulae (I) or (Ia) or a compound in Table 1 or Table 2, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In another embodiment, the method of treating a subject with cancer, wherein the subject has proven refractory to other therapies but is no longer on these therapies, includes administering to the subject an effective amount of 3-(2,4-dihydroxy-5-isopropyl-phenyl)-4-(1-methyl-indol-5-yl)-5- hydroxy-[1,2,4]triazole, or a tautomer, or a pharmaceutically acceptable salt thereof, in combination with a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the method of treating a subject with cancer, wherein the subject has proven refractory to other therapies but is no longer on these therapies, includes administering to the subject an effective amount of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with cisplatin. In an embodiment, cisplatin is administered IV at a dose of between about 20 mg/m$^2$ to about 150 mg/m$^2$. In an embodiment, cisplatin is administered at a dose of about 20 mg/m$^2$ once daily. In an embodiment, cisplatin is administered IV at about 20 mg/m$^2$ once daily for 5 days per cycle. In an embodiment, cisplatin is administered IV at a dose from about 75 mg/m$^2$ to about 100 mg/m$^2$. In an embodiment, cisplatin is administered IV at a dose from about 75 mg/m$^2$ to about 100 mg/m$^2$ once every 4 weeks per cycle. In an embodiment, cisplatin is administered IV at a dose of about 100 mg/m$^2$ once every 4 weeks per cycle. In an embodiment, cisplatin is administered IV at a dose of between about 50 mg/m$^2$ to about 70 mg/m$^2$ once every 3 or 4 weeks per cycle. In an embodiment, the amount of the Hsp90 inhibitor is from about 2 mg/m$^2$ to about 260 mg/m$^2$. In an embodiment, the amount of the Hsp90 inhibitor is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. In an embodiment, the Hsp90 inhibitor is administered IV once weekly or twice weekly. In any one of the above embodiments, the cancer may have a KRAS mutation. In any one of the above embodiments, the cancer may have an ALK mutation. In any one of the above embodiments, the cancer may have a BRAF mutation.

In another embodiment, the method of treating a subject with cancer, wherein the subject has proven refractory to other therapies but is no longer on these therapies, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the method of treating a subject with cancer, wherein the subject has proven refractory to other therapies but is no longer on these therapies, includes administering to the subject an effective amount of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with cisplatin. In an embodiment, cisplatin is administered IV at a dose of between about 20 mg/m$^2$ to about 150 mg/m$^2$. In an embodiment, cisplatin is administered at a dose of about 20 mg/m$^2$ once daily. In an embodiment, cisplatin is administered IV at about 20 mg/m$^2$ once daily for 5 days per cycle. In an embodiment, cisplatin is administered IV at a dose from about 75 mg/m$^2$ to about 100 mg/m$^2$. In an embodiment, cisplatin is administered IV at a dose from about 75 mg/m$^2$ to about 100 mg/m$^2$ once every 4 weeks per cycle. In an embodiment, cisplatin is administered IV at a dose of about 100 mg/m$^2$ once every 4 weeks per cycle. In an embodiment, cisplatin is administered IV at a dose from about 50 mg/m$^2$ to about 70 mg/m$^2$ once every 3 or 4 weeks per cycle. In an embodiment, the amount of the Hsp90 inhibitor is from about 2 mg/m$^2$ to about 260 mg/m$^2$. In an embodiment, the amount of the Hsp90 inhibitor is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. In an embodiment, the Hsp90 inhibitor is administered IV once weekly or twice weekly. In any one of the above embodiments, the cancer may have a KRAS mutation. In any one of the above embodiments, the cancer may have an ALK mutation. In any one of the above embodiments, the cancer may have a BRAF mutation.

In an embodiment, the method of treating a subject with cancer, wherein the subject has proven refractory to other therapies but is no longer on these therapies, includes administering to the subject an effective amount of a triazolone compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In an embodiment, the method of treating a subject with cancer, wherein the subject has proven refractory to other therapies but is no longer on these therapies, includes administering to the subject an effective amount of a triazolone compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, in combination with a platinum-containing anticancer agent such as cisplatin, carboplatin, or oxaliplatin, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer. In an embodiment, the cancer has a KRAS mutation. In an embodiment, the cancer has an ALK mutation. In an embodiment, the cancer has a BRAF mutation.

In an further embodiment, the method includes inhibiting the growth of a cancer or tumor cell comprising the steps of: (a) contacting the cell with an effective amount of a compound of formulae (I) or (Ia) or a compound in Table (1) or Table (2), or tautomer or a pharmaceutically acceptable salt thereof; and (b) exposing the cell to an effective amount of a platinum-containing anticancer agent such as cisplatin, carboplatin, or oxaliplatin.

In an further embodiment, the method includes inhibiting the growth of a cancer or tumor cell comprising the steps of: (a) contacting the cell with an effective amount of a compound of -(2,4-dihydroxy-5-isopropyl-phenyl)-4-(1-methyl-indol-5-yl)-5-hydroxy-[1,2,4]triazole, or a tautomer, or a pharmaceutically acceptable salt thereof; and (b) exposing the cell to an effective amount of a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the invention also provides a method of inhibiting the growth of a cancer or tumor cell, comprising the steps of: (a) contacting the cell with an effective amount of a compound of -(2,4-dihydroxy-5-isopropyl-phenyl)-4-(1-methyl-indol-5-yl)-5-hydroxy-[1,2,4]triazole, or a tautomer, or a pharmaceutically acceptable salt thereof; and (b) exposing the cell to an effective amount of cisplatin. In an embodiment, the cancer has a KRAS mutation. In an embodiment, the cancer has an ALK mutation. In an embodiment, the cancer has a BRAF mutation.

In another embodiment, the invention also provides a method of inhibiting the growth of a cancer or tumor cell, comprising the steps of: (a) contacting the cell with an effective amount of a compound of 5-hydroxy-4-(5-hydroxy-4-(1-methyl-1H-indol-5-yl)-4H-1,2,4-triazol-3-yl)-2-isopropylphenyl dihydrogen phosphate, or tautomer or a pharmaceutically acceptable salt thereof; and (b) exposing the cell to an effective amount of a platinum-containing anticancer agent such as cisplatin, carboplatin, or oxaliplatin. In an embodiment, the cancer has a KRAS mutation. In an embodiment, the cancer has an ALK mutation. In an embodiment, the cancer has a BRAF mutation.

In another embodiment, the invention also provides a method of inhibiting the growth of a cancer or tumor cell, comprising the steps of: (a) contacting the cell with an effective amount of a compound of 5-hydroxy-4-(5-hydroxy-4-(1-methyl-1H-indol-5-yl)-4H-1,2,4-triazol-3-yl)-2-isopropylphenyl dihydrogen phosphate, or tautomer or a pharmaceutically acceptable salt thereof; and (b) exposing the cell to an effective amount of cisplatin. In an embodiment, the cancer has a KRAS mutation. In an embodiment, the cancer has an ALK mutation. In an embodiment, the cancer has a BRAF mutation.

In general, the recommended daily dose range of a triazolone compound for the conditions described herein lie within the range of from about 0.01 mg to about 1000 mg per day, given as a single once-a-day dose preferably as divided doses throughout a day. In an embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different cancers, as will be readily known by those of ordinary skill in the art. Similarly, amounts sufficient to prevent, manage, treat or ameliorate such cancers, but insufficient to cause, or sufficient to reduce, adverse effects associated with the triazolone compounds described herein are also encompassed by the above described dosage amounts and dose frequency schedules. Further, when a patient is administered multiple dosages of a triazolone compound described herein, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition comprising a triazolone compound described herein administered to prevent, treat, manage, or ameliorate cancer, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition comprising a compound described herein administered to prevent, treat, manage, or ameliorate cancer, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg. The unit dose can be administered 1, 2, 3, 4 or more times daily, or once every 2, 3, 4, 5, 6 or 7 days, or once weekly, once every two weeks, once every three weeks or once monthly.

In certain embodiments, when the triazolone compounds described herein are administered in combination with a platinum-containing anticancer agent, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies are administered within the same patient visit.

In certain embodiments, one or more compounds described herein and one or more other the therapies (e.g., therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound described herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, a method of preventing, treating, managing, or ameliorating a proliferative disorders, such as cancer, or one or more symptoms thereof, the methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, preferably, once every 2 days, once every 3 days, once every 4 days, once every 5 days, once every 6 days, once every 7 days, once every 8 days, once every 10 days, once every two weeks, once every three weeks, or once a month. Alternatively, the dose can be divided into portions (typically equal portions) administered two, three, four or more times a day.

In an embodiment, the invention also provides the use of a compound of formulae (I) or (Ia), or a compound in Tables 1 or 2, or a pharmaceutically acceptable salt thereof for the manufacture of a medicament for the treatment of a subject with cancer. In an embodiment, the invention further provides the use of a compound of formulae (I) or (Ia), or a compound in Tables 1 or 2, or a pharmaceutically acceptable salt thereof for the manufacture of a medicament for the treatment of a subject with a cancer, in combination with a platinum-containing anticancer agent such as cisplatin, carboplatin, or oxaliplatin. In an embodiment, the invention further provides the use of a compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for the manufacture of a medicament for the treatment of a subject with a cancer, in combination with a platinum-containing anticancer agent such as cisplatin, carboplatin, or oxaliplatin. In an embodiment, the invention further provides the use of a compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, for the manufacture of a medicament for the treatment of a subject with a cancer, in combination with a platinum-containing anticancer agent such as cisplatin, carboplatin, or oxaliplatin. In an embodiment, the invention further provides the use of the compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for the manufacture of a medicament for the treatment of a subject with a cancer, in combination with cisplatin. In an embodiment, the invention further provides the synergistic use of the compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for the manufacture of a medicament for the treatment of a subject with a cancer, in combination with cisplatin.

In an embodiment, the invention also provides a compound of formulae (I) or (Ia) or a pharmaceutically acceptable salt thereof for use in treating a subject with a cancer. In an embodiment, the invention also provides a compound of formulae (I) or (Ia) or a pharmaceutically acceptable salt thereof for use in treating a subject with cancer in combination with a platinum-containing anticancer agent such as cisplatin, carboplatin, or oxaliplatin. In an embodiment, the invention also provides a compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for use in treating a subject with cancer in combination with a platinum-containing anticancer agent such as cisplatin, carboplatin, or oxaliplatin. In an embodiment, the invention also provides a compound of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, for use in treating a subject with cancer in combination with a platinum-containing anticancer agent such as cisplatin, carboplatin, or oxaliplatin. In an embodiment, the invention also provides a compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for use in treating a subject with cancer in combination with cisplatin. In an embodiment, the invention also provides a compound of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for synergistic use in treating a subject with cancer in combination with cisplatin.

Examples

In Vitro Combination Analysis of Ganetespib with Chemotherapy in Colorectal Cancer Cells A. Materials and Methods Cell Lines Human HCT-116 colorectal cancer cells (CRC) and MDA-MB-231 breast cancer cells were purchased from the American Type Culture Collection (Manassas, Va.) and grown following ATCC recommendations, in the presence of fetal bovine serum (10%), 2 mM L-glutamine and antibiotics (100 IU/ml penicillin and 100 µg/ml streptomycin, Sigma). Cells were maintained at 37° C., 5% $CO_2$ atmosphere.

Cell Viability Assays

Cell viability was measured using the alamarBlue assay (Invitrogen). In brief, cells were plated in 96-well plates in triplicate at 5K cells per well and incubated at 37° C., 5% $CO_2$ atmosphere for 24 hr prior to the addition of drug or vehicle (0.3% DMSO) to the culture medium. After 72 hr, 10 µl/well alamarBlue was added to the wells and incubated for an additional 3 hr at 37° C., 5% $CO_2$ atmosphere. Fluorescence ($56_{EX}/590_{EM}$ nM) was measured with a SpectraMax microplate reader (Molecular Devices) and the resulting data were used to calculate cell viability, normalized to vehicle control.

Mouse Studies

Six to seven week old, female CB17/Icr-Prkdc$^{scid}$/Crl (SCID) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Animals were between seven to eight weeks of age at implantation. To implant HCT-116 or MDA-MB-231 tumor cells into SCID mice, cells were harvested by trypsinization, washed in PBS and re-susupended at a concentration of 5×10(7) cells/mL in 50% non-supplemented medium and 50% Matrigel Basement Membrane Matrix (BD Biosciences; Bedford, Mass., USA). Using a 27 gauge needle and 1 cc syringe, 5×10(6) cells in 0.1 mL of a cell suspension were injected subcutaneously into the flanks of SCID mice.

Tumors were then permitted to develop in vivo until the majority reached 95-195 mm³ in tumor volume. Animals with oblong, very small or large tumors were discarded and only animals carrying tumors that displayed consistent growth rates were selected for studies. Tumor volumes (V) were calculated by caliper measurement of the width (W), length (L) and thickness (T) of tumors using the following formula: V=0.5236×(L×W×T). Animals were randomized into treatment groups so that the average tumor volumes of each group were similar at the start of dosing.

Ganetespib was prepared by dissolving the appropriate amounts of the compound in dimethyl sulfoxide (DMSO) by sonication in an ultrasonic water bath. Stock solutions were prepared weekly, stored at −20° C. and diluted fresh each day for dosing. A solution of 20% Cremophor RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) was also prepared by first heating 100% Cremophor RH40 at 50-60° C. until liquefied and clear, diluting 1:5 with 100% D5W, reheating again until clear and then mixing well. This solution can be stored at room temperature for up to 3 months prior to use. To prepare DRD formulations for daily dosing, DMSO stock solutions were diluted 1:10 with 20% Cremophor RH40. The final DRD formulation for dosing contained 10% DMSO, 18% Cremophor RH40, 3.6% dextrose, 68.4% water and the appropriate amount of test article. Animals were intravenously (i.v.) injected with this formulation at 10 mL per kg body weight 1 day each week. Cisplatin was prepared fresh in saline and given intravenously 6 hours after ganetespib injection, once per week.

B. Combination Studies with Ganetespib and Cisplatin

Figure 2:
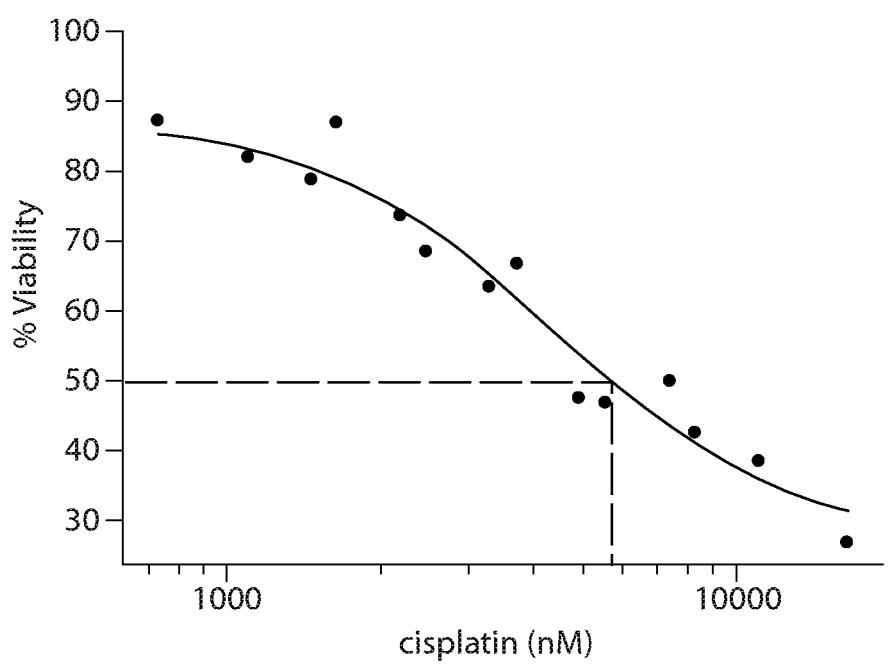
FIG. 2 shows a dose-dependent curve with the $IC_{50}$ of cisplatin at about 5.7 µM.

The half maximal inhibitory concentration ($IC_{50}$) for ganetespib (synthesized at Synta Pharmaceuticals) and cisplatin (purchased from Sigma) were first determined using a 1.5-fold serial dilution series of compound. After HCT-116 cells were exposed to drug for 72 hr, cell viability was measured and results were fit to a four parameter logistic model (XLFit, ID Business Solutions) shown in FIGS. 1 and 2. The $IC_{50}$ for ganetespib was calculated at approximately 32 nM, and 5.7 µM for cisplatin.

Figure 3:
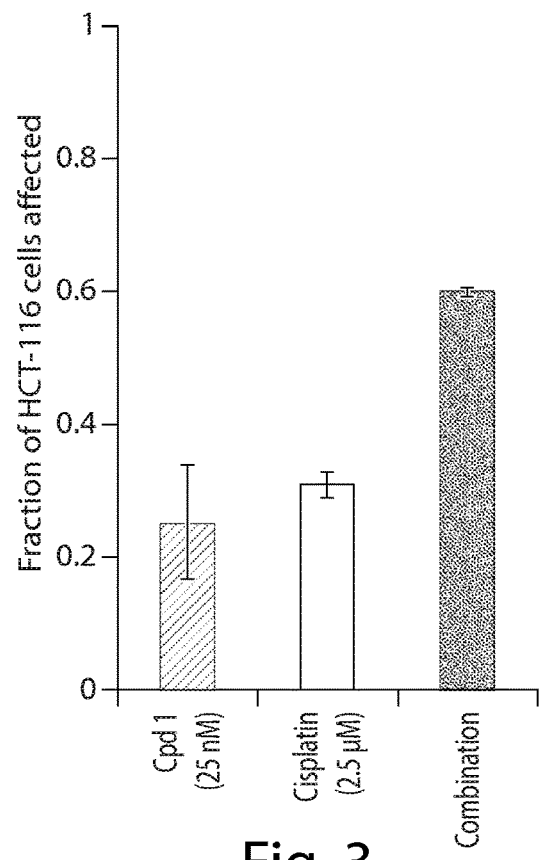
FIG. 3 shows significant killing of HCT-116 cells by ganetespib in combination with cisplatin. Cells were exposed to the indicated single agent or combination, concurrently, for 3 days.
Figure 4:
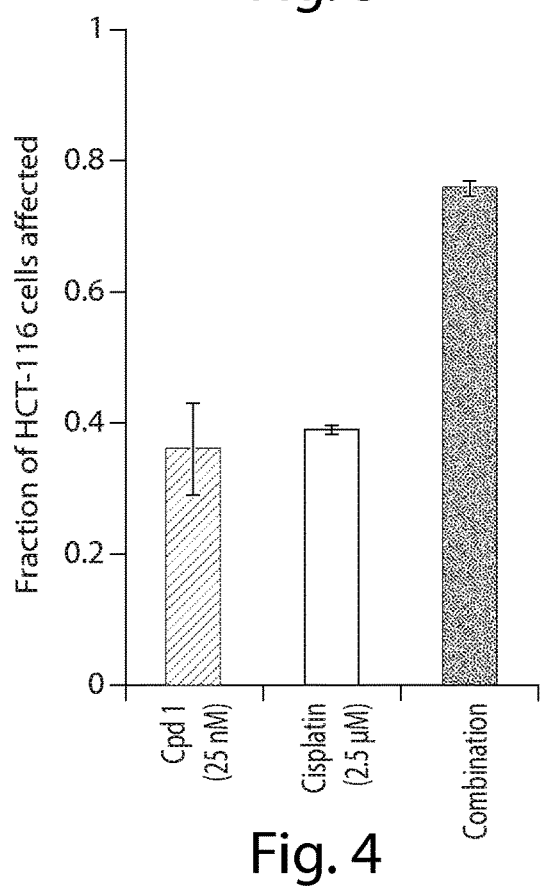
FIG. 4 shows significant killing of HCT-116 cells by the sequential combination of ganetespib with cisplatin. Cells were exposed to ganetespib for 1 hour, washed and then treated with vehicle (DMSO) or indicated chemotherapeutic for 3 days. Single agent chemotherapeutic was dosed for 3 days.

Combinations between ganetespib and cisplatin were then performed in HCT-116 cells concurrently based on the $IC_{50}$ for each agent in matrix format with 54 combination pairs for each drug. The combined drugs, as well as each drug alone, were incubated with the cells for 3 days and the surviving fraction of cells relative to control was determined using the alamarBlue assay. Representative figures are shown in FIGS. 3 and 4. The combination of ganetespib with cisplatin displayed enhanced cytotoxicity relative to single agent drugs alone. Similar results were observed when cells were exposed to ganetespib for just one hour, washed and then treated with cisplatin for 3 days.

Figure 5:
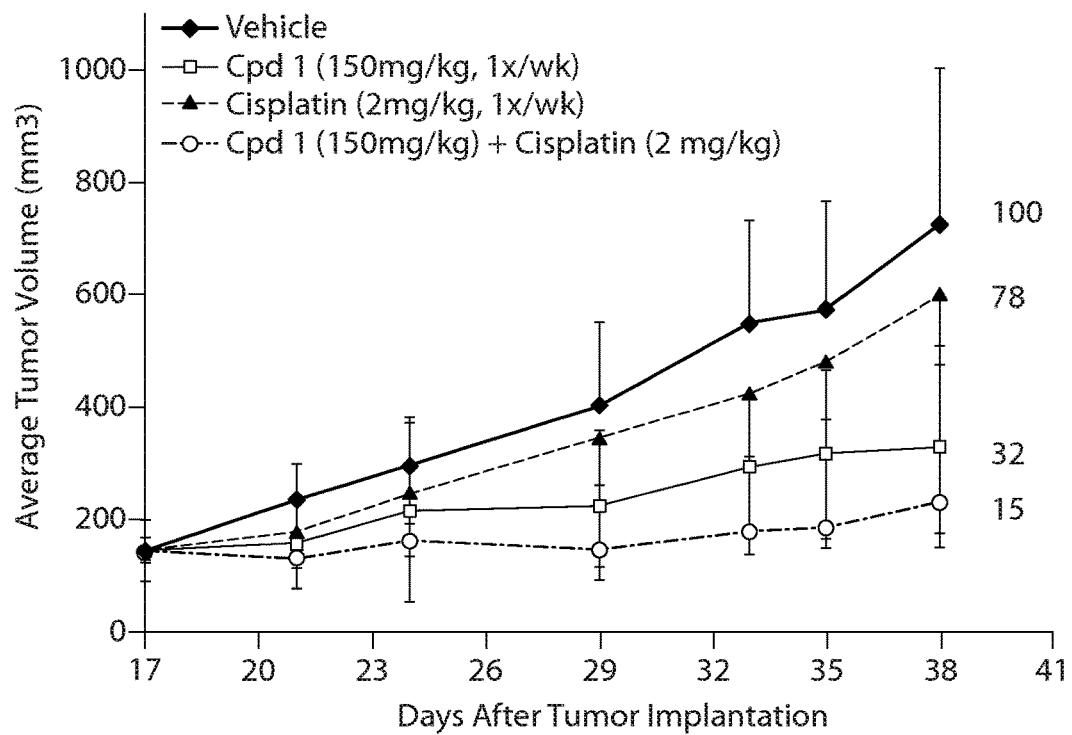
FIG. 5 shows substantial treatment improvement by a combination of ganetespib with cisplatin in an animal model of HCT-116 colon cancer xenograft. Ganetespib (150 mg/kg) was given as a single bolus injection 6 hours prior to cisplatin (2 mg/kg) administration.
Figure 6:
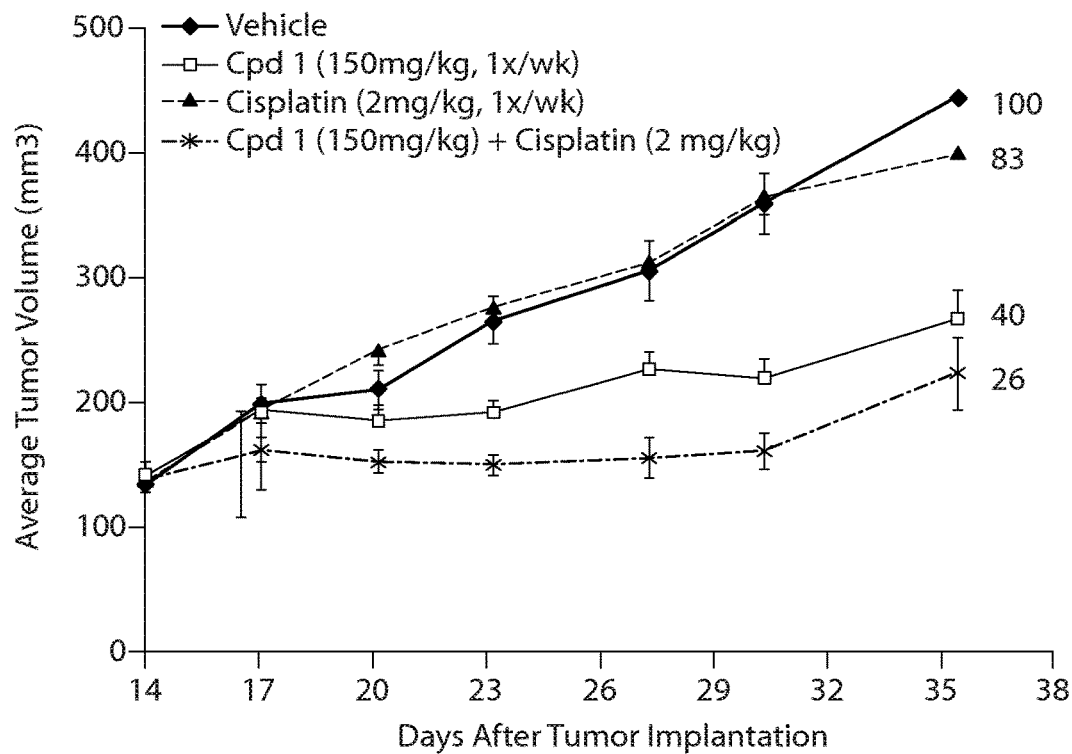
FIG. 6 shows substantial treatment improvement by a combination of ganetespib with cisplatin in an animal model of MDA-MB-231 breast cancer tumor xenograft. Ganetespib (150 mg/kg) was given as a single bolus injection 6 hours prior to cisplatin (2 mg/kg) administration.

Combinations between ganetespib and cisplatin were further performed in animal models, using HCT-116 colon cancer or MDA-MB-231 breast cancer tumor xenografts. Ganetespib (150 mg/kg) was given as a single bolus injection 6 hours prior to cisplatin (2 mg/kg) administration. Representative figures are shown in FIGS. 5 and 6. In both cancer xenograft models, the combination of ganetespib with cisplatin displayed greater antitumor activity relative to monotherapy.

In conclusion, these data support the use of ganetespib in combination with cisplatin in solid cancers such as gastric, bladder, colorectal, breast, ovarian and lung. See also Acquaviva et al, Mol Cancer Ther. 2012, September issue.

All publications, patent applications, patents, and other documents cited herein are incorporated by reference in their entirety. In case of conflict, the present specification, including definitions, will control. In addition, the materials, methods, and examples throughout the specification are illustrative only and not intended to be limiting in any way.

What is claimed is:

1. A method of treating cancer, wherein the cancer is breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, non-small cell lung cancer, bladder cancer, testicular tumor, ovarian cancer, lymphoma, leukemia, multiple myeloma, or colon cancer, comprising administering to the subject (a) an effective amount of an Hsp90 inhibitor, wherein the Hsp90 inhibitor is selected from the group consisting of 3-(2,4-dihydroxy-5-isopropyl-phenyl)-4-(1-methyl-indol-5-yl)-5-hydroxy-[1,2,4] triazole or a tautomer or a pharmaceutically acceptable salt thereof and 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, and (b) a platinum-containing anticancer agent, wherein the platinum-containing anticancer agent is selected from the group consisting of cisplatin, carboplatin, and oxaliplatin.

2. The method of claim 1, wherein the cancer is gastric cancer, bladder cancer, pancreatic cancer, non-small cell lung cancer, ovarian cancer, or colorectal cancer.

3. The method of claim 1, wherein the method comprising administering a compound of 3-(2,4-dihydroxy-5-isopropyl-phenyl)-4-(1-methyl-indol-5-yl)-5-hydroxy-[1,2,4] triazole, or a tautomer or a pharmaceutically acceptable salt thereof, and cisplatin.

4. The method of claim 3, wherein cisplatin is administered at a dose from about 20 mg/m$^2$ to about 150 mg/m$^2$.

5. The method of claim 3, wherein the amount of the triazole compound is from about 2 mg/m$^2$ to about 260 mg/m$^2$.

6. The method of claim 5, wherein the amount of the triazole compound is about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$.

7. The method of claim 5, wherein the Hsp90 inhibitor is administered IV once weekly or twice weekly.

* * * * *